(12) United States Patent
Lynch

(10) Patent No.: US 11,571,497 B2
(45) Date of Patent: *Feb. 7, 2023

(54) PLATELET-DERIVED GROWTH FACTOR COMPOSITIONS AND METHODS OF USE THEREOF

(71) Applicant: BioMimetic Therapeutics, LLC, Franklin, TN (US)

(72) Inventor: Samuel E. Lynch, Franklin, TN (US)

(73) Assignee: BioMimetic Therapeutics, LLC, Franklin, TN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/211,979

(22) Filed: Jul. 15, 2016

(65) Prior Publication Data

US 2017/0072108 A1  Mar. 16, 2017

Related U.S. Application Data

(60) Continuation of application No. 11/778,498, filed on Jul. 16, 2007, now Pat. No. 9,545,377, which is a division of application No. 11/159,533, filed on Jun. 23, 2005, now Pat. No. 7,473,678, which is a continuation-in-part of application No. 10/965,319, filed on Oct. 14, 2004, now abandoned.

(51) Int. Cl.
| | | |
|---|---|---|
| A61K 38/18 | (2006.01) | |
| C07K 14/49 | (2006.01) | |
| A61L 27/12 | (2006.01) | |
| A61L 27/24 | (2006.01) | |
| A61L 27/56 | (2006.01) | |
| A61L 27/54 | (2006.01) | |
| A61L 27/40 | (2006.01) | |
| A61L 27/58 | (2006.01) | |
| A61F 2/28 | (2006.01) | |
| A61L 27/22 | (2006.01) | |
| A61K 9/00 | (2006.01) | |
| A61L 27/02 | (2006.01) | |
| A61L 27/42 | (2006.01) | |

(52) U.S. Cl.
CPC ........... *A61L 27/54* (2013.01); *A61F 2/28* (2013.01); *A61K 9/0063* (2013.01); *A61K 38/1858* (2013.01); *A61L 27/025* (2013.01); *A61L 27/12* (2013.01); *A61L 27/227* (2013.01); *A61L 27/24* (2013.01); *A61L 27/40* (2013.01); *A61L 27/425* (2013.01); *A61L 27/56* (2013.01); *A61L 27/58* (2013.01); *C07K 14/49* (2013.01); *A61F 2002/2835* (2013.01); *A61F 2210/0004* (2013.01); *A61L 2300/414* (2013.01); *A61L 2400/06* (2013.01); *A61L 2430/02* (2013.01); *A61L 2430/06* (2013.01); *A61L 2430/10* (2013.01); *A61L 2430/12* (2013.01)

(58) Field of Classification Search
CPC .......... A61L 27/12; A61L 27/24; A61L 27/54; A61L 27/56; A61P 19/08; A61P 19/04
See application file for complete search history.

(56) References Cited

U.S. PATENT DOCUMENTS

| | | |
|---|---|---|
| 2,124,316 A | 7/1938 | Antoniades et al. |
| 3,943,072 A | 3/1976 | Thomson et al. |
| 4,845,075 A | 7/1989 | Murray et al. |
| 4,861,757 A | 8/1989 | Antoniades et al. |
| 4,874,746 A | 10/1989 | Antoniades et al. |
| RE33,161 E | 2/1990 | Brown et al. |
| 4,904,259 A | 2/1990 | Itay |
| RE33,221 E | 5/1990 | Brown et al. |
| 4,963,145 A | 10/1990 | Takagi et al. |
| 4,975,526 A | 12/1990 | Kuberasampath et al. |
| 5,011,910 A | 4/1991 | Marshall et al. |
| 5,013,649 A | 5/1991 | Wang et al. |
| 5,019,559 A | 5/1991 | Antoniades et al. |
| 5,034,375 A | 7/1991 | Antoniades et al. |
| 5,035,887 A | 7/1991 | Antoniades et al. |
| 5,045,633 A | 9/1991 | Murray et al. |
| 5,053,212 A | 10/1991 | Constantz et al. |
| 5,106,748 A | 4/1992 | Wozney et al. |
| 5,108,922 A | 4/1992 | Wang et al. |
| 5,112,354 A | 5/1992 | Sires |
| 5,116,738 A | 5/1992 | Wang et al. |
| 5,124,316 A | 6/1992 | Antoniades et al. |
| 5,128,321 A | 7/1992 | Murray et al. |
| 5,129,905 A | 7/1992 | Constantz |
| 5,141,905 A | 8/1992 | Rosen et al. |

(Continued)

FOREIGN PATENT DOCUMENTS

| | | |
|---|---|---|
| EP | 0289584 A1 | 11/1988 |
| EP | 0479799 A1 | 4/1992 |

(Continued)

OTHER PUBLICATIONS

Nevins et al., J. Periodontol., Sep. 2003, vol. 74(9):1282-1292.*

(Continued)

*Primary Examiner* — Xiaozhen Xie
(74) *Attorney, Agent, or Firm* — Foley Hoag LLP; Hilary Dorr Lang

(57) ABSTRACT

A method for promoting growth of bone, periodontium, ligament, or cartilage in a mammal by applying to the bone, periodontium, ligament, or cartilage a composition comprising platelet-derived growth factor at a concentration in the range of about 0.1 mg/mL to about 1.0 mg/mL in a pharmaceutically acceptable liquid carrier and a pharmaceutically-acceptable solid carrier.

23 Claims, 2 Drawing Sheets

(56) References Cited

U.S. PATENT DOCUMENTS

| | | |
|---|---|---|
| 5,149,691 A | 9/1992 | Rutherford |
| 5,165,938 A | 11/1992 | Knighton |
| 5,187,076 A | 2/1993 | Wozney et al. |
| 5,187,263 A | 2/1993 | Murray et al. |
| 5,219,576 A | 6/1993 | Chu et al. |
| 5,219,759 A | 6/1993 | Heldin et al. |
| 5,270,300 A | 12/1993 | Hunziker |
| 5,290,708 A | 3/1994 | Ashihara et al. |
| 5,338,772 A * | 8/1994 | Bauer ............ A61L 27/46 428/304.4 |
| 5,376,636 A | 12/1994 | Rutherford et al. |
| 5,422,340 A * | 6/1995 | Ammann ............ A61F 2/28 424/489 |
| 5,457,093 A | 10/1995 | Cini et al. |
| 5,460,962 A | 10/1995 | Kemp |
| 5,516,896 A | 5/1996 | Murray et al. |
| 5,518,680 A | 5/1996 | Cima et al. |
| 5,531,794 A | 7/1996 | Takagi et al. |
| 5,533,836 A | 7/1996 | Moore |
| 5,549,123 A | 8/1996 | Okuyama et al. |
| 5,599,558 A | 2/1997 | Gordinier et al. |
| 5,629,191 A | 5/1997 | Cahn |
| 5,635,372 A | 6/1997 | Celeste et al. |
| 5,650,176 A | 7/1997 | Lee et al. |
| 5,747,273 A | 5/1998 | Khosravi et al. |
| 5,759,815 A | 6/1998 | Charette et al. |
| 5,776,193 A * | 7/1998 | Kwan ............ A61F 2/28 424/423 |
| 5,783,217 A | 7/1998 | Lee et al. |
| 5,804,176 A | 9/1998 | Grotendorst |
| 5,837,258 A | 11/1998 | Grotendorst |
| 5,853,746 A | 12/1998 | Hunziker |
| 5,866,165 A | 2/1999 | Liu et al. |
| 5,962,028 A | 10/1999 | Constantz |
| 5,965,403 A | 10/1999 | Celeste et al. |
| 5,972,385 A | 10/1999 | Liu et al. |
| 6,018,095 A | 1/2000 | Lerch et al. |
| 6,027,742 A | 2/2000 | Lee et al. |
| 6,030,636 A | 2/2000 | Randolph et al. |
| 6,077,989 A | 6/2000 | Kandel et al. |
| 6,083,910 A | 7/2000 | Kunitani et al. |
| 6,136,029 A | 10/2000 | Johnson et al. |
| 6,180,606 B1 | 1/2001 | Chen et al. |
| 6,214,368 B1 | 4/2001 | Lee et al. |
| 6,221,625 B1 | 4/2001 | Ashihara et al. |
| 6,224,635 B1 | 5/2001 | Ricci et al. |
| 6,280,191 B1 | 8/2001 | Gordon |
| 6,280,478 B1 | 8/2001 | Richter et al. |
| 6,281,195 B1 | 8/2001 | Rueger et al. |
| 6,287,341 B1 | 9/2001 | Lee et al. |
| 6,313,189 B1 | 11/2001 | Wenz et al. |
| 6,316,091 B1 | 11/2001 | Richart et al. |
| 6,331,312 B1 | 12/2001 | Lee et al. |
| 6,346,123 B1 | 2/2002 | McKay |
| 6,398,972 B1 | 6/2002 | Blasetti et al. |
| 6,440,444 B2 | 8/2002 | Boyce et al. |
| 6,451,059 B1 | 9/2002 | Janas et al. |
| 6,465,205 B2 | 10/2002 | Hicks, Jr. |
| 6,468,543 B1 | 10/2002 | Gilbertson et al. |
| 6,541,022 B1 | 4/2003 | Murphy et al. |
| 6,541,037 B1 | 4/2003 | Lee et al. |
| 6,558,307 B2 | 5/2003 | Headley |
| 6,576,015 B2 | 6/2003 | Geistlich et al. |
| 6,586,388 B2 | 7/2003 | Oppermann et al. |
| 6,592,507 B2 | 7/2003 | Jorgensen et al. |
| 6,599,558 B1 | 7/2003 | Al-Lamee et al. |
| 6,613,566 B2 | 9/2003 | Kandler et al. |
| 6,641,552 B1 | 11/2003 | Kingsley et al. |
| 6,649,072 B2 | 11/2003 | Brandt et al. |
| 6,652,473 B2 | 11/2003 | Kaufman et al. |
| 6,663,870 B2 | 12/2003 | Hart et al. |
| 6,710,025 B1 | 3/2004 | Spector |
| 6,739,112 B1 | 5/2004 | Marino |
| 6,743,232 B2 | 6/2004 | Overaker et al. |
| 6,866,991 B2 | 3/2005 | Gilbertson et al. |
| 6,884,428 B2 | 4/2005 | Binette et al. |
| 6,903,078 B1 | 6/2005 | Williams |
| 6,949,251 B2 | 9/2005 | Dalal et al. |
| 6,972,130 B1 | 12/2005 | Lee et al. |
| 6,974,862 B2 | 12/2005 | Ringeisen et al. |
| 7,005,135 B2 | 2/2006 | Janas et al. |
| 7,012,034 B2 | 3/2006 | Heide et al. |
| 7,022,506 B2 | 4/2006 | Brighton et al. |
| 7,041,641 B2 | 5/2006 | Rueger et al. |
| 7,052,518 B2 | 5/2006 | Irie et al. |
| 7,087,540 B2 | 8/2006 | Heide et al. |
| 7,148,209 B2 | 12/2006 | Hoemann et al. |
| 7,192,592 B2 | 3/2007 | Gilbertson et al. |
| 7,192,604 B2 | 3/2007 | Brown et al. |
| 7,250,550 B2 | 7/2007 | Overby et al. |
| 7,357,941 B2 | 4/2008 | Dalal et al. |
| 7,390,498 B2 | 6/2008 | Dalal et al. |
| 7,473,678 B2 | 1/2009 | Lynch |
| 7,491,384 B2 | 2/2009 | Hart et al. |
| 7,597,883 B2 | 10/2009 | Hart et al. |
| 9,545,377 B2 | 1/2017 | Lynch |
| 11,318,230 B2 | 5/2022 | Lynch |
| 11,364,325 B2 | 6/2022 | Lynch |
| 2001/0014662 A1 | 8/2001 | Rueger et al. |
| 2001/0016646 A1 | 8/2001 | Rueger et al. |
| 2001/0016703 A1 | 8/2001 | Wironen et al. |
| 2001/0020188 A1 | 9/2001 | Sander |
| 2001/0038848 A1 | 11/2001 | Donda et al. |
| 2002/0004225 A1 | 1/2002 | Hart et al. |
| 2002/0006437 A1 | 1/2002 | Grooms et al. |
| 2002/0018796 A1 | 2/2002 | Wironen |
| 2002/0022885 A1 | 2/2002 | Ochi |
| 2002/0037799 A1 | 3/2002 | Li et al. |
| 2002/0082220 A1 | 6/2002 | Hoemann et al. |
| 2002/0082694 A1 | 6/2002 | McKay |
| 2002/0098222 A1 | 7/2002 | Wironen et al. |
| 2002/0115647 A1 | 8/2002 | Halvorsen et al. |
| 2002/0120281 A1 | 8/2002 | Overaker |
| 2002/0127265 A1 | 9/2002 | Bowman et al. |
| 2002/0131989 A1 | 9/2002 | Brown et al. |
| 2002/0193883 A1 | 12/2002 | Wironen |
| 2003/0006025 A1 | 1/2003 | Manini et al. |
| 2003/0049328 A1 | 3/2003 | Dalal et al. |
| 2003/0055511 A1 | 3/2003 | Schryver et al. |
| 2003/0105015 A1 | 6/2003 | Gilbertson et al. |
| 2003/0109000 A1 | 6/2003 | Moore et al. |
| 2003/0109537 A1 | 6/2003 | Turner et al. |
| 2003/0114936 A1 | 6/2003 | Sherwood et al. |
| 2003/0125252 A1 | 7/2003 | Underhill et al. |
| 2003/0152606 A1 | 8/2003 | Gerber |
| 2003/0180376 A1 | 9/2003 | Dalal et al. |
| 2003/0193106 A1 | 10/2003 | Yu et al. |
| 2003/0199615 A1 | 10/2003 | Chaput et al. |
| 2003/0203002 A1 | 10/2003 | Murphy et al. |
| 2003/0224488 A1 | 12/2003 | Fox et al. |
| 2003/0228364 A1 | 12/2003 | Nathan |
| 2003/0232071 A1 | 12/2003 | Gower et al. |
| 2003/0235622 A1 | 12/2003 | Tas |
| 2004/0002770 A1 | 1/2004 | King et al. |
| 2004/0014727 A1 | 1/2004 | Garrett |
| 2004/0022825 A1 | 2/2004 | Lagow |
| 2004/0033949 A1 | 2/2004 | Bunting et al. |
| 2004/0043031 A1 | 3/2004 | Hart et al. |
| 2004/0064194 A1 | 4/2004 | Irie et al. |
| 2004/0076685 A1 | 4/2004 | Tas |
| 2004/0078077 A1 | 4/2004 | Binette et al. |
| 2004/0078090 A1 | 4/2004 | Binette et al. |
| 2004/0138758 A1 | 7/2004 | Evans et al. |
| 2004/0197311 A1 | 10/2004 | Brekke et al. |
| 2004/0224027 A1 | 11/2004 | Spiro et al. |
| 2004/0228870 A9 | 11/2004 | Hart et al. |
| 2004/0230303 A1 | 11/2004 | Gomes et al. |
| 2004/0243133 A1 | 12/2004 | Materna |
| 2004/0265350 A1 | 12/2004 | Sambrook et al. |
| 2005/0027367 A1 | 2/2005 | Heide et al. |
| 2005/0031694 A1 | 2/2005 | Gilbertson et al. |
| 2005/0074481 A1 | 4/2005 | Brekke et al. |
| 2005/0098915 A1 | 5/2005 | Long et al. |
| 2005/0107162 A1 | 5/2005 | Kilby et al. |

(56) References Cited

U.S. PATENT DOCUMENTS

| | | |
|---|---|---|
| 2005/0107887 A1 | 5/2005 | Knothe Tate et al. |
| 2005/0119754 A1 | 6/2005 | Trieu et al. |
| 2005/0169893 A1 | 8/2005 | Koblish et al. |
| 2005/0170012 A1 | 8/2005 | Dalal et al. |
| 2005/0177203 A1 | 8/2005 | Brighton et al. |
| 2005/0187162 A1 | 8/2005 | Dhanaraj et al. |
| 2005/0251266 A1 | 11/2005 | Maspero et al. |
| 2006/0029578 A1 | 2/2006 | Hoemann et al. |
| 2006/0084602 A1 | 4/2006 | Lynch |
| 2006/0149392 A1 | 7/2006 | Hsieh et al. |
| 2006/0153816 A1 | 7/2006 | Brown et al. |
| 2006/0153817 A1 | 7/2006 | Kihm et al. |
| 2006/0153818 A1 | 7/2006 | Dhanaraj et al. |
| 2006/0154367 A1 | 7/2006 | Kihm et al. |
| 2006/0177475 A1 | 8/2006 | Rueger et al. |
| 2006/0190043 A1 | 8/2006 | Brighton et al. |
| 2006/0198939 A1 | 9/2006 | Smith et al. |
| 2006/0205652 A1 | 9/2006 | Zamora et al. |
| 2006/0233853 A1 | 10/2006 | Remington et al. |
| 2006/0247156 A1 | 11/2006 | Vanderby et al. |
| 2006/0292198 A1 | 12/2006 | Dalal et al. |
| 2007/0003752 A1 | 1/2007 | Bruce et al. |
| 2007/0026044 A1 | 2/2007 | Bunting et al. |
| 2007/0048381 A1 | 3/2007 | Hart et al. |
| 2007/0053951 A1 | 3/2007 | Gonzalez Santos et al. |
| 2007/0129807 A1 | 6/2007 | Lynch et al. |
| 2007/0160681 A1 | 7/2007 | Park et al. |
| 2007/0190101 A1 | 8/2007 | Yang et al. |
| 2007/0191851 A1 | 8/2007 | Ashammakhi |
| 2007/0207185 A1 | 9/2007 | Hart et al. |
| 2007/0218098 A1 | 9/2007 | Reif et al. |
| 2007/0244484 A1 | 10/2007 | Luginbuehl |
| 2007/0259018 A1 | 11/2007 | McKay |
| 2007/0260326 A1 | 11/2007 | Williams et al. |
| 2007/0282455 A1 | 12/2007 | Luginbuehl et al. |
| 2008/0027470 A1 | 1/2008 | Hart et al. |
| 2009/0074753 A1 | 3/2009 | Lynch |
| 2009/0092674 A1 | 4/2009 | Ingram et al. |
| 2009/0130173 A1 | 5/2009 | Behnam et al. |
| 2009/0232890 A1 | 9/2009 | Lynch et al. |
| 2010/0136085 A1 | 6/2010 | Hart et al. |
| 2010/0151025 A1 | 6/2010 | Lynch et al. |
| 2010/0174368 A1 | 7/2010 | Lynch et al. |
| 2010/0183515 A1 | 7/2010 | Hart et al. |
| 2010/0196347 A1 | 8/2010 | Kery et al. |
| 2010/0247651 A1 | 9/2010 | Kestler et al. |
| 2016/0310639 A1 | 10/2016 | Lynch |
| 2017/0014481 A1 | 1/2017 | Lynch |
| 2017/0014482 A1 | 1/2017 | Lynch |
| 2017/0014545 A1 | 1/2017 | Lynch |
| 2017/0072107 A1 | 3/2017 | Lynch |
| 2017/0072108 A1 | 3/2017 | Lynch |
| 2022/0072204 A1 | 3/2022 | Lynch |
| 2022/0176021 A1 | 6/2022 | Lynch |

FOREIGN PATENT DOCUMENTS

| | | |
|---|---|---|
| EP | 00530804 A1 | 3/1993 |
| EP | 0741785 A1 | 11/1996 |
| EP | 00896825 A1 | 2/1999 |
| EP | 00994694 A1 | 4/2000 |
| EP | 01025871 A1 | 8/2000 |
| EP | 01100488 A1 | 5/2001 |
| EP | 01146897 A1 | 10/2001 |
| EP | 01234552 A1 | 8/2002 |
| EP | 1242129 A2 | 9/2002 |
| EP | 01374857 A1 | 1/2004 |
| EP | 01410811 A1 | 4/2004 |
| EP | 1464307 A1 | 10/2004 |
| EP | 01561481 A2 | 8/2005 |
| EP | 1563846 A1 | 8/2005 |
| EP | 01681067 A1 | 7/2006 |
| EP | 1712244 A1 | 10/2006 |
| EP | 01719531 A2 | 11/2006 |
| EP | 01719532 A2 | 11/2006 |
| GB | 02367497 A | 4/2002 |
| JP | 7250688 A | 10/1995 |
| JP | 2003/265592 A | 9/2003 |
| JP | 2004159971 A | 6/2004 |
| WO | WO-88/03409 A1 | 5/1988 |
| WO | WO-91/15231 A1 | 10/1991 |
| WO | WO-91/18098 A1 | 11/1991 |
| WO | WO-92/09301 A1 | 6/1992 |
| WO | WO-92/16181 A2 | 10/1992 |
| WO | WO-93/00432 A1 | 1/1993 |
| WO | WO-93/05808 A1 | 4/1993 |
| WO | WO-93/08825 A1 | 5/1993 |
| WO | WO-93/09229 A1 | 5/1993 |
| WO | WO-93/16099 A2 | 8/1993 |
| WO | WO-93/20859 A1 | 10/1993 |
| WO | WO-94/01557 A1 | 1/1994 |
| WO | WO-94/05800 A1 | 3/1994 |
| WO | WO-94/15949 A1 | 7/1994 |
| WO | WO-94/15965 A1 | 7/1994 |
| WO | WO-94/15966 A1 | 7/1994 |
| WO | WO-94/21681 A1 | 9/1994 |
| WO | WO-94/22463 A1 | 10/1994 |
| WO | WO-94/26892 A1 | 11/1994 |
| WO | WO-94/26893 A1 | 11/1994 |
| WO | WO-94/28889 A1 | 12/1994 |
| WO | WO-95/01801 A1 | 1/1995 |
| WO | WO-95/01802 A1 | 1/1995 |
| WO | WO-95/07982 A1 | 3/1995 |
| WO | WO-95/10539 A1 | 4/1995 |
| WO | WO-95/16035 A2 | 6/1995 |
| WO | WO-95/18856 A1 | 7/1995 |
| WO | WO-95/20967 A1 | 8/1995 |
| WO | WO-95/28124 A2 | 10/1995 |
| WO | WO-95/28950 A1 | 11/1995 |
| WO | WO-96/01845 A1 | 1/1996 |
| WO | WO-96/02559 A1 | 2/1996 |
| WO | WO-96/13226 A1 | 5/1996 |
| WO | WO-96/16668 A1 | 6/1996 |
| WO | WO-96/17924 A2 | 6/1996 |
| WO | WO-97/13857 A1 | 4/1997 |
| WO | WO-98/00183 A2 | 1/1998 |
| WO | WO-98/40113 A1 | 9/1998 |
| WO | WO-98/41246 A2 | 9/1998 |
| WO | WO-98/51354 A2 | 11/1998 |
| WO | WO-99/30726 A1 | 6/1999 |
| WO | WO-99/38543 A2 | 8/1999 |
| WO | WO-99/67289 A1 | 12/1999 |
| WO | WO-00/04940 A1 | 2/2000 |
| WO | WO-01/32197 A2 | 5/2001 |
| WO | WO-01/35932 A2 | 5/2001 |
| WO | WO-01/41822 A1 | 6/2001 |
| WO | WO-01/57083 A1 | 8/2001 |
| WO | WO-01/60424 A2 | 8/2001 |
| WO | WO-01/66044 A2 | 9/2001 |
| WO | WO-01/66130 A1 | 9/2001 |
| WO | WO-01/68135 A2 | 9/2001 |
| WO | WO-02/00244 A2 | 1/2002 |
| WO | WO-02/00272 A2 | 1/2002 |
| WO | WO-02/36147 A1 | 5/2002 |
| WO | WO-02/062405 A2 | 8/2002 |
| WO | WO-02/067978 A1 | 9/2002 |
| WO | WO-02/070029 A2 | 9/2002 |
| WO | WO-02/102783 A1 | 12/2002 |
| WO | WO-03/006025 A1 | 1/2003 |
| WO | WO-03/043576 A2 | 5/2003 |
| WO | WO-03/065996 A2 | 8/2003 |
| WO | WO-03/070186 A2 | 8/2003 |
| WO | WO-03/071997 A1 | 9/2003 |
| WO | WO-2004/002539 A2 | 1/2004 |
| WO | WO-2004/010907 A1 | 2/2004 |
| WO | WO-2004/071543 A1 | 8/2004 |
| WO | WO-2004/073563 A2 | 9/2004 |
| WO | WO-2004/110308 A2 | 12/2004 |
| WO | WO-2005/009496 A1 | 2/2005 |
| WO | WO-2005/032461 A2 | 4/2005 |
| WO | WO-2005/042048 A2 | 5/2005 |
| WO | WO-2005/046746 A2 | 5/2005 |
| WO | WO-2005/054279 A1 | 6/2005 |
| WO | WO-2005/072656 A1 | 8/2005 |

(56) References Cited

FOREIGN PATENT DOCUMENTS

| | | |
|---|---|---|
| WO | WO-2006/031388 A2 | 3/2006 |
| WO | WO-2006/034365 A2 | 3/2006 |
| WO | WO-2006044334 A2 | 4/2006 |
| WO | WO-2006/050493 A2 | 5/2006 |
| WO | WO-2006/093808 A1 | 9/2006 |
| WO | WO-2006/133403 A2 | 12/2006 |
| WO | WO-2007/061889 A2 | 5/2007 |
| WO | WO-2007/087436 A2 | 8/2007 |
| WO | WO-2007/089997 A2 | 8/2007 |
| WO | WO-2007/090102 A2 | 8/2007 |
| WO | WO-2007/092622 A2 | 8/2007 |
| WO | WO-2008/005427 A2 | 1/2008 |
| WO | WO-2008/073628 A2 | 6/2008 |
| WO | WO-2008/103690 A2 | 8/2008 |
| WO | WO-2008/151193 A1 | 12/2008 |
| WO | WO-2009/100454 A1 | 8/2009 |
| WO | WO-2010/030714 A2 | 3/2010 |
| WO | WO-2010/071857 A1 | 6/2010 |
| WO | WO-2010/102266 A1 | 9/2010 |

OTHER PUBLICATIONS

Aastrom Biosciences, Inc. (Mar. 23, 2006). "Aastrom Biosciences Received Orphan Drug Designation From the FDA for Proprietary Marrow Cells," located at <http://www.aastrom.com/pressreleases.asp?GetLink=http%3A%2Fwww%2E7war- e% . . . >, lastvisited on Feb. 24, 2010, 2 pages.
Adalberto et al. "Periodontal Regeneration," J. Periodontal, 2005, 76(9):1601-1622.
Adornato, M.C. et al. (Jul. 2007). "The Treatment of Bisphosphonate-Associated Osteonecrosis of the Jaws with Bone Resection and Autologous Platelet-Derived Growth Factors," Journal of the American Dental Association 138(7):971-977. cited byapplicant.
Advisory Action Before the Filing of an Appeal Brief dated Apr. 4, 2008, for U.S. Appl. No. 11/159,533, filed Jun. 23, 2005, 3 pages.
Aghaloo, T.L. DDS MD et al., "Evaluation of Platelet-Rich Plasma in Combination with A-rganic Bovine Bone in the Rabbit Cranium: A Pilot Study," The International Journal of Oral and Maxillofacial Implants, 2004, 19:59-65.
Ahn, S-H. et al. (Jun. 2003). "Effect of Recombinant Human Bone Morphogenetic Protein-4 with Carriers in Rate Calvarial Defects," Journal of Periodontology 74(6):787-797.
Akita, S. et al. (2004). "Capillary Vessel Network Integration by Inserting a Vascular Pedicle Enhances Bone Formation in Tissue-Engineered Bone Using Interconnected Porous Hydroxyapatite Ceramics," Tissue Eng. 10(5/6):789-795.
Almojaly, S. (2008). "The Effect of Bisphosphonate, Alendronate, on Primary Human Alveolar Bone Cells," Masters Abstracts International 46(6):61.
Amendment After Request for Continued Examination dated Aug. 7, 2008, for U.S. Appl. No. 11/159,533, filed Jun. 23, 2005, 18 pages.
Amendment and Response to Final Office Action dated Feb. 25, 2008, for U.S. Appl. No. 11/159,533, filed Jun. 23, 2005, 9 pages.
Amendment and Response to Non-Final Office Action dated Oct. 26, 2007, for U.S. Appl. No. 11/159,533, filed Jun. 23, 2005, 15 pages.
Amendment in Response to Non-Final Office Action dated Dec. 18, 2009, for U.S. Appl. No. 11/704,685, filed Feb. 9, 2007, 32 pages.
Amendment in Response to Non-Final Office Action dated Jan. 14, 2011, for U.S. Appl. No. 11/601,376, filed Nov. 17, 2006, 14 pages.
Amendment in Response to Non-Final Office Action dated Jan. 14, 2011, for U.S. Appl. No. 12/368,242, filed Feb. 9, 2009, 19 pages.
Amendment in Response to Non-Final Office Action dated Oct. 6, 2010, for U.S. Appl. No. 12/323,183, filed Nov. 25, 2008, 11 pages.
American Dental Association (Jun. 2006). Expert Panel Recommendations: Dental Management of Patients on Oral Bisphosphonate Therapy, Report of the Council of Scientific Affairs, 14 pages.

Anitua et al.; "Autologous preparations rich in growth factors promote proliferation and induce VEGF and HGF production by human tendon cells in culture";Journal of Orthopaedic Research, 23 (2005) 281-286.
Anitua, E. et al., "Autologous platelets as a source of proteins for healing and tissue regeneration," Thromb Haemost, 2004, 91:4-15.
Anonymous (2003). "The European Market for Dental Bone Graft Substitutes," Implant Dentistry 12(1):3-5.
Antoniades et al. "Human platelet-derived growth factor (PDGF): amino-terminal amino acid sequence," Science, 1983, 220:963-965.
Antoniades, H.N. et al. (1985). "Platelet-Derived Growth Factor: A Link to Malignant Transformation," in Cancer Cells 3: Growth Factors and Transformations, Fermasico, J. et al. eds., Cold Spring Harbor Laboratory: Cold Spring Harbor, NY, 3:145-151.
Antoniades, H.N. et al. (1991). "Molecular Mechanism of Tissue Repair: Injury Induces Expression of PDGF-B and its Receptor," Abstract No. 2156, J. Dental Res. 70:536.
Anusaksathien et al. "Platelet-Derived Growth Factor Gene Delivery Stimulates ex Vivo Gingival Repair," Tissue Engineering, 2003, 9(4):745-758.
Anusaksathien et al., "Effect of Sustained Gene Delivery of Platelet-Derived Growth Factor or Its Antagonist (PDGF-1308) on Tissue-Engineered Cementum," J. Periodontal, 2004, 75(3): 429-440.
Anusaksathien et al., "Growth Factor Delivery to Re-Engineer Periodontal Tissues," Current Pharmaceutical Biotechnology, 2002, vol. 3(2): 129-139.
Arm, et al. Effect of Controlled Release of Platelet-derived Growth Factor from a Porous Hydroxyapatite Implant on Bone Ingrowth, Biomaterials 17 (1996) 703-709.
Assael, L.A. (2006). "A Time for Perspective on Bisphosphonates," J. Oral Maxillofac. Surg. 64:877-879.
Babbush, C.A. DDS MSCD et al., "An In Vitro and In Vivo Evaluation of Autologous Platelet Concentrate in Oral Reconstruction," Implant Dent., 2003, 12:24-34.
Barker, K. et al. (Jun. 2006). "Bisphosphonate-Associated Osteonecrosis of the Jaws: A Guide for the General Dental Practitioner," Dental Update pp. 270-275.
Basa, S. et al. (2004). "Alternative Bone Expansion Technique for Immediate Placement of Implants in the Edentulous Posterior Mandibular Ridge: A Clinical Report," International Journal of Oral & Maxofacial Implants 19(4):554-558.
Bateman, et al. Platelet-Derived Growth Factor Enhancement of Two Alloplastic Bone Matrices, J. Periodontol. (2005) 76: 1833-1841.
Becker. W. et al. (Nov. 1992). "A Comparison of PTFE Membranes Alone or in Combination with Platelet-Derived Growth Factor and Insulin-Like Growth Factor-I, or Demineralized Freeze Dried Bone in Promoting Bone Formation Around Immediate Extractionsocket Implants: A Study in Dogs," J. Periodtonol. 63(11):929-940.
Berlemann, U. et al. (2002). "Adjacent Vertebral Failure After Vertebroplasty," J. Bone Joint Surg. BR 84(B):748-752.
Betsholtz et al. "cDNA sequence and chromosomal localization of human platelet-derived growth factor A-chain and its expression in tumour cell lines," Nature, 1986, 320:695-699.
Biomimetic Therapeutics (Aug. 10, 2009). "BioMimetic Therapeutics Reports 2009 Second Quarter Earnings Results," located at <http://biomimetics.com/cgi-bin/aw/acuweb.cgi?s=biomimetics&t=pressrel- easedtl.htm&StoryID=185&>, last visited on May 18, 2010, 8 pages.
Biomimetic Therapeutics (Aug. 11, 2008). "BioMimetic Therapeutics Reports 2008 Second Quarter Results; Positive Results Achieved with Augment.TM. Injectable Bone Graft to Enhance Healing in Foot and Ankle Fusions," located at<http://biomimetics.com/cgi-bin/aw/acuweb.cgi?s=biomimetics&t=pressrel- easedtl.htm&StoryID=151&>, last visited on May 18, 2010, 8 pages.
Biomimetic Therapeutics (Aug. 14, 2007). "BioMimetic Therapeutics Reports 2007 Second Quarter Results," located at <http://biomimetics.com/cgi-bin/aw/acuweb.cgi?s=biomimetics&t=pressrel- easedtl.htm&StoryID=125&>, last visited on May 18, 2010,7 pages.
Biomimetic Therapeutics (Aug. 21, 2002). "Orthovita and BioMimetic Enter into a Supply Agreement," located at <http://biomimetics.

(56) References Cited

OTHER PUBLICATIONS com/egi-bin/aw/acuweb.cgi?s=biomimetics&t=pressrel-easedtl.htm&StoryID=82&>, last visited on May 18, 2010, 6pages.
Biomimetic Therapeutics (Dec. 11, 2008). "BioMimetic Therapeutics, Inc. Achieves Patient Enrollment Target (396) in North American Pivotal Study for Augment.TM. Bone Graft," located at<http://biomimetics.com/cgi-bin/aw/acuweb.cgi?s=biomimetics&t=pressrel-easedtl.htm&StoryID=169&>, last visited on May 18, 2010, 5 pages.
Biomimetic Therapeutics (Dec. 13, 2006). "BioMimetic Therapeutics Announces Positive Results; GEM OS1 Stimulates Bone Healing Comparable to Autograft," located at <http://biomimetics.com/cgi-bin/aw/acuweb. cgi?s=biomimetics&t=pressrel-easedtl.htm&StoryID=104&>, last visited on May 18, 2010, 7 pages.
Biomimetic Therapeutics (Dec. 13, 2007). "BioMimetic Therapeutics reports Positive Clinical Results for GEM OS.RTM. 1 in Canadian Foot and Ankle Fusion Study; Clinical Success Rate of 90% Achieved in High Risk Patient Population," located at<http://biomimetics.com/cgi-bin/aw/acuweb.cgi?s=biomimetics&t=pressrel-easedtl.htm&StoryID=131&>, last visited on May 18, 2010, 6 pages.
Biomimetic Therapeutics (Dec. 17, 2007). "BioMimetic Therapeutics to Sell Remaining Dental Business for Additional $40 Million Cash Plus Continuation of Royalties; Company to Focus on Orthopedics, Spine and Sports Medicine," located at<http://biomimetics.com/cgi-bin/aw/acuweb.cgi?s=biomimetics&t=pressrel-easedtl.htm&StoryID=149&>, last visited on May 18, 2010, 7 pages.
Biomimetic Therapeutics (Feb. 1, 2010). "BioMimetic Therapeutics, Inc. Patent Portfolio Further Strengthened" located at <http://biomimetics.com/cgi-bin/aw/acuweb.cgi?s=biomimetics&t=pressrel-easedtl.htm&StoryID=199&>, last visited on May 18, 2010, 5 pages.
Biomimetic Therapeutics (Feb. 12, 2004). "BioMimetic Pharmaceuticals Announces Additions to Senior Management Team," located at <http://biomimetics.com/cgi-bin/aw/acuweb.cgi?s=biomimetics&t=pressrel-easedtl.htm&StoryID=83&>, last visited onMay 18, 2010, 6 pages.
Biomimetic Therapeutics (Feb. 19, 2009). "BioMimetic Therapeutics, Inc. to Highlight Pre-Clinical and Clinical Activities at ORS and AAOS Meetings; Company to Host an Analyst and Investor Meeting Feb. 26," located at<http://biomimetics.com/cgi-bin/aw/acuweb.cgi?s=biomimetics&t=pressrel-easedtl.htm&StoryID=154&>, last visited on May 18, 2010, 6 pages.
Biomimetic Therapeutics (Feb. 21, 2007). "BioMimetic Therapeutics Receives Orphan Drug Designation for rhPDGF-BB Treatment of Osteonecrosis of the Jaw," located at <http://biomimetics.com/cgi-bin/aw/acuweb.cgi?s=biomimetics&t=pressrel-easedtl.htm&StoryID=112&>, last visited on Apr. 5, 2010, 6 pages.
BioMimetic Therapeutics (Feb. 29, 2008). "BioMimetic Therapeutics, Inc. to Highlight Clinical and Preclinical Activities at ORS and AAOS Meetings," located at <http://biomimetics.com/cgi-bin/aw/acuweb.cgi?s=biomimetics&t=pressrel-easedtl.htm&StoryID=136&>, last visited on May 18, 2010, 6 pages.
Biomimetic Therapeutics (Jan. 25, 2007). "BioMimetic Therapeutics Reports Positive Clinical Results Using GEM OS.RTM. 1 to Treat Distal Radius Fractures," located at <http://biomimetics.com/cgi-bin/aw/acuweb.cgi?s=biomimetics&t=pressrel-easedtl.htm&StoryID=105&>, last visited on May 18, 2010, 6 pages.
Biomimetic Therapeutics (Jan. 7, 2009). "BioMimetic Therapeutics, Inc. Closes Enrollment with 436 Patients in North American Pivotal Study for Augment.TM. Bone Graft; Company Will File Modular PMA with the FDA Beginning This Spring," located at<http://biomimetics.com/cgi-bin/aw/acuweb.cgi?s=biomimetics&t=pressrel-easedtl.htm&StoryID=168&>, last visited on May 18, 2010, 5 pages.
Biomimetic Therapeutics (Jul. 11, 2006). "BioMimetic Therapeutics Successfully Completes Enrollment in Three Orthopedic Pilot Clinical Trials for GEM OS1 .TM. Bone Graft; Canadian Study Expanded to 60 Patients," located at<http://biomimetics.com/cgi-bin/aw/acuweb.cgi?s=biomimetics&t=pressrel-easedtl.htm&StoryID=93&>, last visited on May 18, 2010, 6 pages.
Biomimetic Therapeutics (Jul. 13, 2005). "BioMimetic Pharmaceuticals Strengthens Senior Leadership Team," located at <http://biomimetics.com/cgi-bin/aw/acuweb.cgi?s=biomimetics&t=pressrel-easedtl.htm&StoryID=81&>, last visited on May 20, 2010, 6 pages.
Biomimetic Therapeutics (Jul. 13, 2007). "BioMimetic Therapeutics' Clinical Investigator Presents Positive Interim Data on U.S. and Canadian Foot and Ankle Clinical Trials," located at<http://biomimetics.com/cgi-bin/aw/acuweb.cgi?s=biomimetics&t=pressrel-easedtl.htm&StoryID=123&>, last visited on May 18, 2010, 8 pages.
Biomimetic Therapeutics (Jul. 15, 2004). "BioMimetic Pharmaceuticals' Receives Approvable Recommendation from FDA Advisory Panel for GEM 21 S.RTM.," located at <http://biomimetics.com/cgi-bin/aw/acuweb.cgi?s=biomimetics&t=pressrel-easedtl.htm&StoryID=78&>, last visited on May 18, 2010, 6 pages.
Biomimetic Therapeutics (Jun. 7, 2006). "BioMimetic Therapeutics Receives Approval to Market GEM 21 S.RTM. Growth-Factor Enhanced Matrix in Canada," located at <http://www.biomimetics.com/cgi-bin/acuweb/acuweb.cgi?s=biom&t=NewsDet-ail.htm&StoryID=166&>, 5 pages.
Biomimetic Therapeutics (Jun. 7, 2007). "BioMimetic Therapeutics Initiates Enrollment in E.U. Registration Trial for GEM OS.RTM. 1 Bone Graft; U.S. GEM OS1 Pivotal Study Protocol Amended to Allow Shorter Follow-Up Time and More Patients," located at<http://biomimetics.com/cgi-bin/aw/acuweb.cgi?s=biomimetics&t=pressrel-easedtl.htm&StoryID=119&>, last visited on May 18, 2010, 6 pages.
Biomimetic Therapeutics (Mar. 11, 2010). "BioMimetic Therapeutics Reports 2009 Fourth Quarter and Year End Earnings Results; Company Releases Additional Pivotal Data on Augment," located at<http://biomimetics.com/cgi-bin/aw/acuweb.cgi?s=biomimetics&t=pressrel-easedtl.htm&StoryID=203&>, last visited on May 18, 2010, 11 pages.
Biomimetic Therapeutics (Mar. 12, 2008). "BioMimetic Therapeutics Reports 2007 fourth Quarter and Year-End Results; Year Marked by Strong Cash Position, Positive Orthopedic Data and Progressing Clinical Trials," located at<http://biomimetics.com/cgi-bin/aw/acuweb.cgi?s=biomimetics&t=pressrel-easedtl.htm&StoryID=137&>, last visited on May 18, 2010, 8 pages.
Biomimetic Therapeutics (Mar. 12, 2009). "BioMimetic Therapeutics Reports 2008 Fourth Quarter and Year End Results," located at <http://biomimetics.com/cgi-bin/aw/acuweb.cgi?s=biomimetics&t=pressrel-easedtl.htm&StoryID=160&>, last visited onMay 18, 2010, 11 pages.
Biomimetic Therapeutics (Mar. 12, 2010). "Morningstar.RTM. Document Research.sup.SM Form 10-K," United States Securities and Exchange Commission Annual Report, located at <http://investor.biomimetics.com/phoenix.zhtml?c=196896&p=irol-sec>—, last visited on May 19, 2010, 247 pages.
Biomimetic Therapeutics (Mar. 20, 2006). "BioMimetic Therapeutics Initiates Trials with Novel Bio-Active Drug-Device Combination Bone Graft in Two Orthopedic Indications," located at<http://biomimetics.com/cgi-bin/aw/acuweb.cgi?s=biomimetics&t=pressrel-easedtl.htm&StoryID=118&>, last visited on May 18, 2010, 6 pages.
Biomimetic Therapeutics (Mar. 28, 2007). "BioMimetic Therapeutics Reports 2006 Fourth Quarter and Year-End Results; Company Receives Clearance to Initiate Enrollment in GEM OS1 US Pivotal Trial," located at<http://biomimetics.com/cgi-bin/aw/acuweb.cgi?s=biomimetics&t=pressrel-easedtl.htm&StoryID=113&>, last visited on May 18, 2010, 8 pages.
Biomimetic Therapeutics (Mar. 4, 2010). "BioMimetic Therapeutics, Inc. to Highlight Pre-Clinical and Clinical Activities at ORS and AAOS Meetings; Company to Host Analyst and Investor Meeting on Mar. 11," located at<http://biomimetics.com/cgi-bin/aw/acuweb.cgi?s=biomimetics&t=pressrel-easedtl.htm&StoryID=201&>, last visited on May 18, 2010, 6 pages.
Biomimetic Therapeutics (Mar. 7, 2008). "BioMimetic Therapeutics, Inc. Provides Updates on Clinical and Preclinical Activities; Company Receives Go Ahead from Health Canada to File GEM

(56) References Cited

OTHER PUBLICATIONS

OS1 DLA," located at<http://biomimetics.com/cgi-bin/aw/acuweb.cgi?s=biomimetics&t=pressrel- easedtl.htm&StoryID=138&>, last visited on May 18, 2010, 6 pages.

Biomimetic Therapeutics (Mar. 9, 2010). "BioMimetic Therapeutics Presents Promising Pre-Clinical Sports Medicine data at the 2010 ORS Meeting," located at <http://biomimetics.com/cgi-bin/aw/acuweb.cgi?s=biomimetics&t=pressrel-easedtl.htm&StoryID=202&>, last visited on May 18, 2010, 6 pages.

Biomimetic Therapeutics (May 10, 2007). "BioMimetic Therapeutics to Report 2007 First Quarter Financial Results on May 14," located at <http://biomimetics.com/cgi-bin/aw/acuweb.cgi?s=biomimetics&t=pressrel- easedtl.htm&StoryID=111&>, lastvisited on May 18, 2010, 4 pages.

Biomimetic Therapeutics (May 14, 2007). "BioMimetic Therapeutics Reports 2007 First Quarter Results; Company Added to NASDAQ Biotechnology Index," located at <http://biomimetics.com/cgi-bin/aw/acuweb.cgi?s=biomimetics&t=pressrel-easedtl.htm&StoryID=116&>, last visited on May 18, 2010, 7 pages.

Biomimetic Therapeutics (May 18, 2005). "BioMimetic Pharmaceuticals Raises Additional $11.8 Million in Equity Financing," located at <http://biomimetics.com/cgi-bin/aw/acuweb.cgi?s=biomimetics&t=pressrel- easedtl.htm&StoryID=80&>, last visitedon May 18, 2010, 6 pages.

Biomimetic Therapeutics (May 21, 2003). "BioMimetic Pharmaceuticals, Inc. Closes Series B Venture Funding," located at <http://biomimetics.com/cgi-bin/aw/acuweb.cgi?s=biomimetics&t=pressrel- easedtl.htm&StoryID=76&>, last visited on May 18, 2010, 5 pages.

Biomimetic Therapeutics (May 7, 2009). "BioMimetic Therapeutics Releases 2009 First Quarter Financial Results," located at <http://biomimetics.com/cgi-bin/aw/acuweb.cgi?s=biomimetics&t=pressrel- easedtl.htm&StoryID=167&>, last visited on May 18, 2010, 8 pages.

Biomimetic Therapeutics (Nov. 10, 2008). "BioMimetic Therapeutics Reports 2008 Third Quarter Results," located at <http://biomimetics.com/cgi-bin/aw/acuweb.cgi?s=biomimetics&t=pressrel- easedtl.htm&StoryID=157&>, last visited on May 18, 2010,8 pages.

Biomimetic Therapeutics (Nov. 13, 2007). "BioMimetic Therapeutics Reports 2007 Third Quarter Results," located at <http://biomimetics.com/cgi-bin/aw/acuweb.cgi?s=biomimetics&t=pressrel- easedtl.htm&StoryID=127&>, last visited on May 18, 2010,7 pages.

Biomimetic Therapeutics (Nov. 21, 2005). "BioMimetic Therapeutics Announces FDA Approval of GEM 21S.RTM. Growth-Factor Enhanced Matrix for the Treatment of Periodontally-Related Bone Defects," located at<http://biomimetics.com/cgi-bin/aw/acuweb.cgi?s=biomimetics&t=pressrel- easedtl.htm&StoryID=87&>, last visited on May 18, 2010, 6 pages.

Biomimetic Therapeutics (Nov. 21, 2008). "BioMimetic Therapeutics, Inc. Announces Patent Allowance from the United States Patent and Trademark Office for PDGF Compositions Patent; Expanded Protection for Augment.TM., Augment.TM. Injectable and GEM21S.RTM. Until 2024," located at <http://biomimetics.com/cgi-bin/aw/acuweb.cgi?s=biomimetics&t=pressrel- easedtl.htm&StoryID=163&>, last visited on May 18, 2010, 5 pages.

Biomimetic Therapeutics (Nov. 3, 2009). "BioMimetic Therapeutics Receives First Orthopedic Marketing Approval for Augment Bone Graft," located at <http://biomimetics.com/cgi-bin/aw/acuweb.cgi?s=biomimetics&t=pressrel-easedtl.htm&StoryID=190&>, last visited on May 18, 2010, 6 pages.

Biomimetic Therapeutics (Nov. 4, 2004). "BioMimetic Pharmaceuticals Raises $25.7 Million in Series C Financing," located at <http://biomimetics.com/cgi-bin/aw/acuweb.cgi?s=biomimetics&t=pressrel- easedtl.htm&StoryID=79&>, last visited on May 20, 2010, 5 pages.

Biomimetic Therapeutics (Nov. 5, 2009). "BioMimetic Therapeutics Reports 2009 Third Quarter Earnings Results; Company's Second Orthopedic Product Candidate Enters Pivotal Trial for Foot and Ankle Fusion Indications," located at<http://biomimetics.com/cgi-bin/aw/acuweb.cgi?s=biomimetics&t=pressrel- easedtl.htm&StoryID=191&>, last visited on May 18, 2010, 8 pages.

Biomimetic Therapeutics (Nov. 6, 2006). "BioMimetic Therapeutics' Clinical Investigator Highlights Results of Orthopedic Clinical Trial Canada," located at <http://biomimetics.com/cgi-bin/aw/acuweb.cgi?s=biomimetics&t=pressrel-easedtl.htm&StoryID=101&>, last visited on May 18, 2010, 7 pages.

Biomimetic Therapeutics (Oct. 13, 2009). "BioMimetic Announces Positive Top-Line Data from its Augment Bone Graft North American Pivotal Trial; Augment Demonstrates Non-Inferiority to Autograft," located at<http://biomimetics.com/cgi-bin/aw/acuweb.cgi?s=biomimetics&t=pressrel- easedtl.htm&StoryID=188&>, last visited on May 18, 2010, 8 pages.

Biomimetic Therapeutics (Oct. 29, 2008). "BioMimetic Therapeutics Reports Promising Clinical Results Using Augment Injectable Bone Graft to Treat Distal Radius Fractures; Enrollment in North American Augment Pivotal Trial Accelerates; 314 of 396Patients Enrolled," located at <http://biomimetics.com/cgi-bin/aw/acuweb.cgi?s=biomimetics&t=pressrel-easedtl.htm&StoryID=159&>, last visited on May 18, 2010, 6 pages.

Biomimetic Therapeutics (Sep. 14, 2006). "BioMimetic Therapeutics' Clinical Investigators to Receive Award from American Academy of Periodontolgy for Outstanding Publication; Clinical Investigators to Present Data at Annual AAP Meeting," located at<http://biomimetics.com/cgi-bin/aw/acuweb.cgi?s=biomimetics&t=pressrel- easedtl.htm&StoryID=94&>, last visited on May 18, 2010, 6 pages.

Biomimetic Therapeutics (Sep. 23, 2008). "BioMimetic Therapeutics Announces No Changes Requested by Independent Data Monitoring Committee to Pivotal Trial Design for Augment.TM. Bone Graft; 268 of 396 Patients Enrolled to Date in U.S. PivotalTrial," located at <http://biomimetics.com/cgi-bin/aw/acuweb.cgi?s=biomimetics&t=pressrel-easedtl.htm&StoryID=153&>, last visited on May 18, 2010, 7 pages.

Biomimetic Therapeutics (Sep. 27, 2006). "BioMimetic Therapeutics Adds Key Talent to Board of Directors," located at <http://biomimetics.com/cgi-bin/aw/acuweb.cgi?s=biomimetics&t=pressrel- easedtl.htm&StoryID=97&>, last visited on May 20, 2010, 6 pages.

Bjorkenheim, J.M. (1989). "Structure and Function of the Rabbit's Supraspinatus Muscle After Resection of its Tendon," Acta Orthop. Scand. 60(4):461-463.

BMP Gene Delivery for Alveolar Bone Engineering at Dental Implant Defects—Molecular Therapy, vol. 11,-., Feb. 2, 2005.

Boileau, P. et al. (Jun. 2005). "Arthroscopic Repair of Full-Thickness Tears of the Supraspinatus: Does the Tendon Really Heal?" J. Bone Joint Surg. Am. 87-A(6):1229-1240.

Bolander, "Regulation of Fracture Repair by Growth Factors," P.S.E.B.M., 1992, 200: 165-170.

Bonfini, T. et al. (Jan. 1, 2006). "Autologous Marrow and Platel Gel in Bone Tissue Regeneration," Cytotherapy 8(1), Abstract No. 239, 2 pages.

Bora, F.W. Jr. et al. (Aug. 1987). "Joint Physiology, Cartilage Metabolism, and the Etiology of Osteoarthritis," Hand Clin. 3(3):325-336.

Boyden, E.M. et al. (Aug. 1995). "Late Versus Early Repair of Achilles Tendon Rupture: Clinical and Biomechanical Evaluation," Clin. Orthop. Relat. Res. 317:150-158.

Braddock, M. et al. (Oct. 2001). "Born Again Bone: Tissue Engineering for Bone Repair," News Physiool. Sci. 16:208-213.

Buser, D. et al. (1991). "Effects of Growth Factors on Bone Regeneration Around Titanium Implants," Abstract No. 282, J. Dental Res. 70:301.

Business Wire (May 29, 2002). "Orthovita Issued Patent for Biomaterials Platform Designed to Facilitate Natural Mechanism of Action in Bone Healing," located at <http://www.highbeam.com/doc/1G1-86413645.html>, last visited on Jun. 17, 2010, 3pages.

Business Wire. (Dec. 15, 2000). "Orthovita Recieves U.S. FDA Clearance for VITOSS Scaffold, the First Engineered 90% Porous Beta-Tricalcium Phosphate; Another Milestone Achievement This Year for Orthovita," located at<http://www.highbeam.com/doc/1G1-68027113.html>, last visited on Apr. 26, 2010, 3 pages.

(56) References Cited

OTHER PUBLICATIONS

Camargo, et al., "Platelet-rich plasma and bovine porous bone mineral combined with guided tissue regeneration in the treatment of intrabony defects in humans," J Periodont Res 2002, 37: 300-306.
Camargo, L.V. PM et al., "Effectiveness of a combination of platelet-rich plasma, bovine porous bone mineral and guided tissue regeneration in the treatment of mandibular grade II molar furcations in humans," J. Clin. Periodontol, 2003, 30:746-751.
Camelo et al., "Clinical, radiographic, and histologic evaluation of human periodontal defects treated with bio-oss and bio-guide," International Journal of Periodontics and Restorative Dentistry, 1998, 18(4): 321-332.
Camelo et al., "Periodontal regeneration with an autoge-us bone-bio-oss composite graft and a bio-guide membrane," International Journal of Periodontics and Restorative Dentistry. 2001, 21(2): 109-120.
Camelo, M. et al. (2003). "Periodontal Regeneration in Human Class II Furcations Using Purified Recombinant Human Platelet-Derived Growth Factor-BB (rhPDGF-BB) with Bone Allograft," International Journal of Periodontics & Restorative Dentistry23(3):213-225.
Canalis, "Effect of Growth Factors on Bone Cell Replication and Differentiation," Clinical Orthopedics and Related Research, 1985, 193: 246-263.
Carpio, L. et al. (Nov. 2000). "Guided Bone Regeneration Around Endosseous Implants with Anorganic Bovine Bone Material. A Randomized Controlled Trial Comparing Bioabsorbable Versus Non-Resorbable Barriers," J. Periodontol. 71(1):1743-1749. cited byapplicant.
Catalano, L. et al. (2006). "Bisphoshonates and Risk of Osteonecorisis of the Jaws," Haema 9(3):410-414.
Cenni, E. et al. (2003, e-pub. Oct. 1, 2003). "Plasma Levels of Coagulation Inhibitors, Fibrinolytic Markers and Platelet-Derived Growth Factor-AB in Patients with Failed Hip Prosthesis," Acta Orthop. Scand. 74(5):559-564.
Cenni, E. et al. (2005, e-pub. Feb. 1, 2005). "Plasma Levels of Platelet-Derived Growth Factor BB and Transforming Growth Factor in Patients with Failed Hip Protheses," Acta Orthopaedica 76(1):64-66.
Chalmers, J. (Jun. 2000). "Review Article: Treatment of Achilles Tendon Ruptures," J. Orthop. Surg. 8(1):97-99.
Chan, B.P. et al. (Jul. 2006). "Supplementation-time Dependence of Growth Factors in Promoting Tendon Healing," Clinical Orthopaedics and Related Research 448:240-247.
Chen et al., "Ade-viral Gene Transfer of PDGF Downregulates Gas Gene Product PDGFR and Prolongs ERK and Akt/PKB Activation," Am J Physiol Cell Physiol 282: C538-C544, 2002.
Chiandussi, S. et al. (2006). "Clinical and Diagnostic Imaging of Bisphosphonate-Associated Osteonecrosis of the Jaws," Dentomaxillofacial Radiology 35:236-243.
Chin, M. (1995). "Distraction Osteogenesis in Maxillofacial Surgery," Chapter 9 in Tissue Engineering: Applications in Maxillofacial Surgery and Periodontics, Lynch, S.E et al. eds., Quintessence Publishing, pp. 147-159.
Cho et al., "Platelet-derived Growth Factor-Modulated Guided Tissue Regenerative Therapy," J Periodontal, 1995, 66(6): 522-530.
Clain, M.R. et al. (Oct. 1992). "Achilles Tendinitis," Foot & Ankle 13(8):482-487.
Clergeau et al. "Healing Response to Anorganic Bone Implantation in Periodontal Intrabony Defects in Dogs Parti. Bone Regeneration. A Microradiographic Study," J.Periodontool., 1996, 67:140-149.
Cochran, et al. "Effects of Platelet-Derived Growth Factor Isoforms on Calcium Release From Neonatal Mouse Calvariae," Bone, 1993, 14: 53-58.
Coleman, S.H. et al. (Dec. 2003). "Chronic Rotator Cuff Injury and Repair Model in Sheep," The Journal of Bone and Joint Surgery 85-A(12):2391-2402.
Collins et al. "Cultured human endothelial cells express platelet-derived growth factor B chain: cDNA cloning and structural analysis," Nature, 1985, 318:748-750.

Convery, F.R. et al. (Jan.-Feb. 1972). "The Repair of Large Osteochondral Defects. An Experimental Study in Horses," Clin. Orthop. Relat. Res. 82:253-262.
Cooke et al., "Effect of rhPDGR-BB Delivery on Mediators of Periodontal Wound Repair," Tissue Engineering, 2006, 12(6): 1441-1450.
Cossolin, G.S.I. et al. (Date Unknown) "Treatment of Avascular Osteonecrosis of the Jaws in Cancer Patients with a Histroy of Bisphosphonate Therapy by Combining Bone Resection and Autologous Platelet-Rich Plasma," Hospital Santa Catarina 10 pages.
Costa, M.A. et al. (Jul. 2006). "Tissue Engineering of Flexor Tendons: Optimization of Tenocyte Proliferation Using Growth Factor Supplementation," Tissue Eng. 12(7):1937-1943.
Courneya, J-P. et al. (2010). "Normal and Diseased Primary Human Tenocytes in Response to rhPDGF-BB," Poster No. 1118, 56.sup.th Annual Meeting of the Orhopaedic Research Society, located at <http://www.ors.org/web/Transactions/56/1118.pdf>,last visited on Feb. 23, 2010, 1 page.
Creaney, L. et al. (May 2008, e-pub. Nov. 5, 2007). "Growth Factor Delivery Methods in the Management of Sports Injuries: The State of Play," Br. J. Sports Med. 42(5):314-320, Abstract Only.
Curt et al. (Jan. 19, 2007). "Treatment of Avascular Osteonecorsis of the Mandible in Cancer Patients with a History of Bisphosphonate Therapy by Combining Bone Resection and Autologous Platelet-Rich Plasma: Report of 3 Cases," Journal of Oral andMaxillofacial Surgery 65(2):349-355.
Dalla-Favera. "Chromosomal localization of the human homolog (c-sis) of the simian sarcoma virus one gene," Science, 1982, Science, 218:686-688.
Daniels, T.R. et al. (2008). "Application of rhPDGF-BB in Foot and Ankle Fusion Procedures," Chapter 19 in Tissue Engineering: Applications in Maxillofacial Surgery and Periodontics, Second Edition, Lynch, S.E. et al. eds., Quintessence PublishingCo.: Hanover Park, IL, pp. 267-275.
Dines J.S. et al. (Sep./Oct. 2007). "Tissue Engineering and Rotator Cuff Tendon Healing," J. Shoulder Elbow Surg. 16(55):204S-207S.
Dines, J.S. et al. (Sep./Oct. 2007). "The Effect of Growth on Differentiation Factor-5-Coated Sutures on Tendon Repair in a Rat Model," J. Shoulder Elbow Surg. 16(5S):215S-221S.
Donnelly, B.P. et al. (Jul. 2006). "Nucleotide Structure of Equine Platelet-Derived Growth Factor-A and -B and Expression in Horses with Induced Acute Tendinitis," Am. J. Vet. Res. 67(7):1218-1225, Abstract Only.
Doolittle et al. "Simian sarcoma virus one gene v-sis, is derived from the gene (or genes) encoding a platelet-derived growth factor," Science, 1982, 221:275-277.
Duffy et al.; "Growth Factors and Canine Flexor Tendon Healing: Initial Studies in Uninjured and Repair Models"; The Journal of Hand Surgery; vol. 20A, No. 4, Jul. 1995, pp. 645-649.
Dunn, C.A. et al. (Feb. 2005, e-pub. Nov. 6, 2004). "BMP Gene Delivery for Alveolar Bone Engineering at Dental Implant Defects," Molecular Therapy 11(2):294-299.
Easley, M.E. et al. (May 2000). "Isolated Subtalar Arthodesis," JBJS 82-A(5):613-624.
Eastell, R. et al. (Mar. 1991). "Classification of Vertebral Fractures," J. Bone Miner. Res. 6(3):207-215.
Erikson, A. et al. (Nov. 5, 1991). "Induction of Platelet-Derived Growth Factor .alpha.- and .beta.-Receptor mRNA and Protein by Platelet Derived Growth Factor BB," J. Biol. Chem. 266(31):21138-21144.
Extended European Search Report dated Feb. 28, 2011, for EP Patent Application No. 1152879.0, filed on Oct. 10, 2006, 6 pages.
Extended European Search Report dated Jul. 26, 2010, for EP Patent Application No. 10166327.6, filed on Oct. 10, 2005, 6 pages.
Extended European Search Report dated Mar. 2, 2011, for EP Patent Application No. 11152889.9, filed on Oct. 10, 2006, 6 pages.
Fagan, M.C. et al. (2008). "Simultaneous Augmentation of Hard and Soft Tissues for Implant Site Preparation Using Recombinant Human Platelet-Derived Growth Factor: A Human Case Report," Int. J. Periodontics Restorative Dent. 28(1):37-43.
Farrugia, M.C. et al. (Jan. 2006). "Osteonecrosis of the Mandible or Maxilla Associated with the Use of New Generation Bisphosphonates," The Laryngoscope 116:115-120.

(56) References Cited

OTHER PUBLICATIONS

Feldman, D. et al. (Sep. 1998). "In a Time of Change, Orthopedics Sector is Marked by New Modalities," The BBI Newsletter, located at <http://findarticles.com/p/articles/mi.sub.—m3570/is.sub.—n9.sub.—v—21/ai.sub.—n27541529>, last visited on Mar. 12, 2009, 2 pages.

Fennis, et al, "Mandibular reconstruction: A clinical and radiographic animal study on the use of autoge-us scaffolds and platelet-rich plasma," Int. J. Oral Maxillofac. Surg., 2001, 31:281-286.

Fennis, et al, "Mandibular reconstruction: a histological and histomorphometric study on the use of autoge-us scaffolds, particulate cortico-cancellous bone grafts and platelet rich plasma in goats," Int. J. Oral Maxillofac. Surg., 2004, 33: 48-55.

Ficarra, G. et al. (2005). "Osteonecrosis of the Jaws in Periodontal Patients with a History of Bisphophonates Treatment," J. Clin. Periodontol. 32:1123-1128.

Final Office Action dated Feb. 2, 2008, for U.S. Appl. No. 11/159,533, filed Jun. 23, 2005, 8 pages.

Final Office Action dated Jan. 7, 2011, for U.S. Appl. No. 12/323,183, filed Nov. 25, 2008, 9 pages.

Finkelman, R.D. et al. (1995). "Systematic PDGF .+-. Alendronate Increases Bone Density in OVX Rats," Abstract No. 1281, J. Dental Res. 74:172.

Fontana, et al, "Effect of Platelet-Rich Plasma on the Peri-implant Bone Response: An Experimental Study," Implant Dentistry, 2004, 13: 73-78.

Franco, B. et al. (Jan.-Jun. 2008). "Tissue Engineering Approaches for the Construction of a Completely Autologous Tendon Substitute," Indian J. Plast. Surg. 41(1):38-46, 13 pages.

Freedonia (Sep. 2006). "Biocompatible Materials. US Industry Study with Forecasts to 2010 & 2015," Study #2111, located at <http://www.freedoniagroup.com/pdf/2111smwe.pdf>, last visited on Jun. 17, 2010, 8 pages (Table of Contents Only.).

Fribourg, D. et al. (Oct. 15, 2004). "Incidence of Subsequent Vertebral Fracture After Kyphoplasty," Spine 29(20):2270-2276.

Fukui et al. "Isolation and characterization of Xenopus activin and follistatin," Devel. Biol., 1993, 159:131-139.

Galatz, L.M. et al. (Feb. 2004). "The Outcome and Repair Integrity of Completely Arthoscopically Repaired Large and Massive Rotator Cuff Tears," J. Bone Joint Surg. Am. 86-A(2):219-244.

Gamradt, S.C. et al. (Mar. 2007). "Platelet Rich Plasma in Rotator Cuff Repair," Tech, in Orthop. 22(1):26-33.

Garg, "The Use of Platelet-Rich Plasma to Enhance the Success of Bone Grafts Around Dental Implants," Dental Implantology Update, 2000, 11(3): 41-44.

Garg, A.K. (1995). "Grafting Materials in Repair and Restoration," Chapter 5 in Tissue Engineering: Applications in Maxillofacial Surgery and Periodontics, Lynch, S.E. et al. eds., Quintessence Publishing, pp. 83-101.

Gazielly, D.F. et al. (Jul. 1994). "Functional and Anatomical Results After Rotator Cuff Repair," Clin. Orthop. Relat. Res. 304:43-53.

Gelberman, R.H. et al. (Mar. 2007). "The Early Effects of Sustained Platelet-Derived Growth Factor Administration on the Functional and Structural Properties of Repaired Intrasynovial Flexor Tendons: An in vivo Biomechanic Study at 3 Weeks in Canines," J. Hand Surg. Am. 32(3):373-379.

Gerber, C. et al. (Apr. 2000). "The Results of Repair of Massive Tears of the Rotator Cuff," J. Bone Joint Surg. Am. 82-A(4):505-515.

Gerber, C. et al. (May 1994). "Mechanical Strength of Repairs of the Rotator Cuff," J. Bone Joint Surg. Br. 76-B(3):371-380.

Giannobile et al., "-n-Coordinate Control of Bone Formation Displayed by Growth Factor Combinations with IGF-I," J Dent Res, 1997, 76(9): 1569-1578.

Giannobile et al., "Comparison of Canine and -n-Human Primate Animal Models for Periodontal Regenerative Therapy: Results Following a Single Administration of PDGF/IGF-I.," J. Periodontol 1994, 65: 1158-1168.

Giannobile et al., "Periodontal Tissue Engineering by Growth Factors," Bone, 1996, 19, Supplement: 23S-37S.

Giannobile et al., "Recombinant Human Osteogenic Protein-1 (OP-1) Stimulates Periodontal Wound Healing in Class III Furcation Defects," J Periodontol, 1998, 69:129-137.

Giannobile, "Platelet-Derived Growth Factor (PDGF) Gene Delivery for Application in Periodontal Tissue Engineering," J Periodontol, 2001, 72: 815-823.

Giannobile, W.V. (2008). "Advances in Gene Therapy for Periodontal Bioengineering," Chapter 3 in Tissue Engineering: Applications in Maxillofacial Surgery and Periodontics, Second Edition, Lynch, S.E. et al. eds., Quintessence Publishing Co.:Hanover Park, IL, pp. 37-46.

Giannobile, W.V. et al. (1994). "Platelet Derived Growth Factor (PDGF) and Insulin-Like Growth Factor (IGF-I) Enhances Periodontal Regeneration in Macaca Fascicularis," Abstract No. 28, Tissue Repair 9(3 Suppl.):29.

Giannobile, W.V. et al. (1994). "Synergistic Effects of Insulin-Like Growth Factors-I (IGF-I) with Other Growth Factors on Bone Formation in vitro," Abstract No. 831, J. Dental Res. 73:205.

Giannobile, W.V. et al. (Jul. 1996). "Comparative Effects of Platelet-Derived Growth Factor and Insulin-Like Growth Factor-I, Individually and in Combination, on Periodontal Regeneration in Macaca fascicularis," J. Periodontal Res. 31(5):301-312.

Giddings, V.L. et al. (2000). "Calcaneal Loading During Walking and Running," Med. Sci. Sports Exerc. 32(3):627-634.

Gilbertson et al., "Platelet-derived Growth Factor C (PDGF-C), a-vel Growth Factor That Binds to PDGF a and b Receptor," The Journal of Biological Chemistry, 2001, 276(29): 27406-27414.

Goutalier, D. et al. (Jul. 1994). "Fatty Muscle Degeneration in Cuff Ruptures: Pre- and Postoperative Evaluation by CT Scan," Clin. Orthop. 304:78-83.

Grageda, "Platelet-Rich Plasma and Bone Graft Materials: A Review and a Standardized Research Protocol," Implant Dentistry, 2004, 13(4): 301-309.

Green et al., "Immunolocalization of platelet-derived growth factor A and B chains and PDGF-and receptors in human gingival wounds," Journal of Periodontal Research, 1997, 32(2): 209-214.

Gronwald et al., "Cloning and expression of a cDNA coding for the human platelet-derived growth factor receptor: Evidence for more than one receptor class," Proc. Natl. Acad. Sci. USA, 1988, 85:3435-3439.

Hanel, D.P. et al. (Jan. 2002). "Wrist Fractures," Orthop. Clin. North Am. 33(1):35-57.

Harryman, D.T. et al. (Aug. 1991). "Repairs of the Rotator Cuff," J. Bone Joint Surg. Am. 73-A(7):982-989.

Hart et al., "Purification of PDGF-AB and PDGF-BB from Human Platelet Extracts and Identification of All Three PDGF Dimers in Human Platelets," Biochemistry, 1990, 29: 166-172.

Hart et al., "Synthesis, Phosphorylation, and Degredation of Multiple Forms of the Platelet-derived Growth Factor Receptor Studied Using a Mo-clonal Antibody," The Journal of Biological Chemistry, 1987, 262(22): 10780-10785.

Hart et al., "Two Classes of PDGF Receptor Recognize Different Isoforms of PDGF," Science, 1988, 240:1529-1531.

Hattrup, S.J. et al. (1985). "A Review of Ruptures of the Achilles Tendon," Foot & Ankle 6(1):34-38.

Hee, HT et al., "Do autologous growth factors enhance transforaminal lumbar interbody fusion?", Eur. Spine J., 12(4):400-407, 2003.

Heini et al. (2001). Eur. Spine J. 10:S205-S213.

Helm et al., "Bone graft substitutes for the promotion of spinal arthrodesis", Neurosurg. Focus, 10(4):E4, 2001.

Hess, G.W. (Feb. 2010). "Achilles Tendon Rupture: A Review of the Etiology, Population, Anatomy, Risk Factors, and Injury Prevention," Foot Ankle Spec. 3(1):29-32.

Higashi, T. et al. (Jun. 1996). "Influence of Particle Size of Calcium Phosphate Ceramics as a Capping Agent on the Formation of a Hard Tissue Barrier in Amputated Dental Pulp," Journal of Endodontics 22(6):281-283.

Hildebrand, K.A. et al. (1998). "The Effects of Platelet-Derived Growth Factor-BB on Healing of the Rabbit Medial Collateral Ligament. An In Vivo Study," American Journal of Sports Medicine 26(4):549-554.

(56) References Cited

OTHER PUBLICATIONS

Hoffmann, A. et al. (Dec. 2007, e-pub. Jul. 19, 2007). "Tendon and Ligament Engineering in the Adult Organism: Mesenchymal Stem Cells and Gene-Therapeutic Approaches," Int. Orthop. 31(6):791-797.
Hollinger, J.O. et al. (2008). "Protein Therapeutics and Bone Healing," Chapter 1 in Tissue Engineering: Applications in Maxillofacial Surgery and Periodontics, Second Edition, Lynch, S.E. et al. eds., Quintessence Publishing Co.: Hanover Park, IL,pp. 3-25.
Hollinger, J.O. et al. (2008). "Therapeutic Opportunities for Bone Grafting," Chapter 68 in Principles of Regenerative Medicine, Atala, A. et al. eds., Academic Press: Burlington, MA, pp. 1164-1175.
Hollinger, J.O. et al. (Feb. 2008). "Recombinant Human Platelet Derived Growth Factor: Biology and Clinical Applications," J. Bone & Joint Surgery 90-A(Suppl. 1):48-54.
Hollinger, J.O. et al. (Jan. 2008, e-pub. Aug. 3, 2007). "Accelerated Fracture Healing in the Geriatric Osteoporotic Rat with Recombinant Human Platelet-Derived Growth Factor-BB and an Injectable Beta-Tricalcium Phosphate/Collagen Matrix," J.Orthopedic Res. 26:83-90.
Hollinger, J.O. et al., "Therapeutic Opportunities for Bone Grafting," Mar. 5, 2006.
Hossain, M.Z. et al. (Jul. 1996). "Biological Responses of Autogenous Bone and Beta-Tricalcium Phosphate Ceramics Transplanted into Bone Defects to Orthodontic Forces," Cleft Palate-Craniofacial Journal 33(4):277-283.
Howell et al.. "A Phase I/II Clinical Trial to Evaluate a Combination of Recombinant Human Platelet-Derived Growth Factor-BB and Recombinant Human Insulin-Like Growth Factor-I in Patients with Period. Dis.," J. Periodontol., 1997, 68(12): 1186-1193.
Howell et al.; "Polypeptide growth factors for periodontal regeneration"; Current Opinion in Periodontology 1996, 3:149-156.
Howes et al., "Platelet-Derived Growth Factor Enhances Demineralized Bone Matrix-Induced Cartilage and Bone Formation," Calcif Tissue Int., 1988, 42: 34-38.
Hsu, MD. et al., "Clinical Implications of Growth Factors in Flexor Tendon Wound Healing," The Journal of Hand Surgery, 2004, 29(4): 551-563.
Huang et al., "Ceramic biomaterials for tissue engineering," in Tissue Engineering Using Ceramics and Polymers (Second Edition) pp. 3-34 (2014). (see abstract).
Ignnotz, R.A. et al. (Mar. 25, 1986). "Transforming Growth Factor-.beta. Simulates the Expression of Fibronectin and Collagen and Their Incorporation in the Extracellular Matrix," J. Biol.Chem.261 (9)A337-4345.
Ikezawa et al., "Characterization of Cementum Derived Growth Factor as an Insulin-Like Growth Factor-I Like Molecule," Connective Tissue Research, 1997, 36(4): 309-319.
Inglis, AE. et al. (Oct. 1976). "Ruptures of the Tendo Achilles: An Objective Assessment of Surgical and Non-Surgical Treatment," J. Bone Joint Surg. 58A(7):990-993.
International Search Report dated Apr. 27, 2010, for PCT Patent Application No. PCT/US2010/026450, filed on Mar. 5, 2010, 1 page.
International Search Report dated Aug. 3, 2007, for PCT Application No. PCT/US2007/003582, filed on Feb. 9, 2007, 2 pages.
International Search Report dated Aug. 4, 2008 for PCT Patent Application No. PCT/US2008/065666, filed on Jun. 3, 2008, 3 pages.
International Search Report dated Dec. 7, 2007, for PCT Application No. PCT/US2006/044766, filed on Nov. 17, 2006, 4 pages.
International Search Report dated Jul. 8, 2009, for PCT Application No. PCT/US2008/054354, filed on Feb. 20, 2008, 8 pages.
International Search Report dated Jun. 26, 2009, for PCT Application No. PCT/US2009/033596, filed on Feb. 9, 2009, 6 pages.
International Search Report dated May 20, 2009, for PCT Application No. PCT/US2007/083638, filed on Nov. 5, 2007, 5 pages.
International Search Report dated Oct. 2, 2007, for PCT Application No. PCT/US05/36447, filed on Oct. 12, 2005, 1 page.
Ito, Y. et al. (2004, e-pub. Mar. 26, 2004). "Bone Formation Using Novel Interconnected Porous Calcium Hydroxyapatite Ceramic Hybridized with Cultured Marrow Stromal Stem Cells Derived From Green Rat," J. Biomed. Mater. Res. 69A:454-461. cited byapplicant.
Jensen et al., "Platelet rich plasma and fresh frozen bone allograft as enhancement of implant fixation—An experimental study in dogs," Journal of Orthopaedic Research, 2004, 22: 653-658.
Jensen, O.T. (2008). "Dentoalveolar Modification with an Osteoperiosteal Flap and rhPDGF-BB," Chapter 15 in Tissue Engineering: Applications in Maxillofacial Surgery and Periodontics, Second Edition, Lynch, S.E. et al. eds., Quintessence PublishingCo.: Hanover Park, IL, pp. 220-225.
Jensen, O.T. et al. (2008). "Alveolar Distraction Osteogenesis and Tissue Engineering," Chapter 14 in Tissue Engineering: Applications in Maxillofacial Surgery and Periodontics, Second Edition, Lynch, S.E. et al. eds., Quintessence Publishing Co.:Hanover Park, IL, pp. 203-219.
Jiang et al., "Modification of an Osteoconductive A-rganic Bovine Bone Mieral Matrix with Growth Factors," J. Periodontol., 1999, 70(8): 834-839.
Jin et al., "Engineering of Tooth-Supporting Structures by Delivery of PDGF Gene Therapy Vectors," Molecular Therapy, 2004, 9: 519-526.
Jin, Q. et al. (Mar. 5, 2008). "Nanofibrous Scaffolds Incorporating PDGF-BB Microspheres Induce Chemokine Expression and Tissue Neogenesis In Vivo," PLoS One 3(3):e1729, pp. 1-9.
Jones et al. "Isolation of Vgr-2, a novel member of the transforming growth factor—beta-related gene family," Mot Endocnnol., 1992, 6:1981-1968.
Jozsa, L. et al. (Aug. 1989). "Fibronectin and Laminin in Achilles Tendon," Acta Orthop Sacninavica 60(4):469-471.
Kademani, D. et al. (Aug. 2006). "Primary Surgical Therapy for Osteonecrosis of the Jaw Secondary to Bisphosphonate Therapy," Mayo Clin. Proc. 81 (8):1100-1103.
Kaigler, "Growth factor delivery for oral and periodontal tissue engineering," Expert Opin Drug Deliv., 2006, 3(5): 1742-5247.
Kapu ci ski, P. et al. (Jul.-Sep. 1996). "An Analgesic Effect of Synthetic Human Calcitonin in Patients with Primary Osteoporosis," The Polish Journal of Medicine and Pharmacy 28(98):83-86.
Kassolis et al., "Alveolar Ridge and Sinus Augmentation Utilizing Platelet-Rich Plasma in Combination with Freeze-Dried Bone Allograft: Case Series," Journal of Periodontology, 2000, 71(10):1654-1661.
Kazlauskas et al. "Different effects of homo- and heterodimers of platelet-derived growth factor A and 8 chains on human and mouse fibroblasts," The EMBO Journal (1988) 7 (12):3727-3735.
Kim et al., "A Comparative Study of Osseointegration of Avana Implants in a Demineralized Freeze-Dried Bone Alone or With Platelet-Rich Plasma," J Oral Maxillofac Surg, 2002, 60:1018-1025.
Kim et al., "Use of Particulate Dentin-Plaster of Paris Combination with/without Platelet-Rich Plasma in the Treatment of Bone Defects Around Implants," The International Journal of Oral & Maxillofacial Implants, 2002; 17:86-94.
Klotzbuecher, C.M. et al. (Apr. 2000). "Patients with Prior Fractures Have an Increased Risk of Future Fractures: A Summary of the Literature and Statistical Synthesis," J. Bone Miner. Res. 15(4):721-739.
Kobayashi, M. et al. (May/Jun. 2006). "Expression of Growth Factors in Early Phase of Supraspinatus Tendon Healing in Rabbits," J. Shoulder Elbow Surg. 15(3):371-377.
Kovacevic, D. et al. (Mar. 2008). "Biological Augmentation of Rotator Cuff Tendon Repair," Clin. Orthop. Relat. Res. 466(3):622-633.
Kovacs et al, "Comparative Study of b-Tricalcium Phosphate Mixed with Platelet-Rich Plasma versus b-Tricalcium Phosphate, A Bone Substitute Material in Dentistry," Acta Veterinaria Hungarica, 2003, 51(4):475-484.
Landesberg et al, "Quantification of Growth Factor Levels Using a Simplified Method of Platelet-Rich Plasma Gel Preparation," J. Oral Maxillofac Surg, 2000, 58: 297-300.
Lasa et al, "Chapter 14: Bone Induction by Demineralized Bone Powder and Partially Purified Osteogenin Using a Fibrin-Sealant Carrier," Surgical Adhesives and Sealants: Current Technology and

(56) References Cited

OTHER PUBLICATIONS

Applications, Edited by David H. Sierra and Renato Saltz,Technomic Publishing Co., Inc., 1996, pp. 135-143.

Lasa et al, "Delivery of Demineralized Bone Powder by Fibrin Sealant," Plast. Reconstr. Surg., 1995, 96: 1409.

Lee et al., "Enhanced bone formation by controlled growth factor delivery from chitosan-based biomaterials," Journal of Controlled Release, 2002, 78: 187-197.

Lee, S.J. et al. (2001, e-pub. Feb. 13, 2001). "Molded Porous Poly (.sub.L-Lactide) Membranes for Guided Bone Regeneration with Enhanced Effects by Controlled Growth Factor Release," Journal of Biomedical Materials Research 55:295-303. cited byapplicant.

Lee, Y-M. et al. (Mar. 2000). "The Bone Regenerative Effect of Platelet-Derived Growth Factor-BB Delivered With a Chitosan/ Tricalcium Phosphate Sponge Carrier," J. Periodontal. 71 (3):418-424.

Lekovic, et al, "Comparison of Platelet-Rich Plasma, Bovine Porous Bone Mineral, and Guided Tissue Regeneration Versus Platelet-Rich Plasma and Bovine Porous Bone Mineral in the Treatment of Intrabony Defects: A Reentry Study," J Periodontol, 2002;73(2):198-205.

Letson, A.K. et al. (1994). "The Effect of Combinations of Growth Factors on Ligament Healing," Clinical Orhopaedics and Related Research 308:207-212.

Li, J. et al. (1994). "Systematic Administration of PDGF With or Without Alendronate Increases Spine and Whole Body Bone Mineral Density in OVX Rats," Abstract No. 59, Sixteenth Annual Meeting of the American Society for Bone and Mineral Research,Kansas City, MO., Sep. 9-13, 1994, p. S135.

Liang et al.; "Effect of cytokines on repair of tendon injury"; PubMed; Sep. 2000; 14(5):283-5.

Liang, H.W. et al. (Aug. 2009). "Effect of Platelet-Derived Growth Factor-BB on Proliferation of Tendon Cells Cultured in vitro," Zhonghua Shao Shang Za Zhi 25(4):298-300, Abstract Only.

Lind et al. "Growth Factor Stimulation of Bone Healing," Acta orthopaedica Scandinavica Supplementum, 1998, 283:2-37.

Lioubavina-Hack et al., "Effect of Bio-Oss with or without platelet-derived growth factor on bone formation by 'guided tissue regeneration': a pilot study in rats," J Clin. Periodontol, 2003, 32: 1254-1260.

Lioubavina-Hack et al., "Methyl cellulose gel obstructed bone formation by GBR: an experimental study in rats," J. Clin. Periodontol., 2005, 32: 1247-1253.

Lipshitz, H. et al. (Jun. 1975). "In Vitro Wear of Cartilage," J. Bone Joint Surg. Am. 57A(4):527-534.

Lynch, et al., "A New Era in Periodontal and Periimplant Regeneration: Use of Growth-Factor Enhanced Matrices Incorporating rhPDGF", Compendium of Continuing Education in Dentistry, 27(12): pp. 672-678, 2006.

Lynch, S.E. (1990). "A Possible Role for Polypeptide Growth and Differentiation Factors in Periodontal Regeneration," Executive Committee on Chemotherpeutics; Amer. Acad Peridontal—Position Paper pp. 1-5.

Lynch, S.E. (1991). "Platelet-Derived Growth Factor and Insulin-Like Growth Factor. I: Mediators of Healing Soft Tissue and Bone Wounds," Periodontol Case Reports NE Soc. Periodontists Bull. 13(2):13-20.

Lynch, S.E. (1993). "Comparison of Results in the Canine and Primate Models Using a Single Regenerative Therapy," Abstract No. 37, J. Dental Res. 72:108.

Lynch, S.E. (1994). "The Role of Growth Factors in Periodontal Repair and Regeneration," Chapter 11 in Periodontal Regeneration: Current Status and Directions, Polson, A. ed., Quintessence Publishing Co, Inc: Chicago, IL, 11:179-197. cited byapplicant.

Lynch, S.E. (1995). "Introduction," in Tissue Engineering: Applications in Maxillofacial Surgery and Preiodontics, Lynch, S.E. et al. eds., Quintessence Publishing, pp. xi-xvi.

Lynch, S.E. (2005). "Bone Regeneration Techniques in the Orofacial Region," Chapter 18 in Bone Regeneration and Repair: Biology and Clinical Applications, Lieberman, J.R. et al. eds., Humana Press Inc.: Totowa, NJ, pp. 359-390.

Lynch, S.E et al. (1988). "Potential Role of Platelet-Derived and Insulin-Like Growth Factors in Periodontal Regeneration," Abstract No. 586, J. Dental Res. 67:186.

Lynch, S.E. et al. (1988). "Synergistic Effects of Recombinant Platelet-Derived Growth Factor Two and Insulin-Like Growth Factor-I in Wound Healing," Abstract No. 585, J. Dental Res. 67:186.

Lynch, S.E. et al. (1989). "A Combination of Platelet-Derived and Insulin-Like Growth Factors Enhances Periodontal Regeneration," J. Clin. Periodontol. 16:545-548.

Lynch, S.E. et al. (1989). "Comparative Effects of Growth Factors on Soft Tissue Repair," Abstract No. 1153, J. Dental Res. 68:326.

Lynch, S.E. et al. (1992). "Effect of PDGF-B and IGF-I on Bone Regeneration," Abstract No. 82, J. Dental Res. 71:116.

Lynch, S.E. et al. (1994). "Polypeptide Growth Factors: Molecular Mediators of Tissue Repair," Chapter 33 in Molecular Pathogenesis of Periodontal Disease, Genco, R. et al. eds., A.S.M. Press: Washington DC, pp. 415-425.

Lynch, S.E. et al. (2008). "Use of rhPDGF to Improve Bone and Periodontal Regeneration," Chapter 6 in Tissue Engineering: Applications in Maxillofacial Surgery and Periodontics, Second Edition, Lynch, S.E. et al. eds., Quintessence Publishing Co.:Hanover Park, IL, pp. 87-102.

Lynch, S.E. et al. (Dec. 1988). "Growth Factors in Wound Healing: Single and Synergistic Effects," Abstract No. 238, J. Cell Biol. 107(6 Part 3):46a.

Lynch, S.E. et al. (Jan.-Mar. 1994). "Evidence for a Synergistic Interaction of Platelet-Derived Growth Factor-BB and Insulin-Like Growth Factor-I to Promote bone Repair in Adult Yucatan Micro Pigs," Wound Repair and Regeneration Abstract, 2(1):84.

Lynch, S.E. et al. (Jul. 1991). "The Effects of Short Term Application of a Combination of Platelet-Derived and Insulin-Like Growth Factors on Periodontal Wound Healing," J. Periodontol. 62(7):458-467.

Lynch, S.E. et al. (Jul.-Sep. 1994). "The Combination of Platelet-Derived Growth Factor-BB and Insulin-Like Growth Factor-I Stimulates Bone Repair in Adult Yucatan Miniature Pigs," Wound Rep. Reg. 2(3):182-190.

Lynch, S.E. et al. (Nov. 1987). "Role of Platelet-Derived Growth Factor in Wound Healing: Synergistic Effects with Other Growth Factors," Proc. Natl. Acad. Sci. USA 84:7696-7700.

Lynch, S.E. et al. (Nov. 1991). "Effects of Platelet-Derived Growth Factor/Insulin Like Growth-Factor-I Combination on Bone Regeneration Around Titanium Dental Implants. Results of a Pilot Study in Beagle Dogs," J. Periodontol. 62(11):710-717.

Maffulli, N. et al. (2002). "Tendon Healing: Can It Be Optimized?" British Journal of Sports Medicine 36:315-316.

Maffulli, N. et al. (2003). "Types and Epidemiology of Tendinopathy," Clinics in Sports Medicine 22:675-692.

Maiorana et al, "Maxillary Sinus Augmentation with A-rganic Bovine Bone (Bio-Oss) and Autologous Platelet-Rich Plasma: Preliminary Clinical and Histologic Evaluations," Int J Periodontics Restorative Den, 2003, 23: 227-235.

Manske et al. (Feb. 1985). "Flexor Tendon Healing," Symposium on Flexor Tendon Surgery, Hand Clinics 1 (1):25-34.

Marcopoulou, et al., "Proliferative effect of growth factors TGF-beta1, PDGF-BB and rhBMP-2 on human gingival fibroblasts and periodontal ligament cells", J. Int. Acad. Periodontol., 5(3):63-70, 2003.

Marx, R.E. (2008). "Application of Tissue Engineering Principles to Clinical Practice," Chapter 4 in Tissue Engineering: Applications in Maxillofacial Surgery and Periodontics, Second Edition, Lynch, S.E. et al. eds., Quintessence Publishing Co.:Hanover Park, IL, pp. 47-63.

Marx, R.E. (2008). "Use of PRP in Oral and Maxillofacial Surgery and Periodontology," Chapter 9 in Tissue Engineering: Applications in Maxillofacial Surgery and Periodontics, Second Edition, Lynch, S.E. et al. eds., Quintessence Publishing Co.:Hanover Park, IL, pp. 132-144.

(56) References Cited

OTHER PUBLICATIONS

Marx, R.E. et al. (2005). "Bisphosphonate-Induced Exposed Bone (Osteonecrosis/Osteoperosis) of the Jaws: Risk Factors, Recognition, Prevention, and Treatment," J. Oral Maxillofac. Surg. 63:1567-1575.
Mayfield, L. et al. (Oct. 1998). "Clinical and Radiographic Evaluation, Following Delivery of Fixed Reconstructions, at GBR Treated Titanium Fixtures," Clin. Oral Implants Res. 9:292-302.
McAllister et al., "Eighteen-month Radiographic and Histologic Evaluation of Sinus Grafting with A-rganic Bovine Bone in the Chimpanzee," The International Journal of Oral & Maxillofacial Implants, 1999, 14(3): 361-368.
McAllister, B. et al. (1998). "Long-term Evaluation of Sinus Grafting with Bio-Oss.RTM. in the Chimpanzee," Abstract No. 1097, J. Dental Res. 77:769.
McCarrel, T. et al. (Aug. 2009, e-pub. Jan. 23, 2009). "Temporal Growth Factor Release from Platelet-Rich Plasma, Trehalose Lyophilized Platelets, and Bone Marrow Aspirate and their Effect on Tendon and Ligament Gene Expression," J. Orthop. Res.27(8):1033-1042, Abstract Only.
McGuire, M.K. (2008). "Soft Tissue Engineering Applications in Dentistry," Chapter 7 in Tissue Engineering: Applications in Maxillofacial Surgery and Periodontics, Second Edition, Lynch, S.E. et al. eds., Quintessence Publishing Co.: Hanover Park,IL, pp. 103-118.
McGuire, M.K. et al. (2006). "rhPDGF-BB Promotes Healing of Periodontal Defects: 24-Month Clinical and Radiographic Observations," Int. J. Periodontics Restorative Dent. 26(3):223-231.
McMurty, R.Y. et al. (1992). "Fractures of the Distal Radius," Chapter 35 in Skeletal Trauma, Browner B.D. et al. eds., W.B. Saunders Company: Philadelphia, PA, 2:1063-1094.
Melo, M.D. et al. (Dec. 2005). "Osteonecrosis of the Jaws in Patients with a History of Receiving Bisphosphonate Therapy. Strategies for Prevention and Early Recognition," J. American Dental Association 136:16751681.
Mheta, V. et al. (Apr.-Jun. 2005). "The Use of Growth Factors on Tendon Injuries," Journal of Hand Therapy 18:87-92.
Migliorati, C.A. et al. (Jun. 2006). "Bisphosphate-Associated Osteonecrosis: A Long Term Complication of Bisphophonate Treatment," Lancet Oncol. 7:508-514.
Millette, E. et al. (2006). "Platelet Derived Growth Factor-BB Transactivates the Fibroblast Growth Factor Receptor to Induce Proliferation in Human Smooth Muscles Cells," Trends Cardiov. Med. 16(1):25-28.
Mitlak et al., "The Effect of Systemically Administered PDGF-BB on the Rodent Skeleton," Journal of Bone and Mineral Research, 1996, 11(2): 238-247.
Molloy, T. et al. (2003). "The Roles of Growth Factors in Tendon and Ligament Healing," Sports Med. 33(5):381-394.
Mont, M.A. et al. (Oct. 1998). "Osteonecrosis of the Femoral Head. Potential Treatment with Growth and Differentiation Factors," Clin. Orthop. Relat. Res. 355(Suppl.):S314-S335, Abstract Only, 2 pages.
Morris, G.J. et al. (Jan. 2007). "Bisphosphonate Therapy for Women with Breast Cancer and at High Risk for Osteoporosis," Journal of the National Medical Association 99(1):35-45.
Mott, D.A. et al. (2002). "Enhancement of Osteoblast Proliferation in vitro by Selective Enrichment of Demineralized Freeze-Dried Bone Allograft with Specific Growth Factors," J. Oral Implantol. 28(2):57-66.
Mumford, J.H., et al., "The effects of platelet-derived growth factor-BB on periodontal cells in an in vitro wound model", J. Periodontol., 72(3):331-40, 2001.
Nakamura, N. et al., Early Biological Effect of In Vivo Gene Transfer of Platelet-derived Grown Factor (PDGF)-B into Healing Patellar Ligament, Gene Therapy, 1998, 5:1165-1170.
Nancollas, G.H. et al. (2006, e-pub. Jul. 20, 2005). "Novel Insights into Actions of Bisphosphonates on Bone: Differences in Interactions with Hydrozyapatite," Bone 38:617-627.
Nase, J.B. et al. (Aug. 2006). "Osteonecrosis of the Jaw and Oral Bisphosphonate Treatment," J. American Dental Association 137:1115-1119.

Nash, T.J. et al. (Mar. 1994). "Effect of Platelet-Derived Growth Factor on Tibial Osteotomies in Rabbits," Bone 15(2):203-208.
Nevia et al., "The Effect of Platelet-Rich Plasma on the Coronally Advanced Flap Root Coverage Procedure: A Pilot Human Trial," J. Periodontal, 2005, 76(10): 1768-1777.
Nevins et al., "Periodontal Regeneration in Humans Using Recombinant Human Platelet-derived Growth Factor-BB (rhPDGF-BB) and Allogenic Bone," J. Periodontal, 2003, 74(9): 1282-1292.
Nevins et al., "Platelet-Derived Growth Factor Stimulates Bone Fill and Rate of Attachment Level Gain: Results of a Large Multicenter Randomized Controlled Trial," J. Periodontal, 2005, 76(12): 2205-2215.
Nevins, M. et al. (2007). "Clinical Results Using Recombinant Human Platelet-Derived Growth Factor and Mineralized Freeze-Dried Bone Allograft in Periodontal Defects," Int. J. Periodontics Restorative Dent. 27(5):421-427.
Nevins, M. et al. (2008). "Treatment of Advanced Periodontal Defects Using Bioactive Therapies," Chapter 5 in Tissue Engineering: Applications in Maxillofacial Surgery and Periodontics, Second Edition, Lynch, S.E. et al. eds., Quintessencepublishing Co.: Hanover Park, IL, pp. 67-86.
Nevins, M.L. et al. (2003). "Evaluation of Periodontal Regeneration Following Grafting Intrabony Defects with Bio-Oss.RTM. Collagen: A Human Histologic Report," Int. J. Periodont. Rest. Dent. 23(1):9-17.
Nevins, M.L. et al. (2005). "Three-Dimensional Micro-Computed Tomographic Evaluation of Periodontal Regeneration: A Human Report of Intrabony Defects Treated with Bio-Oss Collagen," Int. J. Periodontics Restorative Dent. 25(4):365-373. cited byapplicant.
Nevins, M.L. et al. (2008). "Site Development for Implant Placement: Regenerative and Esthetic Techniques in Oral Plastic Surgery," Chapter 8 in Tissue Engineering: Applications in Maxillofacial Surgery and Periodontics, Second Edition, Lynch, S.E. et al. eds., Quintessence Publishing Co.: Hanover Park, IL, pp. 119-131.
Nickols, J.C. et al. (2008). "The Role of Growth Factors in Tendon Healing," Chapter 20 in Tissue Engineering: Applications in Maxillofacial Surgery and Periodontics, Second Edition, Lynch, S.E. et al. eds., Quintessence Publishing Co.: HanoverPark, IL, pp. 276-289.
Nistor, L. (Mar. 1981). "Surgical and Nonsurgical Treatment of Achilles Tendon Rupture: A Prospective Randomized Trial," J. Bone Joint Surg Am. 63A(3):394-399.
Nociti, F.H. Jr. et al. (2000). "Histometric Evaluation of Bone Regeneration Around Immediate Implants Partially in Contact with Bone: A Pilot Study in Dogs," Implant Dentistry 9(4):321-328.
Non-Final Office Action dated Jul. 16, 2010, for U.S. Appl. No. 12/368,242, filed Feb. 9, 2009, 12 pages.
Non-Final Office Action dated Jul. 27, 2007, for U.S. Appl. No. 11/159,533, filed Jun. 23, 2005, 13 pages.
Non-Final Office Action dated Jul. 7, 2010, for U.S. Appl. No. 12/323,183, filed Nov. 25, 2008, 11 pages.
Non-Final Office Action dated Oct. 16, 2009, for U.S. Appl. No. 11/704,685, filed Feb. 9, 2007, 19 pages.
Non-Final Office Action dated Sep. 14, 2010, for U.S. Appl. No. 11/601,376, filed Nov. 17, 2006, 18 pages.
Non-Final Office Action dated Sep. 23, 2010, for U.S. Appl. No. 12/513,491, filed Nov. 5, 2007, 10 pages.
Notice of Allowance dated Mar. 4, 2011, for U.S. Appl. No. 12/368,242, filed Feb. 9, 2009, 5 pages.
Oberg, S. et al. (Apr. 1994). "Bone Healing After Implantation of Hydroxyapatite Granules and Bblocks (Interpore 200) Combined with Autolyzed Antigen-Extracted Allogeneic Bone and Fibrin Glue. Experimental Studies on Adult Rabbits," Internationaljournal of Oral and Maxillofacial Surgery 23(2):110-114, abstract only.
Orbay, J.L. et al. (Jan. 2004). "Volar Fixed-Angle Plate Fixation for Unstable Distal Radius Fractures in the Elderly Patient," J. Hand Surg. 29A(1):96-102.
Orthovita, Inc. (2009). "Architects of the New Biomaterials Age, 2008 Annual Report," located at <http://orthovita.com/investors/annual-reports/previousreports.aspx>-;, last visited on Jun. 17, 2010, 93 pages.

(56) References Cited

OTHER PUBLICATIONS

Orthovita, Inc. (Dec. 14, 2000). "510(k) Summary. Vitoss.TM. Scaffold Syntehtic Cancellous Bone Void Filler," located at <http://www.accessdata.fda.gov/cdrh_docs/pdf/k994337.pdf>, last visited on Mar. 30, 2010, 6 pages.
Orthovita, Inc. (Nov. 19, 2002). "Morningstar.RTM. Document Research.TM.. Form 10-Q, Quarterly Repot Which Provides a Continuing View of a Company's Financial Position," located at <http://orthovita.com/investors/secfilings.aspx>, last visitedon Jun. 17, 2010, 48 pages.
Owen et al. "Simian sarcoma virus-transformed cells secrete a mitogen identical to platelet-derived growth factor," Science, 1984, 25:54-56.
Palti, A. et al. (2002). "A Concept for the Treatment of Various Dental Bone Defects," Implant Dentistry 11 (1):73-78.
Papadopoulos, C., et al., "In Vitro Evaluation of the Mitogenic Effect of Platelet-Derived Growth Factor-BB on Human Periodontal Ligament Cells Cultured with Various Bone Allografts," J Periodontol 2003;74:451-457.
Parashis, A. et al. (Jul. 1998). "Comparison of 2 Regenerative Procedures-Guided Tissue Regeneration and Demineralized Freeze-Dried Bone Allograft-in the Treatment of Intrabony Defects: A Clinical and Radiographic Study," J. Periodontol.69(7):751-758.
Park et al. "Periodontal Regeneration in Class III Furcation Defects of Beagle Dogs Using Guided Tissue Regenerative Therapy with Platelet-Derived Growth Factor," J. Periodontol., 1995, 66:462-477.
Paul, W. et al. (1999). "Development of Porous Spherical Hydroxyapatite Granules: Application Towards Protein Delivery," J. Mater. Sci. Mater. Med. 10:383-388.
Persson, G.R. et al. (2000). "A Retrospective Radiographic Outcome Assessment Study of Intra-Bony Defects Treated by Osseous Surgery or by Bone Graft Procedures," J. Clin. Periodontol. 27:104-108.
Petersen, W. et al. (Nov. 2003, e-pub. Apr. 16, 2003). "Hypoxia and PDGF Have a Synergistic Effect that Increases the Expression of the Angiogenetic Peptide Vascular Endothelial Growth Factor in Achilles Tendon Fibroblasts," Arch. Orthop. TraumaSurg. 123(9):485-488.
Pfeilschifter et al. "Stimulation of Bone Matrix Apposition in Vitro by Local Growth Factors: A Comparison Between Insulin-Like Growth Factor I, Platelet Derived Growth Factor, and Transforming Growth Factor 13," Endocrinology, 1990, 127(1):69-75.
Philippart et al., "Human Recombinant Tissue Factor, Platelet-rich Plasma, and Tetracycline Induce a High-Quality Human Bone Graft: A 5-year Survey," The International Journal of Oral and Maxillofacial Implants, 2003, 118: 411-416. cited byapplicant.
Phillips, S. et al. (1988). "The Direct Medical Costs of Osteoporosis for American Woman Aged 45 and Older, 1986," Bone 9(4):271-279.
Pickett, F.A. (Jul. 2006). "Bisphosphonate-Associated Osteonecrosis of the Jaw: A Literature Review and Clinical Practice Guidelines," Journal of Dental Hygiene 80(3):1-12.
Pietrzak, W.S. et al. (Jul. 2000). "Calcium Sulfate Bone Void Filler: A Review and a Look Ahead," J. Craniofac. Surg. 11 (4):327-333; discussion p. 334.
Polverini, P.J. (Aug. 2002). "Angiogenesis in Health and Disease: Insights into Basic Mechanisms and Therapeutic Opportunities," Journal of Dental Education 66(8):962-975.
Premdas, J. et al. (2001). "The Presence of Smooth Muscle Action in Fibroblasts in the Torn Human Rotator Cuff," Journal of Orthopaedic Research 19:221-228.
Qiu, Y. et al. (2009). "Combination of PDGF-BB and bFGF Reduces Differentiation but Maintains Proliferation of Human Tenocytes in Low Bovine Serum Culture in vitro," European Cells and Materials 18(Suppl. 2):86.
Qu, Z. et al. (Nov. 1994). "Immunolocalization of Basic Fibroblast Growth Factor and Platelet-Derived Growth Factor-A During Adjuvant Arthritis in the Lewis Rat," Am. J. Pathol. 145(5):1127-1139.
R&D Systems, Inc. (Date Unknown). "Quantikine.RTM. Human PDGF-BB Immunoassay," Package Insert, Catalog No. DBB00, SBB, and PDB00, located at <http://www.rndsystems.com/pdf/dbb00.pdf>, last visited on Mar. 30, 2010, 16 pages.
Rao et al. "Structure and Sequence of the Human C-SisIPlatelet-Derived Growth Factor 2," Proc. Natl. Acad. Sci. USA, 1986, 83:2392-2396.
Rao, M.V. et al. (Mar. 2009). "Effects of Platelet-Derived Growth Factor, Vitamin D and Parathroid Hormone on Osteoblasts Derived from Cancer Patients on Chronic Bisphosphonate Therapy," Int. J. Mol. Med. 23(3):407-413, Abstract Only, 2 pages.
Rasubala et al., "Platelet-derived Growth Factor and Bone Morphogenetic Protein in the Healing of Mandibular Fractures in Rats," British Journal of Oral and Maxillofacial Surgery, 2003, 41: 173-178.
Response to Advisory Action dated Apr. 28, 2008, for U.S. Appl. No. 11/159,533, filed Jun. 23, 2005, 15 pages.
Response to Notice of Non-Compliant Amendment dated Nov. 2, 2007, for U.S. Appl. No. 11/159,533, filed Jun. 23, 2005, 7 pages.
Rettig, A.C. et al. (2005). "Potential Risk of Rerupture in Primary Achilles Tendon Repair in Athletes Younger Than 30 Years of Age," Am. J. Sports Med. 33(1):119-123.
Rickert, M. et al. (2001). "A Growth and Differentiation Factor-5 (GDF-5)-Coated Suture Stimulates Tendon Healing in an Achilles Tendon Model in Rats," Growth Factors 19:115-126.
Riley, G. (2004, e-pub. Jul. 16, 2003). "The Pathogenesis of Tendinopathy. A Molecular Perspective," Rheumatology 43(2):131-142.
Robbins et al. "Structural and immunological similarities between simian sarcoma virus gene product(s) and human platelet-derived growth factor," Nature, 1983, 305:605-608.
Rodeo, S.A. et al. (1999). "Use of Recombinant Human Bone Morphogenic Protein-2 to Enhance Tendon Healing in a Bone Tunnel," Am. J. Sports Med. 27(4):476-488.
Rodeo, S.A. et al. (Dec. 1993). "Tendon Healing in a Bone Tunnel," J. Bone Joint Surg. Am. 75-A(12):1795-1803.
Rodriguez et al., "Maxillary Sinus Augmentation with Deproteinated Bovine Bone and Platelet Rich Plasma with Simultaneous Insertion of Endosseous Implants," J. Oral Maxillofac. Surg., 2003, 61:157-163.
Rohrich et al. (Nov. 1999). "Mersilene Suture as a Vehicle for Delivery of Growth Factors in Tendon Repair," Journal of the American Society of Plastic Surgeons 104(6):1713-1717.
Rolf, C.G. et al. (2001). "Increased Cell Proliferation and Associated Expression of PDGFR.beta. Causing Hypercellularity in Patellar Tendinosis," Rheumatology 40:256-261.
Ruggiero, S.L. et al. (2006, e-pub. Jul. 31, 2006). "Bisphosphonate-Related Osteoncerosis of the Jaw: Background and Guidelines for Diagnosis, Staging and Management," Oral Surgery, Oral Medicine, Oral Pathology, Oral Radiology, and Endodontology<http://www.sciencedirect.com/science/journal/10792104> 8 pages.
Ruiz, G. et al. (1991). "Short Term Administration of Growth Factors Enhances Periodontal Regeneration," Abstract No. 1615, J. Dental Res. 70:468.
Russell, T.A. et al. (Date Unknown). "Trigen.RTM. IM Nail System Surgical Technique. Trochanteric Antegrade Nail (TAN.TM.)," 24 pages.
Rutherford et al.; "Platelet-derived and insulin-like growth factors stimulate regeneration of periodontal attachment in monkeys"; Journal of Periodontal Research; 1992, vol. 27, Issue 4, Part 1, pp. 285-290.
Sakiyama-Elbert, S.E. et al. (Nov. 2008). "Controlled-Release Kinetics and Biologic Activity of Platelet-Derived Growth Factor-BB for Use in Flexor Tendon Repair," J. Hand Surg. Am. 33(9):1548-1557, Abstract Only.
Sandberg, "Matrix in Cartilage and Bone Development Current Views on the Function and Regulation of Major Organic Components," Annals of Medicine, 1991, 23: 207-217.
Sarment et al., "Effect of rhPDGF-BB on Bone Turnover During Periodontal Repair," J. Clin Periodontol, 2006, 33: 135-140.
Sartori, S. et al. (2003, e-pub. May 20, 2003). "Ten-year Follow-up in a Maxillary Sinus Augmentation Using Anorganic Bovine Bone (Bio-Oss): A Case Report with Histomorphometric Evaluation," Clin. Oral Implants Res. 14(3):369-372.

(56) References Cited

OTHER PUBLICATIONS

Sasai et al. "Xenopus chordin: a novel dorsalizing factor activated by organizer-specific homeobox genes," Cell, 1994, 79:779-790.
Saygin et al., "Molecular and Cell Biology of Cementum," Periodontology, 2000, 24: 73-98.
Schenk, R.K. et al. (Jan./Feb. 1994). "Healing Pattern of Bone Regeneration in Membrane-Protected Defects: A Histologic Study in the Canine Mandible," Int. J. Oral Maxillofac. Implants 9(1):13-29.
Schmidt, C.C. et al. (Mar. 1995). "Effect of Growth Factors on the Proliferation of Fibroblasts from the Medial Collateral and Anterior Cruciate Ligaments," J. Orthop. Res. 13(2):184-190, Abstract Only.
Schmidt, M.B. et al. (2008). "Tissue Engineering Strategies in the Treatment of TMDs," Chapter 18 in Tissue Engineering: Applications in Maxillofacial Surgery and Periodontics, Second Edition, Lynch, S.E. et al. eds., Quintessence Publishing Co.:Hanover Park, IL, pp. 252-264.
Schmitt et al., "A review of the effects of insulin-like growth factor and platelet derived growth factor on in vivo cartilage healing and repair," Osteoarthritis and Cartilage, 2006, 14(5): 403-412.
Schmitt, J.M. et al. (Nov. 1997). "Comparison of Porous Bone Mineral and Biologically Active Glass in Critical-Sized Defects," J. Periodontol. 68(11):1043-1053.
Schnabel, L.V. et al. (Feb. 2007). "Platelet Rich Plasma (PRP) Enhances Anabolic Gene Expression Patterns in Flexor Digitorum Superficialis Tendons," J. Orthop. Res. 25(2):230-240, Abstract Only.
Secinfo.com (Mar. 31, 2003). "Interpore International Inc/DE 10-K for Dec. 31, 2002," located at <http://www.secinfo.com/dV179.2kp.htm, last visited on May 20, 2010, 57 pages.
Seeherman, H.J. et al. (Oct. 2008). "rhBMP-12 Accelerates Healing of Rotator Cuff Repairs in Sheep Model," J. Bone Joint Surg. Am. 90A(10):2206-2219.
Shahgaldi, B.F. et al. (Jan. 1991). "Repair of Cartilage Lesions Using Biological Implants. A Comparative Histological and Biomechanical Study in Goats," J. Bone Joint Surg. Br. 73-B(1):57-64.
Sharma, P. et al. (2008). "Tendinopathy and Tendon Injury: The Future," Disability and Rehabilitation 30(20-22):1733-1745.
Sigma (Date Unknown). "Platelet Derived Growth Factor-BB," Product Information Sheet, 2 pages.
Simion, M. et al. (1994). "Vertical Ridge Augmentation Using a Membrane Technique Associated with Osseointegrated Implants," Int. J. Periodontics Restorative Dent. 14(6):497-511.
Simion, M. et al. (1995). "Bacterial Penetration in vitro Through GTAM Membrane With and Without Topical Chlorhexidine Application: A Light and Scanning Electron Microscopic Study," J. Clin. Periodontol. 22:321-331.
Simion, M. et al. (1999). "Effect of Different Microstructures of e-PTFE Membranes on Bone Regeneration and Soft Tissue Response: A Histologic Study in Canine Mandible," Clin. Oral Implants Res. 10:73-84.
Simion, M. et al. (2008). "Minimally Invasive Strategies for Vertical Ridge Augmentation," Chapter 10 in Tissue Engineering: Applications in Maxillofacial Surgery and Periodontics, Second Edition, Lynch, S.E. et al. eds., Quintessence PublishingCo.: Hanover Park, IL, pp. 145-158.
Simion, M. et al. (Apr. 1994). "A Comparative Study of the Effectiveness of e-PTFE Membranes With and Without Early Exposure During the Healing Period," Int. J. Periodontics Restorative Dent. 14(2):166-180.
Simion, M. et al. (Feb. 1998). "Vertical Ridge Augmentation Around Dental Implants Using a Membrane Technique and Autogenous Bone or Allografts in Humans," Int. J. Periodontics Restorative Dent. 18(1):9-23.
Simion, M. et al. (Oct. 2006). "Vertical Ridge Augmentation by Means of Deproteinized Bovine Bone Block and Recombination Human Platelet-Derived Growth Factor-BB: A Histologic Study in a Dog Model," The International Journal of Periodontics &Restorative Dentistry 26(5):415-423.
Siris, E.S. et al. (Aug. 2006). "Adherence to Bisphosphonate Therapy and Fracture Rates in Osteoporotic Women: Relationship to Vertebral and Nonvertebral Fractures From 2 US Claims Databases," Mayo Clin. Proc. 81(8):1013-1022.
Smith & Nephew (Date Unknown). "Trigen. Humeral Nail," Surgical Technique Pamphlet, 27 pages.
Sode, J. et al. (May 2007, e-pub. Mar. 3, 2007). "Use of Fluroquinolone and Risk of Achilles Tendon Rupture: A Population-based Cohort Study," Eur. J. Clin. Pharmacol. 63(5):499-503.
Solheim, "Growth Factors in Bone," International Orthopaedics (SICOT), 1998, 22: 410-416.
Spector, M. (2008). "Basic Principles of Scaffolds in Tissue Engineering," Chapter 2 in Tissue Engineering: Applications in Maxillofacial Surgery and Periodontics, Second Edition, Lynch, S.E. et al. eds., Quintessence Publishing Co.: Hanover Park, IL, pp. 26-36.
Spindler, K.P. et al. (1995). "Proliferative Response to Platelet-Derived Growth Factor in Young and Old Rat Patellar Tendon," Connective Tissue Research 31(2):171-177.
Spindler, K.P. et al., "Patellar Tendon and Anterior Curciate Ligament Have Different Mitogenic Responses to Platelet-derived Growth Factor and Transforming Growth Factor B," Journal of Orthopedic Research, 14:542-546.
Stephan et al., "Platelet-Derived Growth Factor Enhancement of a Mineral-Collagen Bone Substitute," J. Periodontol, 2000, 71: 1887-1892.
Stephan, E.B. et al. (Apr. 1999). "Anogranic Bovine Bone Supports Osteoblastic Cell Attachment and Proliferation," J. Periodontol. 70(4):364-369.
Strom, T.B. (Sep. 6, 2005). "Saving Islets from Allograft Rejection," PNAS USA 102(36):12651-12652.
Suba et al., "Facilitation of b-Tricalcium Phosphate-Induced Alveolar Bone Regeneration by Platelet-Rich Plasma in Beage Dogs: A Histologic and Histomorphometric Study," The International J. of Oral and Maxillofacial Implants, 2004, 19(6):832-838.
Supplemental Response to Advisory Action of Jun. 4, 2008, dated Jun. 9, 2008, for U.S. Appl. No. 11/159,533, filed Jun. 23, 2005, 15 pages.
Supplementary European Search Report dated Aug. 29, 2008, for EP Application No. 05803356.4, filed on Oct. 12, 2005, 7 pages.
Tadic, D. et al. (2004). "A Novel Method to Produce Hydroxyapatite Objects with Interconnecting Porosity that Avoids Sintering," Biomaterials 25(16):3335-3340.
Tamai, N. et al. (2002). "Novel Hydroxyapatite Ceramics with an Interconnective Porous Structure Exhibit Superior Osteoconduction in vivo," J. Biomed. Mater. Res. 59:110-117.
Teraoka, K. et al. (2004). "Construction of an Interconnected Pore Network Using Hydroxyapatite Beads," Key. Eng. Mater. 254-256:257-259.
Teraoka, K. et al. (Sep. 2004). "Construction of Interconnected Pore Network Using Hydroxyapatite Small Components," Trans. Mater. Res. Soc. Jpn. 29(6):2919-2921.
Thomopoulos, S. et al. (Feb. 2010, e-pub. Nov. 24, 2009). "bFGF and PDGF-BB for Tendon Repair: Controlled Release and Biologic Activity by Tendon Fibroblasts In Vitro," Ann. Biomed. Eng. 38(2):225-234.
Thomopoulos, S. et al. (Oct. 2007, e-pub. Jun. 5, 2007). "PDGF-BB Released in Tendon Repair Using a Novel Delivery System Promotes Cell Proliferation and Collagen Remodeling," J. Orthop. Res. 25(17):1358-1368.
Thomopoulos, S. et al. (Sep. 2009, e-pub. Mar. 25, 2009). "Enhanced Flexor Tendon Healing through Controlled Delivery of PDGF-BB," J. Orthop. Res. 27(9):1209-1215.
Thompoulos, S. et al. (May 2005). "Effect of Several Growth Factors on Canine Flexor Tendon Fibroblast Proliferation and Collagen Synthesis in vitro," J. Hand Surg. Am. 30(3):441-447, Abstract Only.
Tinti, C. et al. (1996). "Vertical Ridge Augmentation: What is the Limit?" Int. J. Periodontics Restorative Dent. 16(3):221-229.
Trending123.com (Date Unknown). "Stock Sectors. Medical Instruments Supls," located at <http://www.trending123.com/stock-sectors/Medical.sub.—Instruments.su- b.—Supls.html>, last visited on May 3, 2010, 11 pages.
U.S. Appl. No. 10/965,319, filed Oct. 14, 2004, by Lynch.

(56) References Cited

OTHER PUBLICATIONS

U.S. Appl. No. 12/556,555, filed Sep. 9, 2009, by Lynch et al.
Uggen, C. et al. (2010). "The Effect of Recombinant Human Platelet Derived Growth Factor BB-Coated Sutures on Rotator Cuff Healing in a Sheep Model," Arthroscopy 26(11):1456-1462.
Uggen, J.C. et al. (Jan. 2005). "Tendon Gene Therapy Modulates the Local Repair Enviornment in the Shoulder," J. Am. Osteopath. Assoc. 105(1):20-21.
Van Den Wyngaert, T. et al. (Aug. 2006). "Bisphosphonates and Osteonecrosis of the Jaw: Cause and Effect or a post hoc Fallacy?" Annals of Oncology 17(8):1197-1204.
Venkatasatya, M. et al. (2008). The Effect of PDGF, Vitamin D and PTH on Osteoblasts Derived From Patients on Chronic Bisphosphonate Therapy, Dissertation for The State University of New York at Buffalo, located at<http://gradworks.umi.com/14/531/1453440.html>, last visited on Mar. 31, 2010, 2 pages, Abstract Only.
Virchenko, O. et al. (2008, e-pub. Jul. 4, 2008). "Early Achilles Tendon Healing in Sheep," Arch. Orthop. Trauma Surg. 128:1001-1006.
Visnapuu et al., "Distribution of fibroblast growth factors (FGFR-1 and -3) and platelet-derived growth factor receptors (PDGFR) in the rat mandibular condyle during growth," Orthod. Craniofacial, 2002, 5: 147-153.
Walter, C. et al. (2006, e-pub. Aug. 29, 2006). "Prevalence of Bisphophonate Associated Osteonecrosis of the Jaw within the Filed of Osteonecrosis," Support Care Center 6 pages.
Wang et al. "A Large Family of Putative Transmembrane Receptors Homologous to the Product of the Drosophila Tissue Polarity Gene frizzled," J. Biol. Chem., 1998, 271:4468-4476.
Wang, L. et al. (2004). "Three-Dimensional Porous Network Structure Developed in Hydroxyapatite-Based Nanocomposites Containing Enzyme Pretreated Silk Fibronin," J. Nanopart. 6(1):91-98.
Wang, X.T. et al. (Sep. 2004). "Tendon Healing In Vitro: Genetic Modification of Tenocytes With Exogenous PDGF Gene and Promotion of Collagen Gene Expression," The Journal of Hand Surgery 29A(5):884-890.
Warner, J.J.P. et al. (Jan. 1992). "Anatomy and Relationships of the Suprascapular Nerve: Anatomical Constraints to Mobalization of the Supraspinauts and Infraspinatus Muscles in the Management of Massive Rotator-Cuff Tears," J. Bone Joint Surg. Am.74-A(1):36-45.
Wei et al., "Na—Fibrous Scaffold for Controlled Delivery of Recombinant Human PDGF-BB," Journal of Controlled Release, 2006, 112:103-110.
Weiler, A. et al. (2004). "The Influence of Locally Applied Platelet-Derived Growth Factor-BB on Free Tendon Graft Remodeling After Anterior Cruciate Ligament Reconstruction," Am. J. Sports Med. 32(4):881-891.
White, E. et al. (1986). "Biomaterial Aspects of Interpore-200 Porous Hydroxyapatite," Dent. Clin. North Am. 30(1):49-67, abstract only.
Wiesen, R.J. et al. (1998). "Efficacy of Bovine Bone Mineral in Vertical Osseous Defects," Abstract No. 1165, J. Dental Res. 77:777.
Wikesjo et al. "Effects of subgingival irrigation on A. actinomycetemcomitans," J. Clin. Perrodonto., 1989, 16:116-119.
Wikesjo et al. "Repair of periodontal furcation defects in beagle dogs following reconstructive surgery including root surface demineralization with tetracycline hydrochloride and topical fibronectin application," J. Clin. Periodontol., 1988,fl:73-80.
Williams et al., "Tissue Engineering: What Does It Mean? Why Is It Important?" Compendium, 2005, 26(1): 54-60.
Wisner-Lynch, L.A. (Oct. 2006). "From Passive to Active: Will Recombinant Growth Factor Therapeutics Revolutionize Regeneration?" Int. J. Periodont. and Rest. Dent. 26(5):409-411.
Wong, M.W. et al. (Oct. 2003). "Effect of Dexamethasone on Cultured Human Tenocytes and its Reversibility by Platelet-Derived Growth Factor," Journal of Bone and Joint Surgery American 85-A(10)1914-1920, Abstract Only.
Woo, S-B. et al. (May 16, 2006). "Systematic Review: Bisphosphonates and Osteonecrosis of the Jaws," Annals of Internal Medicine 144(10):753-761.
Woo, S.L-Y. et al. (1998). "Engineering the Healing of the Rabbit Medical Collateral Ligament," Medical and Biological Engineering and Computing 36:359-364.
Written Opinion of the International Searching Authority dated Apr. 27, 2010, for PCT Patent Application No. PCT/US2010/026450, filed on Mar. 5, 2010, 6 pages.
Written Opinion of the International Searching Authority dated Aug. 3, 2007, for PCT Application No. PCT/US07/003582, filed on Feb. 8, 2007, 7 pages.
Written Opinion of the International Searching Authority dated Aug. 4, 2008, for PCT Patent Application No. PCT/US2008/065666, filed on Jun. 3, 2008, 7 pages.
Written Opinion of the International Searching Authority dated Dec. 7, 2007, for PCT Application No. PCT/US2006/044766 filed on Nov. 17, 2006, 6 pages.
Written Opinion of the International Searching Authority dated Jul. 8, 2009, for PCT Patent Application No. PCT/US2008/054354, filed on Feb. 20, 2008, 10 pages.
Written Opinion of the International Searching Authority dated Jun. 26, 2009, for PCT Patent Application No. PCT/US2009/033596, filed on Feb. 9, 2009, 6 pages.
Written Opinion of the International Searching Authority dated May 20, 2009, for PCT Patent Application No. PCT/US2007/083638, filed on Nov. 5, 2007, 6 pages.
Written Opinion of the International Searching Authority dated Oct. 2, 2007, for PCT Application No. PCT/US05/36447, filed on Oct. 12, 2005, 4 pages.
Yang, C. et al. (2003). "Vascular Endothelial Growth Factor Gene Transfection to Enhance the Repair of Avascular Necrosis of the Femoral Head of Rabbit," Chinese Medical Journal 116(10):1544-1548.
Yazawa et al, "Basic Studies on the Clinical Applications of Platelet-Rich Plasma," Cell Transplantation, 2003, 12: 509-518.
Yazawa, M. et al. (May 2004). "Basic Studies on the Bone Formation Ability by Platelet Rich Plasma in Rabbits," Journal of Craniofacial Surgery 15(3):439-446.
Yokota, K. et al. (2008, e-pub. Feb. 1, 2008). "Platelet-Rich Plasma Accelerated Surgical Angio-Genesis in Vascular Necrotic Bone. An Experimental Study in Rabbits," Acta Orhopaedica 79(1):106-110.
Younger, E.M. et al. (1989). "Morbidity at Bone Graft Donor Sites," J. Orthop. Trauma 3(3):192-195.
Zavras, A.I. et al. (2006). "Bisphosphonates Are Associated With Increased Risk for Jaw Surgery in Medical Claims Data: Is it Osteonecrosis?" J. Oral Maxillofac. Surg. 64:917-923.
Zhu et al., "Gene Transfer and Expression of Platelet-Derived Growth Factors Modulate Periodontal Cellular Activity," J. Dent Res, 2001, 80(3):892-897.
Zimmer, Inc. (2005). "Zimmer.RTM. Collagen Repair Patch," Product No. 04-4100-001-00, 6 pages.

\* cited by examiner

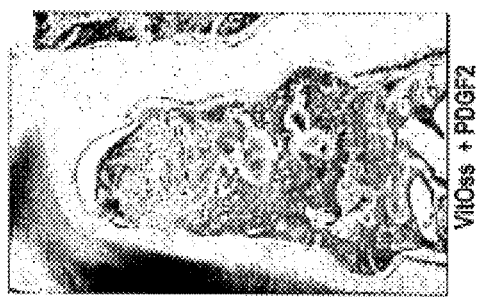
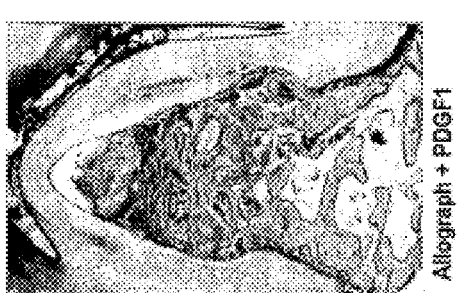
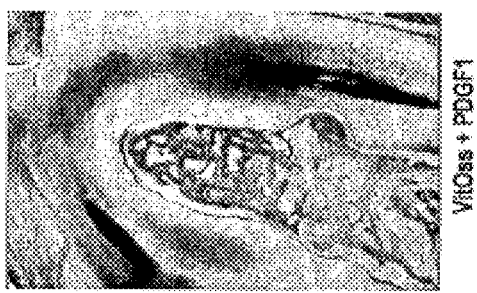
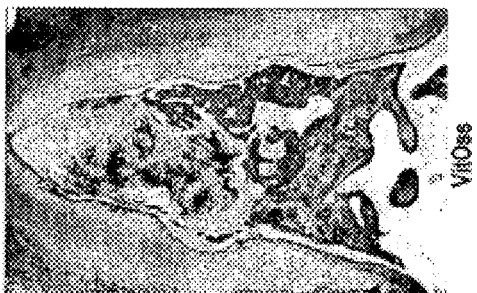
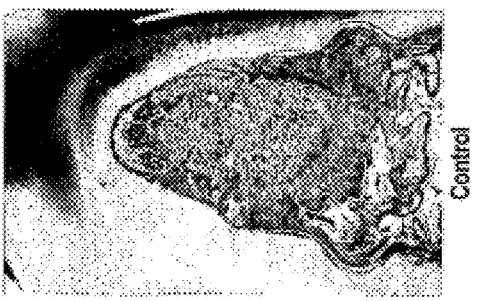

PLATELET-DERIVED GROWTH FACTOR COMPOSITIONS AND METHODS OF USE THEREOF

CROSS REFERENCE TO RELATED APPLICATIONS

This application is a continuation of U.S. application Ser. No. 11/778,498, filed on Jul. 16, 2007, now U.S. Pat. No. 9,545,377, which is a division of U.S. application Ser. No. 11/159,533, filed on Jun. 23, 2005, now U.S. Pat. No. 7,473,678, which is a continuation in part of, and claims priority from, U.S. patent application Ser. No. 10/965,319, filed Oct. 14, 2004, now abandoned each of which is incorporated by reference in its entirety.

FIELD OF THE INVENTION

This invention relates to the healing of bone and connective tissues.

BACKGROUND OF THE INVENTION

Growth factors are proteins that bind to receptors on a cell surface, with the primary result of activating cellular proliferation and/or differentiation. Many growth factors are quite versatile, stimulating cellular division in numerous different cell types; while others are specific to a particular cell-type. Examples of growth factors include platelet-derived growth factor (PDGF), insulin-like growth factors IGF-I and II), transforming growth factor beta (TGF-β), epidermal growth factor (EGF), and fibroblast growth factor (FGF). PDGF is a cationic, heat stable protein found in a variety of cell types, including the granules of circulating platelets, vascular smooth muscle cells, endothelial cells, macrophage, and keratinocytes, and is known to stimulate in vitro protein synthesis and collagen production by fibroblasts. It is also known to act as an in vitro mitogen and chemotactic agent for fibroblasts, smooth muscle cells, osteoblasts, and glial cells.

Recombinant human PDGF-BB (rhPDGF-BB) has been shown to stimulate wound healing and bone regeneration in both animals and humans. It is approved in both the United States and Europe for human use in topical applications to accelerate healing of chronic diabetic foot sores. Recombinant hPDGF-BB has also been shown to be effective either singly or in combination with other growth factors for improving periodontal regeneration, i.e., regrowth of bone, cementum, and ligament around teeth (see, e.g., U.S. Pat. No. 5,124,316, incorporated herein by reference).

SUMMARY OF THE INVENTION

We have now demonstrated that a low dose of rhPDGF (~0.1 to 1.0 mg/mL) promotes repair of bone, periodontium, ligament, and cartilage. A low amount of rhPDGF can be adsorbed to β-TCP, which can be implanted at the site of repair, such that the rhPDGF is released in vivo. Addition of rhPDGF to β-TCP has been shown to enhance osteoblast cell attachment and proliferation compared to untreated β-TCP.

In a first aspect, the invention features a method for promoting bone, periodontium, ligament, or cartilage growth in a mammal, e.g., a human, by administering an implant material containing platelet-derived growth factor (PDGF) at a concentration of less than about 1.0 mg/ml, such that the implant material promotes growth of the bone, periodontium, ligament, or cartilage. In an embodiment, the PDGF is administered in an amount of less than or equal to 0.3 mg/ml. In another embodiment, the PDGF is administered in an amount in the range of about 0.1 to about 1.0 mg/ml. In several embodiments, the PDGF is administered in an amount of between about 0.2 to about 0.75 mg/ml, about 0.25 to about 0.6 mg/ml, and about 0.25 to about 0.5 mg/ml. In an embodiment, the PDGF is administered in an amount of about 0.1 mg/ml, 0.3 mg/ml, or 1.0 mg/ml, preferably 0.3 mg/mL. In another embodiment, the PDGF is either partially or substantially purified. In yet a further embodiment, the PDGF is isolated or purified from other contaminants. In a further embodiment, the PDGF is released from the implant material upon administration at an average rate of 0.3 mg/day. In another embodiment, the PDGF is released from the implant material upon administration at an average rate of 300 µg/day. In still further embodiments, the PDGF is released from the implant material at an average rate of less than 100 µg/day, less than 50 µg/day, less than 10 µg/day, or less than 1 µg/day. Preferably, the PDGF is delivered over a few days, e.g., 1, 2, 5, 10, 15, 20, or 25 days, or up to 28 days or more.

A second aspect of the invention features a method for promoting bone, periodontium, ligament, or cartilage growth in a mammal, e.g., a human, by administering an implant material containing an amount of platelet-derived growth factor (PDGF) of less than about 1.0 mg/ml and a pharmaceutically acceptable carrier such that the implant material promotes the growth of the bone, periodontium, ligament, or cartilage, and allowing the bone, periodontium, ligament, or cartilage to grow. Preferably, the PDGF is equal to or less than about 0.3 mg/ml. In an embodiment, the PDGF is administered in a range of about 0.1 to 1.0 mg/ml. In other embodiments, the amount of PDGF is about 0.1 mg/ml, 0.3 mg/ml, or 1.0 mg/ml, preferably 0.3 mg/mL. In another embodiment, the PDGF is either partially or substantially purified. In yet a further embodiment, the PDGF is isolated or purified from other contaminants. Prior to administering the implant material to the mammal, the method can additionally include the step of producing a surgical flap of skin to expose the bone, periodontium, ligament, or cartilage, and following the administration step, replacing the flap. In yet another embodiment, after producing the surgical flap, but prior to administering the implant material to the bone, periodontium, ligament, or cartilage, the method can additionally include the step of planing the bone or periodontium to remove organic matter from the bone or periodontium. In yet another embodiment, the method promotes the growth of damaged or diseased bone, periodontium, ligament, or cartilage. In yet another embodiment, the method promotes the growth of bone in locations where new bone formation is required as a result of surgical interventions, such as, e.g., tooth extraction, ridge augmentation, esthetic grafting, and sinus lift.

A third aspect of the invention features an implant material for promoting the growth of bone, periodontium, ligament, or cartilage in a mammal, e.g., a human. The implant material includes a pharmaceutically acceptable carrier (e.g., a biocompatible binder, a bone substituting agent, a liquid, or a gel) and platelet-derived growth factor (PDGF), which is present at a concentration of less than about 1.0 mg/mL. Preferably, the PDGF is present in the implant material at a concentration equal to or less than about 0.3 mg/ml. In an embodiment, the PDGF is administered in a range of about 0.1 to 1.0 mg/ml. In other embodiments, the amount of PDGF is about 0.1 mg/ml, 0.3 mg/ml, or 1.0 mg/ml, preferably 0.3 mg/mL. In an embodiment, the pharmaceutically acceptable carrier of the implant material includes a scaffold or matrix consisting of a biocompatible binder (e.g., carboxymethylcellulose) or a bone substituting agent (β-TCP) that is capable of absorbing a solution that includes PDGF (e.g., a solution containing PDGF at a concentration in the range of about 0.1 mg/mL to about 1.0 mg/mL). In another embodiment, the pharmaceutically acceptable carrier is capable of absorbing an amount of the PDGF solution that is equal to at least about 25% of its own weight. In other embodiments, the pharmaceutically acceptable carrier is capable of absorbing an amount of the PDGF solution that is equal to at least about 50%, 75%, 100%, 200%, 250%, or 300% or its own weight. In an embodiment, the PDGF is absorbed by the pharmaceutically acceptable carrier of the implant material by soaking the pharmaceutically acceptable carrier in a solution containing PDGF. Preferably, the PDGF is present in the solution at a concentration of less than about 1.0 mg/mL. In another embodiment, the PDGF is present in the solution at a concentration equal to or less than about 0.3 mg/ml. In another embodiment, the PDGF is present in the solution at a concentration in the range of about 0.1 to 1.0 mg/ml. In yet other embodiments, the PDGF is present in the solution in an amount of about 0.1 mg/ml, 0.3 mg/m 1, or 1.0 mg/ml, preferably 0.3 mg/mL. In another embodiment, the PDGF is either partially or substantially purified. In yet a further embodiment, the PDGF is isolated or purified from other contaminants.

A fourth aspect of the invention features a method for preparing an implant material for promoting growth of bone, periodontium, ligament, or cartilage in a mammal, e.g., a human. The method includes the step of combining partially purified or purified platelet-derived growth factor (PDGF) in an amount of less than about 1.0 mg/mL with a pharmaceutically acceptable carrier substance. Preferably, the PDGF is combined with a pharmaceutically acceptable carrier substance at a concentration equal to or less than about 0.3 mg/ml. In an embodiment, the PDGF is combined with a pharmaceutically acceptable carrier substance in an amount in the range of about 0.1 to 1.0 mg/ml. In other embodiments, PDGF is mixed in the amount of 0.1 mg/ml, 0.3 mg/ml, or 1.0 mg/ml. In another embodiment, PDGF is mixed in the amount of 0.3 mg/ml. In yet another embodiment, the PDGF is absorbed by the pharmaceutically acceptable carrier to produce the implant material.

A fifth aspect of the invention features a vial having platelet-derived growth factor (PDGF) at a concentration in the range of about 0.1 mg/mL to about 1.0 mg/mL in a pharmaceutically acceptable liquid. In an embodiment of this aspect of the invention, the liquid is sterile sodium acetate buffer. In another embodiment, the vial contains PDGF at a concentration of about 0.3 mg/mL. In yet another preferred embodiment, the PDGF is PDGF-BB. In yet other embodiments, the PDGF is stable in the sodium acetate buffer for at least about 12 months, preferably at least about 18 months, more preferably at least about 24 months, and most preferably at least about 36 months when stored at a temperature in the range of about 2° C. to 80° C.

A sixth aspect of the invention features an implant material that includes a porous calcium phosphate having adsorbed therein a liquid containing platelet-derived growth factor (PDGF) at a concentration in the range of about 0.1 mg/mL to about 1.0 mg/mL. In several embodiments, the concentration of PDGF is about 0.3 mg/mL, the calcium phosphate is selected from tricalcium phosphate, hydroxyapatite, poorly crystalline hydroxyapatite, amorphous calcium phosphate, calcium metaphosphate, dicalcium phosphate dihydrate, heptacalcium phosphate, calcium pyrophosphate dihydrate, calcium pyrophosphate, and octa-calcium phosphate, and the PDGF is provided in a sterile liquid, for example, sodium acetate buffer.

A seventh aspect of the invention features a method of preparing an implant material by saturating a calcium phosphate material in a sterile liquid that includes platelet-derived growth factor (PDGF) at a concentration in the range of about 0.1 mg/mL to about 1.0 mg/mL. In several embodiments, the concentration of PDGF is about 0.3 mg/mL, and the calcium phosphate is selected from tricalcium phosphate, hydroxyapatite, poorly crystalline hydroxyapatite, amorphous calcium phosphate, calcium metaphosphate, dicalcium phosphate dihydrate, heptacalcium phosphate, calcium pyrophosphate dihydrate, calcium pyrophosphate, and octacalcium phosphate.

In an embodiment of all aspects of the invention, PDGF includes PDGF homo- and heterodimers, for example, PDGF-AA, PDGF-BB, PDGF-AB, PDGF-CC, and PDGF-DD, and combinations and derivatives thereof.

In an embodiment of all aspects of the invention, the pharmaceutically acceptable carrier substance of the implant material is or additionally includes one or more of the following: a biocompatible binder (e.g., a natural or synthetic polymer), a bone substituting agent, a liquid, and a gel. In another preferred embodiment, the implant material includes PDGF present in a pharmaceutically acceptable liquid carrier which is adsorbed by a pharmaceutically acceptable solid carrier.

In another embodiment of all aspects of the invention, the implant material is prepared by combining isolated, partially purified, substantially purified, or purified PDGF in an amount in the range of 0.1 to 1.0 mg/ml, more preferably 0.1 mg/ml, 0.3 mg/ml, or 1.0 mg/ml, most preferably 0.3 mg/ml, or even less than 0.1 mg/ml, with a pharmaceutically acceptable carrier substance, e.g., a biocompatible binder, such as a natural or synthetic polymer (e.g., collagen, polyglycolic acid, and polylactic acid), a bone substituting agent (e.g., a calcium phosphate (e.g., tricalcium phosphate or hydroxyapatite), calcium sulfate, or demineralized bone (e.g., demineralized freeze-dried cortical or cancellous bone), or a commercially available gel or liquid (i.e., a viscous or inert gel or liquid).

In several embodiments, the carrier substance of the implant material is, or additionally includes, one or more biocompatible binders. A biocompatible binder is an agent that produces or promotes cohesion between the combined substances. Non-limiting examples of suitable biocompatible binders include polymers selected from polysaccharides, nucleic acids, carbohydrates, proteins, polypeptides, poly(α-hydroxy acids), poly(lactones), poly(amino acids), poly(anhydrides), poly(orthoesters), poly(anhydride-co-imides), poly(orthocarbonates), poly(α-hydroxy alkanoates), poly(dioxanones), poly(phosphoesters), polylactic acid, poly(L-lactide) (PLLA), poly(D,L-lactide) (PDLLA), polyglycolide (PGA), poly(lactide-co-glycolide (PLGA), poly(L-lactide-co-D, L-lactide), poly(D,L-lactide-co-trimethylene carbonate), polyglycolic acid, polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly (vinyl alcohol), poly(vinylpyrrolidone), poly(ethyloxazoline), poly(ethylene oxide)-co-poly(propylene oxide) block copolymers, poly(ethylene terephthalate)polyamide, and copolymers and mixtures thereof. Additional binders include alginic acid, arabic gum, guar gum, xantham gum, gelatin, chitin, chitosan, chitosan acetate, chitosan lactate, chondroitin sulfate, N,O-carboxymethyl chitosan, a dextran (e.g., α-cyclodextrin, β-cyclodextrin, γ-cyclodextrin, or sodium dextran sulfate), fibrin glue, glycerol, hyaluronic acid, sodium hyaluronate, a cellulose (e.g., methylcellulose, carboxy methylcellulose, hydroxypropyl methylcellulose, or hydroxyethyl cellulose), a glucosamine, a proteoglycan, a starch (e.g., hydroxyethyl starch or starch soluble), lactic acid, a pluronic, sodium glycerophosphate, collagen, glycogen, a keratin, silk, and derivatives and mixtures thereof. In some embodiments, the biocompatible binder is water-soluble. A water-soluble binder dissolves from the implant material shortly after its implantation in vivo, thereby introducing macroporosity into the implant material. This macroporosity increases the osteoconductivity of the implant material by enhancing the access and, consequently, the remodeling activity of the osteoclasts and osteoblasts at the implant site.

The biocompatible binder may be added to the implant material in varying amounts and at a variety of stages during the preparation of the composition. Those of skill in the art will be able to determine the amount of binder and the method of inclusion required for a given application.

In an embodiment, the carrier substance is or includes a liquid selected from water, a buffer, and a cell culture medium. The liquid may be used in any pH range, but most often will be used in the range of pH 5.0 to pH 8.0. In an embodiment, the pH will be compatible with the prolonged stability and efficacy of the PDGF present in the implant material, or with the prolonged stability and efficacy of another desired biologically active agent. In most embodiments, the pH of the liquid will be in the range of pH 5.5 to pH 7.4. Suitable buffers include, but are not limited to, carbonates, phosphates (e.g., phosphate buffered saline), and organic buffers such as Tris, HEPES, and MOPS. Most often, the buffer will be selected for its biocompatibility with the host tissues and its compatibility with the biologically active agent. For most applications in which nucleic acids, peptides, or antibiotics are included in the implant material, a simple phosphate buffered saline will suffice.

In another embodiment of all aspects of the invention, the carrier substance of the implant material is, or additionally includes, one or more bone substituting agents. A bone substituting agent is one that can be used to permanently or temporarily replace bone. Following implantation, the bone substituting agent can be retained by the body or it can be resorbed by the body and replaced with bone. Exemplary bone substituting agent include, e.g., a calcium phosphate (e.g., tricalcium phosphate (e.g., β-TCP), hydroxyapatite, poorly crystalline hydroxyapatite, amorphous calcium phosphate, calcium metaphosphate, dicalcium phosphate dihydrate, heptacalcium phosphate, calcium pyrophosphate dihydrate, calcium pyrophosphate, and octacalcium phosphate), calcium sulfate, or demineralized bone (e.g., demineralized freeze-dried cortical or cancellous bone)). In an embodiment, the carrier substance is bioresorbable. In another embodiment, the bone substituting agent is provided as a matrix of micron- or submicron-sized particles, e.g., nano-sized particles. The particles can be in the range of about 100 μm to about 5000 μm in size, more preferably in the range of about 200 μm to about 3000 μm, and most preferably in the range of about 250 μm to about 2000 μm, or the particles can be in the range of about 1 nm to about 1000 nm, preferably less than about 500 nm, and more preferably less than about 250 nm. In another embodiment, the bone substituting agent has a porous composition. Porosity of the composition is a desirable characteristic as it facilitates cell migration and infiltration into the composition so that the cells can secrete extracellular bone matrix. It also provides access for vascularization. Porosity also provides a high surface area for enhanced resorption and release of active substances, as well as increased cell-matrix interaction. Preferably, the composition has a porosity of greater than 40%, more preferably greater than 65%, and most preferably greater than 90%. The composition can be provided in a shape suitable for implantation (e.g., a sphere, a cylinder, or a block) or it can be sized and shaped prior to use. In a preferred embodiment, the bone substituting agent is a calcium phosphate (e.g., β-TCP).

The bone substituting agent can also be provided as a flowable, moldable paste or putty. Preferably, the bone substituting agent is a calcium phosphate paste that self-hardens to form a hardened calcium phosphate prior to or after implantation in vivo. The calcium phosphate component of the invention may be any biocompatible calcium phosphate material known in the art. The calcium phosphate material may be produced by any one of a variety of methods and using any suitable starting components. For example, the calcium phosphate material may include amorphous, apatitic calcium phosphate. Calcium phosphate material may be produced by solid-state acid-base reaction of crystalline calcium phosphate reactants to form crystalline hydroxyapatite solids. Other methods of making calcium phosphate materials are known in the art, some of which are described below.

The calcium phosphate material can be poorly crystalline apatitic (PCA) calcium phosphate or hydroxyapatite (HA). PCA material is described in application U.S. Pat. Nos. 5,650,176; 5,783,217; 6,027,742; 6,214,368; 6,287,341; 6,331,312; and 6,541,037, all of which are incorporated herein by reference. HA is described, for example, in U.S. Pat. Nos. Re. 33,221 and Re. 33,161. These patents teach preparation of calcium phosphate remineralization compositions and of a finely crystalline, non-ceramic, gradually resorbable hydroxyapatite carrier material based on the same calcium phosphate composition. A similar calcium phosphate system, which consists of tetracalcium phosphate (TTCP) and monocalcium phosphate (MCP) or its monohydrate form (MCPM), is described in U.S. Pat. Nos. 5,053,212 and 5,129,905. This calcium phosphate material is produced by solid-state acid-base reaction of crystalline calcium phosphate reactants to form crystalline hydroxyapatite solids.

Crystalline HA materials (commonly referred to as dahllite) may be prepared such that they are flowable, moldable, and capable of hardening in situ (see U.S. Pat. No. 5,962,028). These HA materials (commonly referred to as carbonated hydroxyapatite) can be formed by combining the reactants with a non-aqueous liquid to provide a substantially uniform mixture, shaping the mixture as appropriate, and allowing the mixture to harden in the presence of water (e.g., before or after implantation). During hardening, the mixture crystallizes into a solid and essentially monolithic apatitic structure.

The reactants will generally consist of a phosphate source, e.g., phosphoric acid or phosphate salts, substantially free of water, an alkali earth metal, particularly calcium, source, optionally crystalline nuclei, particularly hydroxyapatite or calcium phosphate crystals, calcium carbonate, and a physiologically acceptable lubricant, such as any of the non-aqueous liquids described herein. The dry ingredients may be pre-prepared as a mixture and subsequently combined with the non-aqueous liquid ingredients under conditions where substantially uniform mixing occurs.

The calcium phosphate material is characterized by its biological resorbability, biocompatibility, and its minimal crystallinity. Its crystalline character is substantially the same as natural bone. Preferably, the calcium phosphate material hardens in less than five hours, and substantially hardens in about one to five hours, under physiological conditions. Preferably, the material is substantially hardened within about 10-30 minutes. The hardening rate under physiological conditions, may be varied according to the therapeutic need by modifying a few simple parameters as described in U.S. Pat. No. 6,027,742, which is incorporated herein by reference.

In an embodiment, the resulting bioresorbable calcium phosphate material will be "calcium deficient," with a calcium to phosphate molar ratio of less than about 1.6 as compared to the ideal stoichiometric value of approximately 1.67 for hydroxyapatite.

Desirable calcium phosphates are capable of hardening in a moist environment, at or around body temperature in less than 5 hours and preferably within 10-30 minutes. Desirable materials are those that, when implanted as a 1-5 g pellet, are at least 80% resorbed within one year. Preferably, the material can be fully resorbed.

In several embodiments of all aspects of the invention, the implant material additionally may include one or more biologically active agents. Biologically active agents that can be incorporated into the implant materials of the invention include, without limitation, organic molecules, inorganic materials, proteins, peptides, nucleic acids (e.g., genes, gene fragments, gene regulatory sequences, and antisense molecules), nucleoproteins, polysaccharides, glycoproteins, and lipoproteins. Classes of biologically active compounds that can be incorporated into the implant materials of the invention include, without limitation, anti-cancer agents, antibiotics, analgesics, anti-inflammatory agents, immunosuppressants, enzyme inhibitors, antihistamines, anti-convulsants, hormones, muscle relaxants, anti-spasmodics, ophthalmic agents, prostaglandins, anti-depressants, anti-psychotic substances, trophic factors, osteoinductive proteins, growth factors, and vaccines.

Anti-cancer agents include alkylating agents, platinum agents, antimetabolites, topoisomerase inhibitors, antitumor antibiotics, antimitotic agents, aromatase inhibitors, thymidylate synthase inhibitors, DNA antagonists, farnesyltransferase inhibitors, pump inhibitors, histone acetyltransferase inhibitors, metalloproteinase inhibitors, ribonucleoside reductase inhibitors, TNF alpha agonists/antagonists, endothelin A receptor antagonists, retinoic acid receptor agonists, immuno-modulators, hormonal and anti-hormonal agents, photodynamic agents, and tyrosine kinase inhibitors.

Any of the biologically active agents listed in Table 1 can be used.

TABLE 1

| | | |
|---|---|---|
| Alkylating agents | cyclophosphamide | lomustine |
| | busulfan | procarbazine |
| | ifosfamide | altretamine |
| | melphalan | estramustine phosphate |
| | hexamethylmelamine | mechlorethamine |
| | thiotepa | streptozocin |
| | chlorambucil | temozolomide |
| | dacarbazine | semustine |
| | carmustine | |
| Platinum agents | cisplatin | carboplatinum |
| | oxaliplatin | ZD-0473 (AnorMED) |
| | spiroplatinum, | lobaplatin (Aeterna) |
| | carboxyphthalatoplatinum, | satraplatin (Johnson Matthey) |
| | tetraplatin | BBR-3464 (Hoffmann-La Roche) |
| | ormiplatin | SM-11355 (Sumitomo) |
| | iproplatin | AP-5280 (Access) |
| Antimetabolites | azacytidine | tomudex |
| | gemcitabine | trimetrexate |
| | capecitabine | deoxycoformycin |
| | 5-fluorouracil | fludarabine |
| | floxuridine | pentostatin |
| | 2-chlorodeoxyadenosine | raltitrexed |
| | 6-mercaptopurine | hydroxyurea |
| | 6-thioguanine | decitabine (SuperGen) |
| | cytarabin | clofarabine (Bioenvision) |
| | 2-fluorodeoxy cytidine | irofulven (MGI Pharma) |
| | methotrexate | DMDC (Hoffmann-La Roche) |
| | idatrexate | ethynylcytidine (Taiho) |
| Topoisomerase inhibitors | amsacrine | rubitecan (SuperGen) |
| | epirubicin | exatecan mesylate (Daiichi) |
| | etoposide | quinamed (ChemGenex) |
| | teniposide or mitoxantrone | gimatecan (Sigma-Tau) |
| | irinotecan (CPT-11) | diflomotecan (Beaufour-Ipsen) |
| | 7-ethyl-10-hydroxy-camptothecin | TAS-103 (Taiho) |
| | topotecan | elsamitrucin (Spectrum) |
| | dexrazoxanet (TopoTarget) | J-107088 (Merck & Co) |
| | pixantrone (Novuspharma) | BNP-1350 (BioNumerik) |
| | rebeccamycin analogue (Exelixis) | CKD-602 (Chong Kun Dang) |
| | BBR-3576 (Novuspharma) | KW-2170 (Kyowa Hakko) |
| Antitumor antibiotics | dactinomycin (actinomycin D) | amonafide |
| | doxorubicin (adriamycin) | azonafide |
| | deoxyrubicin | anthrapyrazole |
| | valrubicin | oxantrazole |
| | daunorubicin (daunomycin) | losoxantrone |

TABLE 1-continued

| | | |
|---|---|---|
| | epirubicin | bleomycin sulfate (blenoxane) |
| | therarubicin | bleomycinic acid |
| | idarubicin | bleomycin A |
| | rubidazone | bleomycin B |
| | plicamycinp | mitomycin C |
| | porfiromycin | MEN-10755 (Menarini) |
| | cyanomorpholinodoxorubicin | GPX-100 (Gem Pharmaceuticals) |
| | mitoxantrone (novantrone) | |
| Antimitotic agents | paclitaxel | SB 408075 (GlaxoSmithKline) |
| | docetaxel | E7010 (Abbott) |
| | colchicine | PG-TXL (Cell Therapeutics) |
| | vinblastine | IDN 5109 (Bayer) |
| | vincristine | A 105972 (Abbott) |
| | vinorelbine | A 204197 (Abbott) |
| | vindesine | LU 223651 (BASF) |
| | dolastatin 10 (NCI) | D 24851 (ASTAMedica) |
| | rhizoxin (Fujisawa) | ER-86526 (Eisai) |
| | mivobulin (Warner-Lambert) | combretastatin A4 (BMS) |
| | cemadotin (BASF) | isohomohalichondrin-B (PharmaMar) |
| | RPR 109881A (Aventis) | ZD 6126 (AstraZeneca) |
| | TXD 258 (Aventis) | PEG-paclitaxel (Enzon) |
| | epothilone B (Novartis) | AZ10992 (Asahi) |
| | T 900607 (Tularik) | IDN-5109 (Indena) |
| | T 138067 (Tularik) | AVLB (Prescient NeuroPharma) |
| | cryptophycin 52 (Eli Lilly) | azaepothilone B (BMS) |
| | vinflunine (Fabre) | BNP-7787 (BioNumerik) |
| | auristatin PE (Teikoku Hormone) | CA-4 prodrug (OXiGENE) |
| | BMS 247550 (BMS) | dolastatin-10 (NIH) |
| | BMS 184476 (BMS) | CA-4 (OXiGENE) |
| | BMS 188797 (BMS) | |
| | taxoprexin (Protarga) | |
| Aromatase inhibitors | aminoglutethimide | exemestane |
| | letrozole | atamestane (BioMedicines) |
| | anastrazole | YM-511 (Yamanouchi) |
| | formestane | |
| Thymidylate synthase inhibitors | pemetrexed (Eli Lilly) | nolatrexed (Eximias) |
| | ZD-9331 (BTG) | CoFactor™ (BioKeys) |
| DNA antagonists | trabectedin (PharmaMar) | mafosfamide (Baxter International) |
| | glufosfamide (Baxter International) | apaziquone (Spectrum Pharmaceuticals) |
| | albumin + 32P (Isotope Solutions) | O6 benzyl guanine (Paligent) |
| | thymectacin (NewBiotics) | |
| | edotreotide (Novartis) | |
| Farnesyltransferase inhibitors | arglabin (NuOncology Labs) | tipifarnib (Johnson & Johnson) |
| | lonafarnib (Schering-Plough) | perillyl alcohol (DOR BioPharma) |
| | BAY-43-9006 (Bayer) | |
| Pump inhibitors | CBT-1 (CBA Pharma) | zosuquidar trihydrochloride (Eli Lilly) |
| | tariquidar (Xenova) | biricodar dicitrate (Vertex) |
| | MS-209 (Schering AG) | |
| Histone acetyltransferase inhibitors | tacedinaline (Pfizer) | pivaloyloxymethyl butyrate (Titan) |
| | SAHA (Aton Pharma) | depsipeptide (Fujisawa) |
| | MS-275 (Schering AG) | |
| Metalloproteinase inhibitors | Neovastat (Aeterna Laboratories) | CMT-3 (CollaGenex) |
| | marimastat (British Biotech) | BMS-275291 (Celltech) |
| Ribonucleoside reductase inhibitors | gallium maltolate (Titan) | tezacitabine (Aventis) |
| | triapine (Vion) | didox (Molecules for Health) |
| TNF alpha agonists/antagonists | virulizin (Lorus Therapeutics) | revimid (Celgene) |
| | CDC-394 (Celgene) | entanercept (Immunex Corp.) |
| | infliximab (Centocor, Inc.) | |
| | adalimumab (Abbott Laboratories) | |
| Endothelin A receptor antagonist | atrasentan (Abbott) | YM-598 (Yamanouchi) |
| | ZD-4054 (AstraZeneca) | |
| Retinoic acid receptor agonists | fenretinide (Johnson & Johnson) | alitretinoin (Ligand) |
| | LGD-1550 (Ligand) | |
| Immuno-modulators | interferon | dexosome therapy (Anosys) |
| | oncophage (Antigenics) | pentrix (Australian Cancer Technology) |
| | GMK (Progenics) | ISF-154 (Tragen) |
| | adenocarcinoma vaccine (Biomira) | cancer vaccine (Intercell) |
| | CTP-37 (AVI BioPharma) | norelin (Biostar) |
| | IRX-2 (Immuno-Rx) | BLP-25 (Biomira) |
| | PEP-005 (Peplin Biotech) | MGV (Progenics) |
| | synchrovax vaccines (CTL Immuno) | β-alethine (Dovetail) |
| | melanoma vaccine (CTL Immuno) | CLL therapy (Vasogen) |
| | p21 RAS vaccine (GemVax) | |
| Hormonal and antihormonal agents | estrogens | prednisone |
| | conjugated estrogens | methylprednisolone |
| | ethinyl estradiol | prednisolone |
| | chlortrianisen | aminoglutethimide |
| | idenestrol | leuprolide |
| | hydroxyprogesterone caproate | goserelin |
| | medroxyprogesterone | leuporelin |

TABLE 1-continued

|  | testosterone | bicalutamide |
|---|---|---|
|  | testosterone propionate; fluoxymesterone | flutamide |
|  | methyltestosterone | octreotide |
|  | diethylstilbestrol | nilutamide |
|  | megestrol | mitotane |
|  | tamoxifen | P-04 (Novogen) |
|  | toremofine | 2-methoxyestradiol (EntreMed) |
|  | dexamethasone | arzoxifene (Eli Lilly) |
| Photodynamic agents | talaporfin (Light Sciences) | Pd-bacteriopheophorbide (Yeda) |
|  | Theralux (Theratechnologies) | lutetium texaphyrin (Pharmacyclics) |
|  | motexafin gadolinium (Pharmacyclics) | hypericin |
| Tyrosine Kinase Inhibitors | imatinib (Novartis) | kahalide F (PharmaMar) |
|  | leflunomide (Sugen/Pharmacia) | CEP-701 (Cephalon) |
|  | ZD1839 (AstraZeneca) | CEP-751 (Cephalon) |
|  | erlotinib (Oncogene Science) | MLN518 (Millenium) |
|  | canertinib (Pfizer) | PKC412 (Novartis) |
|  | squalamine (Genaera) | phenoxodiol ( ) |
|  | SU5416 (Pharmacia) | trastuzumab (Genentech) |
|  | SU6668 (Pharmacia) | C225 (ImClone) |
|  | ZD4190 (AstraZeneca) | rhu-Mab (Genentech) |
|  | ZD6474 (AstraZeneca) | MDX-H210 (Medarex) |
|  | vatalanib (Novartis) | 2C4 (Genentech) |
|  | PKI166 (Novartis) | MDX-447 (Medarex) |
|  | GW2016 (GlaxoSmithKline) | ABX-EGF (Abgenix) |
|  | EKB-509 (Wyeth) | IMC-1C11 (ImClone) |
|  | EKB-569 (Wyeth) |  |

Antibiotics include aminoglycosides (e.g., gentamicin, tobramycin, netilmicin, streptomycin, amikacin, neomycin), bacitracin, corbapenems (e.g., imipenem/cislastatin), cephalosporins, colistin, methenamine, monobactams (e.g., aztreonam), penicillins (e.g., penicillin G, penicillin V, methicillin, natcillin, oxacillin, cloxacillin, dicloxacillin, ampicillin, amoxicillin, carbenicillin, ticarcillin, piperacillin, mezlocillin, azlocillin), polymyxin B, quinolones, and vancomycin; and bacteriostatic agents such as chloramphenicol, clindanyan, macrolides (e.g., erythromycin, azithromycin, clarithromycin), lincomyan, nitrofurantoin, sulfonamides, tetracyclines (e.g., tetracycline, doxycycline, minocycline, demeclocyline), and trimethoprim. Also included are metronidazole, fluoroquinolones, and ritampin.

Enzyme inhibitors are substances which inhibit an enzymatic reaction. Examples of enzyme inhibitors include edrophonium chloride, N-methylphysostigmine, neostigmine bromide, physostigmine sulfate, tacrine, tacrine, 1-hydroxy maleate, iodotubercidin, p-bromotetramisole, 10-(alpha-diethylaminopropionyl)-phenothiazine hydrochloride, calmidazolium chloride, hemicholinium-3,3,5-dinitrocatechol, diacylglycerol kinase inhibitor I, diacylglycerol kinase inhibitor II, 3-phenylpropargylamine, $N^6$-monomethyl-L-arginine acetate, carbidopa, 3-hydroxybenzylhydrazine, hydralazine, clorgyline, deprenyl, hydroxylamine, iproniazid phosphate, 6-MeO-tetrahydro-9H-pyrido-indole, nialamide, pargyline, quinacrine, semicarbazide, tranylcypromine, N,N-diethylaminoethyl-2,2-diphenylvalerate hydrochloride, 3-isobutyl-1-methylxanthne, papaverine, indomethacind, 2-cyclooctyl-2-hydroxyethylamine hydrochloride, 2,3-dichloro-a-methylbenzylamine (DCMB), 8,9-dichloro-2,3,4,5-tetrahydro-1H-2-benzazepine hydrochloride, p-aminoglutethimide, p-aminoglutethimide tartrate, 3-iodotyrosine, alpha-methyltyrosine, acetazolamide, dichlorphenamide, 6-hydroxy-2-benzothiazolesulfonamide, and allopurinol.

Antihistamines include pyrilamine, chlorpheniramine, and tetrahydrazoline, among others.

Anti-inflammatory agents include corticosteroids, non-steroidal anti-inflammatory drugs (e.g., aspirin, phenylbutazone, indomethacin, sulindac, tolmetin, ibuprofen, piroxicam, and fenamates), acetaminophen, phenacetin, gold salts, chloroquine, D-Penicillamine, methotrexate colchicine, allopurinol, probenecid, and sulfinpyrazone.

Muscle relaxants include mephenesin, methocarbomal, cyclobenzaprine hydrochloride, trihexylphenidyl hydrochloride, levodopa/carbidopa, and biperiden.

Anti-spasmodics include atropine, scopolamine, oxyphenonium, and papaverine.

Analgesics include aspirin, phenylbutazone, idomethacin, sulindac, tolmetic, ibuprofen, piroxicam, fenamates, acetaminophen, phenacetin, morphine sulfate, codeine sulfate, meperidine, nalorphine, opioids (e.g., codeine sulfate, fentanyl citrate, hydrocodone bitartrate, loperamide, morphine sulfate, noscapine, norcodeine, normorphine, thebaine, norbinaltorphimine, buprenorphine, chlornaltrexamine, funaltrexamione, nalbuphine, nalorphine, naloxone, naloxonazine, naltrexone, and naltrindole), procaine, lidocain, tetracaine and dibucaine.

Ophthalmic agents include sodium fluorescein, rose bengal, methacholine, adrenaline, cocaine, atropine, alpha-chymotrypsin, hyaluronidase, betaxalol, pilocarpine, timolol, timolol salts, and combinations thereof.

Prostaglandins are art recognized and are a class of naturally occurring chemically related, long-chain hydroxy fatty acids that have a variety of biological effects.

Anti-depressants are substances capable of preventing or relieving depression. Examples of anti-depressants include imipramine, amitriptyline, nortriptyline, protriptyline, desipramine, amoxapine, doxepin, maprotiline, tranylcypromine, phenelzine, and isocarboxazide.

Growth factors are factors whose continued presence improves the viability or longevity of a cell. Trophic factors include, without limitation, neutrophil-activating protein, monocyte chemoattractant protein, macrophage-inflammatory protein, platelet factor, platelet basic protein, and melanoma growth stimulating activity; epidermal growth factor, transforming growth factor (alpha), fibroblast growth factor, platelet-derived endothelial cell growth factor, insulin-like growth factor (IGF, e.g., IGF-I or IGF-II), glial derived growth neurotrophic factor, ciliary neurotrophic factor, nerve growth factor, bone growth/cartilage-inducing factor (alpha and beta), bone morphogenetic proteins (BMPs), interleukins (e.g., interleukin inhibitors or interleukin receptors, including interleukin 1 through interleukin 10), interferons (e.g., interferon alpha, beta and gamma), hematopoietic factors, including erythropoietin, granulocyte colony stimulating factor, macrophage colony stimulating factor and granulocyte-macrophage colony stimulating factor; tumor necrosis factors, transforming growth factors (beta), including beta-1, beta-2, beta-3, transforming growth factors (alpha), inhibin, and activin; and bone morphogenetic proteins such as OP-1, BMP-2 and BMP-7.

Hormones include estrogens (e.g., estradiol, estrone, estriol, diethylstibestrol, quinestrol, chlorotrianisene, ethinyl estradiol, mestranol), anti-estrogens (e.g., clomiphene, tamoxifen), progestins (e.g., medroxyprogesterone, norethindrone, hydroxyprogesterone, norgestrel), antiprogestin (mifepristone), androgens (e.g., testosterone cypionate, fluoxymesterone, danazol, testolactone), anti-androgens (e.g., cyproterone acetate, flutamide), thyroid hormones (e.g., triiodothyronne, thyroxine, propylthiouracil, methimazole, and iodixode), and pituitary hormones (e.g., corticotropin, sumutotropin, oxytocin, and vasopressin). Hormones are commonly employed in hormone replacement therapy and/or for purposes of birth control. Steroid hormones, such as prednisone, are also used as immunosuppressants and anti-inflammatories.

The biologically active agent is also desirably selected from the family of proteins known as the transforming growth factors-beta (TGF-β) superfamily of proteins, which includes the activins, inhibins, and bone morphogenetic proteins (BMPs). In an embodiment, the active agent includes at least one protein selected from the subclass of proteins known generally as BMPs, which have been disclosed to have osteogenic activity, and other growth and differentiation type activities. These BMPs include BMP proteins BMP-2, BMP-3, BMP-4, BMP-5, BMP-6 and BMP-7, disclosed for instance in U.S. Pat. Nos. 5,108,922; 5,013,649; 5,116,738; 5,106,748; 5,187,076; and 5,141,905; BMP-8, disclosed in PCT publication WO91/18098; and BMP-9, disclosed in PCT publication WO93/00432, BMP-10, disclosed in PCT application WO94/26893; BMP-11, disclosed in PCT application WO94/26892, or BMP-12 or BMP-13, disclosed in PCT application WO 95/16035; BMP-14; BMP-15, disclosed in U.S. Pat. No. 5,635,372; or BMP-16, disclosed in U.S. Pat. No. 5,965,403. Other TGF-β proteins which may be useful as the active agent in the calcium phosphate compositions of the invention include Vgr-2, Jones et al., *Mol. Endocrinol.* 6:1961 (1992), and any of the growth and differentiation factors (GDFs), including those described in PCT applications WO94/15965; WO94/15949; WO95/01801; WO95/01802; WO94/21681; WO94/15966; WO95/10539; WO96/01845; WO96/02559 and others. Also useful in the invention may be BIP, disclosed in WO94/01557; HP00269, disclosed in JP Publication number: 7-250688; and MP52, disclosed in PCT application WO93/16099. The disclosures of all of the above applications are incorporated herein by reference. A subset of BMPs which can be used in the invention include BMP-2, BMP-4, BMP-5, BMP-6, BMP-7, BMP-10, BMP-12, BMP-13, BMP-14, and MP52. The active agent is most preferably BMP-2, the sequence of which is disclosed in U.S. Pat. No. 5,013,649, the disclosure of which is incorporated herein by reference. Other osteogenic agents known in the art can also be used, such as teriparatide (Forteo™), Chrysalin®, prostaglandin E2, UM protein, osteogenin, or demineralized bone matrix (DBM), among others.

The biologically active agent may be synthesized chemically, recombinantly produced, or purified from a source in which the biologically active agent is naturally found. The active agent, if a TGF-β, such as a BMP or other dimeric protein, may be homodimeric, or may be heterodimeric with other BMPs (e.g., a heterodimer composed of one monomer each of BMP-2 and BMP-6) or with other members of the TGF-β superfamily, such as activins, inhibins and TGF-β1 (e.g., a heterodimer composed of one monomer each of a BMP and a related member of the TGF-β superfamily). Examples of such heterodimeric proteins are described for example in Published PCT Patent Application WO 93/09229, the specification of which is incorporated herein by reference.

Additional biologically active agents include the Hedgehog, Frazzled, Chordin, Noggin, Cerberus, and Follistatin proteins. These families of proteins are generally described in Sasai et al., *Cell* 79:779-790 (1994) (Chordin); PCT Patent Publication WO94/05800 (Noggin); and Fukui et al., *Devel. Biol.* 159:131 (1993) (Follistatin). Hedgehog proteins are described in WO96/16668; WO96/17924; and WO95/18856. The Frazzled family of proteins is a recently discovered family of proteins with high homology to the extracellular binding domain of the receptor protein family known as Frizzled. The Frizzled family of genes and proteins is described in Wang et al., *J. Biol. Chem.* 271:4468-4476 (1996). The active agent may also include other soluble receptors, such as the truncated soluble receptors disclosed in PCT patent publication WO95/07982. From the teaching of WO95/07982, one skilled in the art will recognize that truncated soluble receptors can be prepared for numerous other receptor proteins. The above publications are incorporated by reference herein.

The amount of the biologically active protein, e.g., an osteogenic protein, that is effective to stimulate a desired activity, e.g., increased osteogenic activity of present or infiltrating progenitor or other cells, will depend upon the size and nature of the defect being treated, as well as the carrier being employed. Generally, the amount of protein to be delivered is in a range of from about 0.1 to about 100 mg; preferably about 1 to about 100 mg; most preferably about 10 to about 80 mg.

Standard protocols and regimens for delivery of the above-listed agents are known in the art. Biologically active agents are introduced into the implant material in amounts that allow delivery of an appropriate dosage of the agent to the implant site. In most cases, dosages are determined using guidelines known to practitioners and applicable to the particular agent in question. The exemplary amount of biologically active agent to be included in the implant material of the invention is likely to depend on such variables as the type and extent of the condition, the overall health status of the particular patient, the formulation of the active agent, and the bioresorbability of the delivery vehicle used. Standard clinical trials may be used to optimize the dose and dosing frequency for any particular biologically active agent.

In an embodiment of all aspects of the invention, the composition can additionally contain autologous bone marrow or autologous platelet extracts.

In another embodiment of all of the above aspects, the PDGF and/or other growth factors can be obtained from natural sources, (e.g., platelets), or more preferably, produced by recombinant DNA technology. When obtained from natural sources, the PDGF and/or other growth factors can be obtained from a biological fluid. A biological fluid includes any treated or untreated fluid (including a suspension) associated with living organisms, particularly blood, including whole blood, warm or cold blood, and stored or fresh blood; treated blood, such as blood diluted with at least one physiological solution, including but not limited to saline, nutrient, and/or anticoagulant solutions; blood components, such as platelet concentrate (PC), apheresed platelets, platelet-rich plasma (PRP), platelet-poor plasma (PPP), platelet-free plasma, plasma, serum, fresh frozen plasma (FFP), components obtained from plasma, packed red cells (PRC), buffy coat (BC); blood products derived from blood or a blood component or derived from bone marrow; red cells separated from plasma and resuspended in physiological fluid; and platelets separated from plasma and resuspended in physiological fluid. The biological fluid may have been treated to remove some of the leukocytes before being processed according to the invention. As used herein, blood product or biological fluid refers to the components described above, and to similar blood products or biological fluids obtained by other means and with similar properties. In an embodiment, the PDGF is obtained from platelet-rich plasma (PRP). The preparation of PRP is described in, e.g., U.S. Pat. Nos. 6,649,072, 6,641,552, 6,613,566, 6,592,507, 6,558,307, 6,398,972, and 5,599,558, which are incorporated herein by reference.

In an embodiment of all aspects of the invention, the implant material delivers PDGF at the implant site for a duration of time greater than at least 1 day. In several embodiments, the implant material delivers PDGF at the implant site for at least 7, 14, 21, or 28 days. Preferably, the implant material delivers PDGF at the implant site for a time between about 1 day and 7, 14, 21, or 28 days. In another embodiment, the implant material delivers PDGF at the implant site for a time greater than about 1 day, but less than about 14 days.

By "bioresorbable" is meant the ability of the implant material to be resorbed or remodeled in vivo. The resorption process involves degradation and elimination of the original implant material through the action of body fluids, enzymes or cells. The resorbed materials may be used by the host in the formation of new tissue, or it may be otherwise re-utilized by the host, or it may be excreted.

By "differentiation factor" is meant a polypeptide, including a chain of at least 6 amino acids, which stimulates differentiation of one or more target cells into cells with cartilage or bone forming potential.

By "nanometer-sized particle" is meant a submicron-sized particle, generally defined as a particle below 1000 nanometers. A nanometer-sized particle is a solid particle material that is in an intermediate state between molecular and macron substances. A nanometer is defined as one billionth of a meter (1 nanometer=$10^9$ m). Nanometer material is known as the powder, fiber, film, or block having nanoscale size.

By "periodontium" is meant the tissues that surround and support the teeth. The periodontium supports, protects, and provides nourishment to the teeth. The periodontium consists of bone, cementum, alveolar process of the maxillae and mandible, periodontal ligament, and gingiva. Cementum is a thin, calcified layer of tissue that completely covers the dentin of the tooth root. Cementum is formed during the development of the root and throughout the life of the tooth and functions as an area of attachment for the periodontal ligament fibers. The alveolar process is the bony portion of the maxilla and mandible where the teeth are embedded and in which the tooth roots are supported. The alveolar socket is the cavity within the alveolar process in which the root of the tooth is held by the periodontal ligament. The bone that divides one socket from another is called the interdental septum. When multirooted teeth are present, the bone is called the interradicular septum. The alveolar process includes the cortical plate, alveolar crest, trabecular bone, and the alveolar bone proper.

By "promoting growth" is meant the healing of bone, periodontium, ligament, or cartilage, and regeneration of such tissues and structures. Preferably, the bone, periodontium, ligament, or cartilage is damaged or wounded and requires regeneration or healing.

By "promoting periodontium growth" is meant regeneration or healing of the supporting tissues of a tooth including alveolar bone, cementum, and interposed periodontal ligament, which have been damaged by disease or trauma.

By "purified" is meant a growth or differentiation factor, e.g., PDGF, which, prior to mixing with a carrier substance, is 95% or greater by weight, i.e., the factor is substantially free of other proteins, lipids, and carbohydrates with which it is naturally associated. The term "substantially purified" refers to a lesser purity of factor, having, for example, only 5%-95% by weight of the factor, preferably 65-95%. A purified protein preparation will generally yield a single major band on a polyacrylamide gel. Most preferably, the purified factor used in implant materials of the invention is pure as judged by amino-terminal amino acid sequence analysis. The term "partially purified" refers to PDGF that is provided in the context of PRP, PPP, FFP, or any other blood product that requires collection and separation, e.g., by centrifugation, to produce.

By way of example, a solution having ~1.0 mg/mL of PDGF, when ~50% pure, constitutes ~2.0 mg/mL of total protein.

The implant materials of this invention aid in regeneration of periodontium, at least in part, by promoting the growth of connective tissue, bone, and cementum. The implant materials can be prepared so that they directly promote the growth and differentiation of cells that produce connective tissue, bone, and cementum. Alternatively, the implant materials can be prepared so that they act indirectly by, e.g., attracting cells that are necessary for promoting the growth of connective tissue, bone, and cementum. Regeneration using a composition of this invention is a more effective treatment of periodontal diseases or bone wounds than that achieved using systemic antibiotics or surgical debridement alone.

The PDGF, polypeptide growth factors, and differentiation factors may be obtained from human tissues or cells, e.g., platelets, by solid phase peptide synthesis, or by recombinant DNA technology. Thus, by the term "polypeptide growth factor" or "differentiation factor," we mean tissue or cell-derived, recombinant, or synthesized materials. If the factor is a dimer, e.g., PDGF, the recombinant factor can be a recombinant heterodimer, made by inserting into cultured prokaryotic or eukaryotic cells DNA sequences encoding both subunits of the factor, and then allowing the translated subunits to be processed by the cells to form a heterodimer (e.g., PDGF-AB). Alternatively, DNA encoding just one of the subunits (e.g., PDGF B-chain or A-chain) can be inserted into cells, which then are cultured to produce the homodimeric factor (e.g., PDGF-BB or PDGF-AA homodimers). PDGF for use in the methods of the invention includes PDGF homo- and heterodimers, for example, PDGF-AA, PDGF-BB, PDGF-AB, PDGF-CC, and PDGF-DD, and combinations and derivatives thereof.

The concentration of PDGF or other growth factors of the invention can be determined by using, e.g., an enzyme-linked immunoassay, as described in, e.g., U.S. Pat. Nos. 6,221,625, 5,747,273, and 5,290,708, incorporated herein by reference, or any other assay known in the art for determining protein concentration. When provided herein, the molar concentration of PDGF is determined based on the molecular weight of PDGF dimer (e.g., PDGF-BB; MW=approximately 25 kDa).

The methods and implant materials of the invention can be used to heal bony wounds of mammals, e.g., fractures, implant recipient sites, and sites of periodontal disease. The implant materials promote connective tissue growth and repair and enhance bone formation compared to natural healing (i.e., no exogenous agents added) or healing supplemented by addition of systemic antibiotics. Unlike natural healing, conventional surgical therapy, or antibiotics, the implant materials of the invention prompt increased bone, connective tissue (e.g., cartilage and ligament), and cementum formation when applied to damaged or diseased tissues or to periodontal disease affected sites. The restoration of these tissues leads to an improved prognosis for the affected areas. The ability of these factors to stimulate new bone formation also makes it applicable for treating bony defects caused by other types of infection or surgical or accidental trauma.

Other features and advantages of the invention will be apparent from the following description of the embodiments thereof, and from the claims.

BRIEF DESCRIPTION OF THE DRAWINGS

FIGS. 1A-1G are photomicrographs showing the effect on bone formation 8 weeks following treatment. FIG. 1A is a photomicrograph showing the effect of surgery alone on bone formation. FIG. 1B is a photomicrograph showing the effect of β-TCP alone on bone formation. FIG. 1C is a photomicrograph showing the effect of β-TCP+0.3 mg/mL PDGF on bone formation. FIG. 1D is a photomicrograph showing the effect of β-TCP+1.0 mg/mL PDGF on bone formation. FIG. 1E is a photomicrograph showing the effect of demineralized freeze dried bone allograft (DFDBA) alone on bone formation. FIG. 1F is a photomicrograph showing the effect of demineralized freeze dried bone allograft (DFDBA)+0.3 mg/mL PDGF on bone formation. FIG. 1G is a photomicrograph showing the effect of demineralized freeze dried bone allograft (DFDBA)+1.0 mg/mL on bone formation.

FIG. 2A is a photomicrograph showing the effect of β-TCP alone on bone formation. FIG. 2B is a photomicrograph showing the effect of β-TCP+0.3 mg/mL PDGF on bone formation. FIG. 2C is a photomicrograph showing the effect of β-TCP+1.0 mg/mL PDGF on bone formation.

DETAILED DESCRIPTION

Figure 2C:
FIGS. 2A-2C are photomicrographs showing the effect on bone formation 16 weeks following treatment.

We now describe several embodiments of the invention. Two examples demonstrating the use of PDGF as a bone and periodontium healing agent are presented below.

EXAMPLES

Example I

Preparation of PDGF

Osseous wounds, e.g., following periodontal disease or trauma, are treated and periodontium, including bone, cementum, and connective tissue, are regenerated, according to the invention by combining partially purified or purified PDGF with any of the pharmaceutically acceptable carrier substances described above. Purified PDGF can be obtained from a recombinant source or from human platelets. Commercially available recombinant PDGF can be obtained from R&D Systems Inc. (Minneapolis, Minn.), BD Biosciences (San Jose, Calif.), and Chemicon, International (Temecula, Calif.). Partially purified and purified PDGF can also be prepared as follows:

Five hundred to 1000 units of washed human platelet pellets are suspended in 1M NaCl (2 ml per platelet unit) and heated at 100° C. for 15 minutes. The supernatant is then separated by centrifugation and the precipitate extracted twice with the 1 m NaCl.

The extracts are combined and dialyzed against 0.08M NaCl/0.01M sodium phosphate buffer (pH 7.4) and mixed overnight at 4° C. with CM-Sephadex C-50 equilibrated with the buffer. The mixture is then poured into a column (5×100 cm), washed extensively with 0.08M NaCl/0.01M sodium phosphate buffer (pH 7.4), and eluted with 1M NaCl while 10 ml fractions are collected.

Active fractions are pooled and dialyzed against 0.3M NaCl/0.01M sodium phosphate buffer (pH 7.4), centrifuged, and passed at 4° C. through a 2.5×25 cm column of blue sepharose (Pharmacia) equilibrated with 0.3M NaCl/0.01M sodium phosphate buffer (pH 7.4). The column is then washed with the buffer and partially purified PDGF eluted with a 1:1 solution of 1M NaCl and ethylene glycol.

The partially purified PDGF fractions are diluted (1:1) with 1M NaCl, dialyzed against 1M acetic acid, and lyophilized. The lyophilized samples are dissolved in 0.8M NaCl/0.01M sodium phosphate buffer (pH 7.4) and passed through a 1.2×40 cm column of CM-Sephadex C-50 equilibrated with the buffer. PDGF is then eluted with a NaCl gradient (0.08 to 1M).

The active fractions are combined, dialyzed against 1M acetic acid, lyophilized, and dissolved in a small volume of 1M acetic acid. 0.5 ml portions are applied to a 1.2×100 cm column of Biogel P-150 (100 to 200 mesh) equilibrated with 1M acetic acid. The PDGF is then eluted with 1M acetic acid while 2 mL fractions are collected.

Each active fraction containing 100 to 200 mg of protein is lyophilized, dissolved in 100 mL of 0.4% trifluoroacetic acid, and subjected to reverse phase high performance liquid chromatography on a phenyl Bondapak column (Waters). Elution with a linear acetonitrile gradient (0 to 60%) yields pure PDGF.

PDGF Made by Recombinant DNA Technology can be Prepared as Follows:

Platelet-derived growth factor (PDGF) derived from human platelets contains two polypeptide sequences (PDGF-B and PDGF-A polypeptides; Antoniades, H. N. and Hunkapiller, M., Science 220:963-965, 1983). PDGF-B is encoded by a gene localized on chromosome 7 (Betsholtz, C. et al., Nature 320:695-699), and PDGF-A is encoded by the sis oncogene (Doolittle, R. et al., Science 221:275-277, 1983) localized on chromosome 22 (Dalla-Favera, R., Science 218:686-688, 1982). The sis gene encodes the transforming protein of the Simian Sarcoma Virus (SSV) which is closely related to PDGF-2 polypeptide. The human cellular c-sis also encodes the PDGF-A chain (Rao, C. D. et al., Proc. Natl. Acad. Sci. USA 83:2392-2396, 1986). Because the two polypeptide chains of PDGF are coded by two different genes localized in separate chromosomes, the possibility exists that human PDGF consists of a disulfide-linked heterodimer of PDGF-B and PDGF-A, or a mixture of the two homodimers (PDGF-BB homodimer and PDGF-AA homodimer), or a mixture of the heterodimer and the two homodimers.

Mammalian cells in culture infected with the Simian Sarcoma Virus, which contains the gene encoding the PDGF-A chain, were shown to synthesize the PDGF-A polypeptide and to process it into a disulfide-linked homodimer (Robbins et al., *Nature* 305:605-608, 1983). In addition, the PDGF-A homodimer reacts with antisera raised against human PDGF. Furthermore, the functional properties of the secreted PDGF-A homodimer are similar to those of platelet-derived PDGF in that it stimulates DNA synthesis in cultured fibroblasts, it induces phosphorylation at the tyrosine residue of a 185 kD cell membrane protein, and it is capable of competing with human ($^{125}$I)-PDGF for binding to specific cell surface PDGF receptors (Owen, A. et al., *Science* 225:54-56, 1984). Similar properties were shown for the sis/PDGF-A gene product derived from cultured normal human cells (for example, human arterial endothelial cells), or from human malignant cells expressing the sis/PDGF-2 gene (Antoniades, H. et al., *Cancer Cells* 3:145-151, 1985).

The recombinant PDGF-B homodimer is obtained by the introduction of cDNA clones of c-sis/PDGF-B gene into mouse cells using an expression vector. The c-sis/PDGF-B clone used for the expression was obtained from normal human cultured endothelial cells (Collins, T., et al., *Nature* 216:748-750, 1985).

Use of PDGF

PDGF alone or in combination with other growth factors is useful for promoting bone healing, bone growth and regeneration or healing of the supporting structures of teeth injured by trauma or disease. It is also useful for promoting healing of a site of extraction of a tooth, for mandibular ridge augmentation, or at tooth implant sites. Bone healing would also be enhanced at sites of bone fracture or in infected areas, e.g., osteomyelitis, or at tumor sites. PDGF is also useful for promoting growth and healing of a ligament, e.g., the periodontal ligament, and of cementum.

In use, the PDGF or other growth or differentiation factor is applied directly to the area needing healing or regeneration. Generally, it is applied in a resorbable or non-resorbable carrier as a liquid or solid, and the site then covered with a bandage or nearby tissue. An amount sufficient to promote bone growth is generally between 500 ng and 5 mg for a 1 cm$^2$ area, but the upper limit is really 1 mg for a 1 cm$^2$ area, with a preferred amount of PDGF applied being 0.3 mg/mL.

Example II

Periodontal Regeneration with rhPDGF-BB Treated Osteoconductive Scaffolds

The effectiveness of PDGF in promoting periodontium and bone growth is demonstrated by the following study.

In Vivo Dog Study

The beagle dog is the most widely used animal model for testing putative periodontal regeneration materials and procedures (Wikesjo et al., *J. Clin. Periodontol.* 15:73-78, 1988; Wikesjo et al., *J. Clin. Periodontol.* 16:116-119, 1999; Cho et al., *J. Periodontol.* 66:522-530, 1995; Giannobile et al., *J. Periodontol.* 69:129-137, 1998; and Clergeau et al., *J. Periodontol.* 67:140-149, 1996). Plaque and calculus accumulation can induce gingival inflammation that may lead to marginal bone loss and the etiology of periodontitis in dogs and humans can be compared. In naturally occurring disease, however, there is a lack of uniformity between defects. Additionally, as more attention has been given to oral health in canine breeder colonies, it has become impractical to obtain animals with natural periodontal disease. Therefore, the surgically-induced horizontal Class III furcation model has become one of the most commonly used models to investigate periodontal healing and regeneration.

Beagle dogs with horizontal Class III furcation defects were treated using PDGF compositions of the invention. Fifteen adult beagle dogs contributed 60 treated defects. Forty-two defects were biopsied two months after treatment and fifteen defects were biopsied four months after treatment Defect Preparation The "critical-size" periodontal defect model as described by numerous investigators was utilized (see, e.g., Wikesjo, 1988 and 1999, supra; Giannobile, supra, Cho, supra, and Park et al., *J. Periodontol.* 66:462-477, 1995). Both mandibular quadrants in 16 male beagle dogs (2-3 years old) without general and oral health problems were used. One month prior to dosing, the animals were sedated with a subcutaneous injection of atropine (0.02 mg/kg) and acepromazine (0.2 mg/kg) approximately 30 minutes prior to being anesthetized with an IV injection of pentobarbital sodium (25 mg/kg). Following local infiltration of the surgical area with Lidocaine HCl plus epinephrine 1:100,000, full thickness mucoperiosteal flaps were reflected and the first and third premolars (P1 and P3) were extracted. Additionally, the mesial portion of the crown of the 1st molar was resected.

Alveolar bone was then removed around the entire circumference of P2 and P4, including the furcation areas using chisels and water-cooled carbide and diamond burs. Horizontal bone defects were created such that there was a distance of 5 mm from the fornix of the furcation to the crest of the bone. The defects were approximately 1 cm wide, depending on the width of the tooth. The roots of all experimental teeth were planed with curettes and ultrasonic instruments and instrumented with a tapered diamond bur to remove cementum. After the standardized bone defects were created the gingival flaps were sutured to achieve primary closure. The animals were fed a soft diet and received daily chlorhexidine rinses for the duration of the study.

Application of Graft Material

The periodontal defects of P2 and P4 in each mandibular quadrant of the 15 animals were randomized prior to treatment using sealed envelopes. About four weeks after defect preparation, animals were re-anesthetized as described above and full thickness flaps were reflected in both mandibular quadrants. A notch was placed in the tooth root surfaces at the residual osseous crest using a ½ round bur to serve as a future histologic reference point. The sites were irrigated with sterile saline and the roots were treated with citric acid as described previously for the purpose of decontamination and removal of the smear layer (See, e.g., Cho, supra, and Park, supra). During this period an amount of β-TCP or DFDBA sufficient to fill the periodontal defect was saturated with a solution of rhPDGF-BB solution (0.3 or 1.0 mg/ml) and the rhPDGF-BB/graft mixture was allowed to sit on the sterile surgical stand for about ten minutes. The rhPDGF-BB saturated graft was then packed into the defect with gentle pressure to the ideal level of osseous regeneration.

After implantation of the graft material, the mucoperiosteal flaps were sutured approximately level to the cementoenamel junction (CEJ) using interproximal, interrupted 4.0 expanded polytetrafluoroethylene (ePTFE) sutures. Following suturing of the flaps chlorhexidine gluconate gel was gently placed around the teeth and gingivae.

Treatment and Control Groups

Defects received either:
1. β-TCP
2. β-TCP plus rhPDGF-BB (0.3 mg/ml rhPDGF-BB)
3. β-TCP plus rhPDGF-BB (1.0 mg/ml rhPDGF-BB)
4. Dog DFDBA
5. Dog DFDBA plus rhPDGF-BB (0.3 mg/ml rhPDGF-BB)
6. Dog DFDBA plus rhPDGF-BB (1.0 mg/ml rhPDGF-BB)
7. Sham surgery (treated by open flap debridement only, no graft)

Six defects per treatment group were biopsied at two months (42 total sites). In addition, five defects in treatment groups 1, 2, and 3 were biopsied at four months (15 total sites).

TABLE 2

Experimental design

| GROUP NO. | NO. OF TEST SITES | TREATMENT | TIME POINTS |
|---|---|---|---|
| 1 | 11 | β-TCP alone | 8 & 16 weeks<br>n = 6 for 8 wk<br>n = 5 for 16 wk |
| 2 | 11 | β-TCP + 0.3 mg/ml rhPDGF-BB | 8 & 16 weeks<br>n = 6 for 8 wk<br>n = 5 for 16 wk |
| 3 | 11 | β-TCP + 1.0 mg/ml rhPDGF-BB | 8 & 16 weeks<br>n = 6 for 8 wk<br>n = 5 for 16 wk |
| 4 | 6 | DFDBA alone | 8 weeks |
| 5 | 6 | DFDBA + 0.3 mg/ml rhPDGF-BB | 8 weeks |
| 6 | 6 | DFDBA + 1.0 mg/ml rhPDGF-BB | 8 weeks |
| 7 | 6 | Surgery, no graft | 8 weeks |

Accordingly, at 8 weeks there are 7 groups divided among 42 sites in 11 dogs. At 16 weeks, there are 3 groups divided among 15 sites in 4 dogs (one dog received two treatment surgeries staggered eight weeks apart and thus contributed two sites to each the 8 and 16 week time points).

Post-Surgical Treatment

The surgical sites were protected by feeding the dogs a soft diet during the first 4 weeks post-operative. To insure optimal healing, systemic antibiotic treatment with penicillin G benzathine was provided for the first two weeks and plaque control was maintained by daily irrigation with 2% chlorhexidine gluconate throughout the experiment. Sutures were removed after 3 weeks.

Data Collection

Rationale for Data Collection Points

The eight week time point was chosen because this is the most common time point reported for this model in the literature and therefore there are substantial historical data. For example, Wikesjo et al., supra, and Giannobile et al., supra, also chose 8 weeks to assess the regenerative effects of BMP-2 and OP-1, respectively, in the same model. Additionally, Park et al., supra, evaluated the effect or rhPDGF-BB applied directly to the conditioned root surface with and without GTR membranes in the beagle dog model at 8 weeks. These studies, strongly suggest that the 8 week period should be optimal for illustrating potential significant effects among the various treatment modalities.

The sixteen week time point was chosen to assess long-term effects of growth factor treatment. Previous studies (Park et al., supra) suggest that by this time there is substantial spontaneous healing of the osseous defects. Nevertheless, it is possible to assess whether rhPDGF-BB treatment leads to any unusual or abnormal tissue response, such as altered bone remodeling, tumorgenesis or root resorption.

Biopsies and Treatment Assessments

At the time of biopsy, the animals were perfused with 4% paraformaldehyde and sacrificed. The mandibles were then removed and placed in fixative. Periapical radiographs were taken and the treated sites were cut into individual blocks using a diamond saw. The coded (blinded) blocks were wrapped in gauze, immersed in a solution of 4% formaldehyde, processed, and analyzed.

During processing the biopsies were dehydrated in ethanol and infiltrated and embedded in methylmethacrylate. Undecalcified sections of approximately 300 μm in thickness were obtained using a low speed diamond saw with coolant. The sections were glued onto opalescent acrylic glass, ground to a final thickness of approximately 80 μm, and stained with toludine blue and basic fuchsin. Step serial sections were obtained in a mesiodistal plane.

Histomorphometric analyses were performed on the masked slides. The following parameters were assessed:

1. Length of Complete New Attachment Apparatus (CNAA): Periodontal regeneration measured as the distance between the coronal level of the old bone and the coronal level of the new bone, including only that new bone adjacent to new cementum with functionally oriented periodontal ligament between the new bone and new cementum.

2. New Bone Fill (NB): Measured as the cross-sectional area of new bone formed within the furcation.

3. Connective Tissue fill (CT): Measured as the area within the furcation occupied by gingival connective tissue.

4. Void (VO): The area of recession where there is an absence of tissue.

Results

A. Clinical Observations

Clinically, all sites healed well. There was an impression that the sites treated with rhPDGF-BB healed more quickly, as indicated by the presence of firm, pink gingivae within one week post-operatively. There were no adverse events experienced in any treatment group as assessed by visual inspection of the treated sites. There appeared to be increased gingival recession in groups that received β-TCP or DFDBA alone.

B. Radiographic Observations

Radiographically, there was evidence of increased bone formation at two months as judged by increased radiopacity in Groups 2, 3 (β-TCP+rhPDGF-BB 0.3 and 1.0 mg/ml, respectively) and 6 (DFDBA+rhPDGF-BB 1.0 mg/ml) compared to the other groups (FIGS. 1A-G). At four months, there was evidence of increased bone formation in all groups compared to the two month time point. There was no radiographic evidence of any abnormal bone remodeling, root resorption, or ankylosis in any group.

TABLE 3

Radiographic results. Rank order.

| QUALITATIVE ASSESSMENT OF BONE FILL AT 8 WKS* | TREATMENT |
|---|---|
| 6 | β-TCP alone |
| 1 | β-TCP + 0.3 mg/ml rhPDGF |
| 2 | β-TCP + 1.0 mg/ml rhPDGF |
| 7 | DFDBA alone |

TABLE 3-continued

Radiographic results. Rank order.

| QUALITATIVE ASSESSMENT OF BONE FILL AT 8 WKS* | TREATMENT |
|---|---|
| 5 | DFDBA + 0.3 mg/ml rhPDGF |
| 3 | DFDBA + 1.0 mg/ml rhPDGF |
| 4 | Surgery, no graft |

*1 = most fill; 7 = least fill

C. Histomorphometric Analyses:

Histomorphometric assessment of the length of new cementum, new bone, and new periodontal ligament (CNAA) as well as new bone fill, connective tissue fill, and void space were evaluated and are expressed as percentages. In the case of CNAA, values for each test group represent the CNAA measurements (length in mm)/total available CNAA length (in mm)×100%. Bone fill, connective tissue fill and void space were evaluated and are expressed as percentages of the total furcation defect area.

One-way analysis of variance (ANOVA) was used to test for overall differences among treatment groups, and pairwise comparisons were made using the student's t-test. Significant differences between groups were found upon analyses of the coded slides. Table 4 shows the results at two months.

TABLE 4

Two month histometric analyses

| GROUP NO. | TREATMENT | % CNAA PERIODONTAL REGENERATION | % BONE FILL | % CONNECTIVE TISSUE FILL | % VOID |
|---|---|---|---|---|---|
| 1 | β-TCP alone | 37.0 ± 22.8 ** | 28.0 ± 29.5 | 36.0 ± 21.5 | 12.0 ± 17.9 |
| 2 | β-TCP + 0.3 mg/ml rhPDGF | 59.0 ± 19.1 *, † | 84.0 ± 35.8 †, ‡ | 0.0 ± 0.0 | 8.0 ± 17.9 |
| 3 | β-TCP + 1.0 mg/ml rhPDGF | 46.0 ± 12.3 * | 74.2 ± 31.7 ‡ | 0.0 ± 0.0 | 0.0 ± 0.0 |
| 4 | DFDBA alone | 13.4 ± 12.0 | 6.0 ± 8.9 | 26.0 ± 19.5 | 30.0 ± 27.4 |
| 5 | DFDBA + 0.3 mg/ml rhPDGF | 21.5 ± 13.3 | 20.0 ± 18.7 | 36.0 ± 13.4 | 18.0 ± 21.7 |
| 6 | DFDBA + 1.0 mg/ml rhPDGF | 29.9 ± 12.4 | 46.0 ± 23.0 ≠ | 26.0 ± 5.48 | 8.0 ± 13.04 |
| 7 | Sham Surgery, no graft | 27.4 ± 15.0 | 34.0 ± 27.0 | 48.0 ± 35.64 | 10.0 ± 22.4 |

* Groups 2 and 3 significantly greater ($p < 0.05$) than Groups 4 and 7.
** Group 1 significantly greater ($p < 0.05$) than Group 4.
† Group 2 significantly greater ($p < 0.05$) than Group 5.
‡ Groups 2 and 3 significantly greater than Groups 1, 4 and 7.
≠ Group 6 significantly greater than Group 4.

The mean percent periodontal regeneration (CNAA) in the surgery without grafts and surgery plus β-TCP alone groups were 27% and 37%, respectively. In contrast, β-TCP groups containing rhPDGF-BB exhibited significantly greater periodontal regeneration ($p<0.05$) than surgery without grafts or DFDBA alone (59% and 46% respectively for the 0.3 and 1.0 mg/ml concentrations versus 27% for surgery alone and 13% for DFDBA alone). Finally, the β-TCP group containing 0.3 mg/ml rhPDGF-BB demonstrated significantly greater periodontal regeneration ($p<0.05$) than the same concentration of rhPDGF-BB combined with allograft (59% versus 21%).

Bone fill was significantly greater ($p<0.05$) in the β-TCP+ 0.3 mg/ml rhPDGF-BB (84.0%) and the β-TCP+1.0 mg/ml rhPDGF-BB (74.2%) groups than in the β-TCP alone (28.0%), surgery alone (34%) or DFDBA alone (6%) treatment groups. There was also significantly greater bone fill ($p<0.05$) for the β-TCP+0.3 mg/ml rhPDGF-BB group compared to the DFDBA+0.3 mg/ml rhPDGF-BB group (84% and 20% respectively).

The group of analyses examining the 8-week data from the DFDBA groups and the surgery alone group (Groups 4, 5, 6, and 7) demonstrated no statistically significant differences between the DFDBA groups and surgery alone for periodontal regeneration (CNAA). There was a trend toward greater regeneration for those sites treated with the 1.0 mg/ml rhPDGF-BB enhanced DFDBA versus DFDBA alone. There was significantly greater bone fill ($p<0.05$) for sites treated with DFDBA+1.0 mg/ml rhPDGF-BB than DFDBA alone (46 and 6% respectively). There was a trend toward greater bone fill for sites treated with DFDBA containing 0.3 mg/ml rhPDGF-BB compared to DFDBA alone or surgery alone. However, sites treated with DFDBA alone demonstrated less bone fill into the defect than surgery alone (6 and 34%, respectively), with most of the defect being devoid of any fill or fill consisting of gingival (soft) connective tissue.

At four months following treatment, there remained significant differences in periodontal regeneration. β-TCP alone, as a result of extensive ankylosis, resulted in 36% regeneration, while the sites treated with β-TCP containing rhPDGF-BB had a mean regeneration of 58% and 49% in the 0.3 and 1.0 mg/ml rhPDGF-BB concentrations. Substantial bone fill was present in all three treatment groups. β-TCP alone resulted in 70% bone fill, β-TCP plus 0.3 mg/ml rhPDGF yielded 100% fill while the 1.0 mg/ml rhPDGF group had 75% fill.

D. Histologic Evaluation

Histologic evaluation was performed for all biopsies except one, in which evaluation was not possible due to difficulties encountered during processing.

Representative photomicrographs are shown in FIGS. 1A-G and 2A-C. FIG. 1A shows results from a site treated with surgery alone (no grafts). This specimen demonstrates limited periodontal regeneration (new bone (NB), new cementum (NC), and periodontal ligament (PDL)) as evidenced in the area of the notches and extending only a short distance coronally. The area of the furcation is occupied primarily by dense soft connective tissue (CT) with minimal new bone (NB) formation.

For sites treated with β-TCP alone (FIG. 1B) there is periodontal regeneration, similar to that observed for the surgery alone specimen, that extends from the base of the notches for a short distance coronally. As was seen in the surgery alone specimens, there was very little new bone formation with the greatest area of the furcation being occupied by soft connective tissue.

In contrast, FIG. 1C illustrates results obtained for sites treated with β-TCP+0.3 mg/ml rhPDGF-BB. Significant periodontal regeneration is shown with new bone, new cementum, and periodontal ligament extending along the entire surface of the furcation. Additionally, the area of the furcation is filled with new bone that extends the entire height of the furcation to the fornix.

Representative results for sites treated with β-TCP+1.0 mg/ml rhPDGF-BB are shown in FIG. 1D. While there is significant periodontal regeneration in the furcation, it does not extend along the entire surface of the furcation. There is new bone formation present along with soft connective tissue that is observed at the coronal portion of the defect along with a small space which is void of any tissue (VO) at the fornix of the furcation.

Figure 2B:
Figure 2A:

FIGS. 2A, 2B, and 2C illustrate results obtained for the allograft treatment groups. Representative results for the DFDBA alone group (FIG. 2A) shows very poor periodontal regeneration that is limited to the area of the notches extending only slightly in a coronal direction. New bone formation is limited and consists of small amounts of bone formation along the surface of residual DFDBA graft material (dark red staining along lighter pink islands). Additionally, the new bone is surrounded by extensive soft connective tissue that extends coronally to fill a significant area within the furcation. Finally, a large void space extends from the coronal extent of the soft connective tissue to the fornix of the furcation.

Histologic results for the DFDBA+0.3 and 1.0 mg/ml rhPDGF-BB are shown in FIGS. 2B and 2C, respectively. Both groups demonstrate greater periodontal regeneration compared to DFDBA alone with a complete new attachment apparatus (new bone, new cementum, and periodontal ligament) extending from the base of the notches in the roots for a short distance coronally (arrows). They also had greater bone fill within the area of the furcation, although there was significant fill of the furcation with soft connective tissue.

Conclusions

Based on the results of the study, treatment of a periodontal defect using rhPDGF-BB at either 0.3 mg/mL or 1.0 mg/mL in combination with a suitable carrier material (e.g., β-TCP) results in greater periodontal regeneration than the current products or procedures, such as grafts with β-TCP or bone allograft alone, or periodontal surgery without grafts.

Treatment with the 0.3 mg/mL and 1.0 mg/mL concentration of rhPDGF resulted in periodontal regeneration. The 0.3 mg/ml concentration of rhPDGF demonstrated greater periodontal regeneration and percent bone fill as compared to the 1.0 mg/ml concentration of rhPDGF when mixed with β-TCP.

β-TCP was more effective than allograft when mixed with rhPDGF-BB at any concentration. The new bone matured (remodeled) normally over time (0, 8, and 16 weeks) in all groups. There was no increase in ankylosis or root resorption in the rhPDGF groups. In fact, sites receiving rhPDGF-BB tended to have less ankylosis than control sites. This finding may result from the fact that rhPDGF-BB is mitogenic and chemotactic for periodontal ligament cells.

Materials and Methods

Materials Utilized: Test and Control Articles

The β-TCP utilized had a particle-size (0.25 mm-1.0 mm) that was optimized for periodontal use. Based on studies using a canine model, administered β-TCP is ~80% resorbed within three months and is replaced by autologous bone during the healing process.

The DFDBA was supplied by Musculoskeletal Transplant Foundation (MTF). The material was dog allograft, made by from the bones of a dog that was killed following completion of another study that tested a surgical procedure that was deemed to have no effect on skeletal tissues.

Recombinant hPDGF-BB was supplied by BioMimetic Pharmaceuticals and was manufactured by Chiron, Inc, the only supplier of FDA-approved rhPDGF-BB for human use. This rhPDGF-BB was approved by the FDA as a wound healing product under the trade name of Regranex®.

One ml syringes containing 0.5 ml of sterile rhPDGF-BB at two separate concentrations prepared in conformance with FDA standards for human materials and according to current applicable Good Manufacturing Processes (cGMP). Concentrations tested included 0.3 mg/ml and 1.0 mg/ml.

β-TCP was provided in vials containing 0.5 cc of sterile particles.

DFDBA was provided in 2.0 ml syringes containing 1.0 cc of sterile, demineralized freeze-dried dog bone allograft.

Material Preparation

At the time of the surgical procedure, the final implanted grafts were prepared by mixing the rhPDGF-BB solution with the matrix materials. Briefly, an amount of TCP or allograft sufficient to completely fill the osseous defect was placed into a sterile dish. The rhPDGF-BB solution sufficient to completely saturate the matrix was then added, the materials were mixed and allowed to sit on the surgical tray for about 10 minutes at room temperature prior to being placed in the osseous defect.

A 10 minute incubation time with the β-TCP material is sufficient to obtain maximum adsorption of the growth factor (see Appendix A). This is also an appropriate amount of time for surgeons in a clinical setting to have prior to placement of the product into the periodontal defect. Similarly, in a commercial market, the rhPDGF-BB and the matrix material can be supplied in separate containers in a kit and that the materials can be mixed directly before placement. This kit concept would greatly simplify product shelf life/stability considerations.

Example III

Use of PDGF for the Treatment of Periodontal Bone Defects in Humans

Recombinant human PDGF-BB (rhPDGF-BB) was tested for its effect on the regeneration of periodontal bone in human subjects. Two test groups were administered rhPDGF-BB at either 0.3 mg/mL (Group I) or 1.0 mg/mL (Group II). rhPDGF-BB was prepared in sodium acetate buffer and administered in a vehicle of beta-tricalcium phosphate (β-TCP). The control group, Group III, was administered β-TCP in sodium acetate buffer only.

The objective of clinical study was to evaluate the safety and effectiveness of graft material comprising β-TCP and rhPDGF-BB at either 0.3 mg/mL or 1.0 mg/mL in the management of one (1) to three (3) wall intra-osseous periodontal defects and to assess its regenerative capability in bone and soft tissue.

Study Design and Duration of Treatment

The study was a double-blind, controlled, prospective, randomized, parallel designed, multi-center clinical trial in subjects who required surgical intervention to treat a bone defect adjacent to the natural dentition. The subjects were randomized in equal proportions to result in three (3) treatment groups of approximately 60 subjects each (180 total). The duration of the study was six (6) months following implantation of the study device. The study enrolled 180 subjects.

Diagnosis and Main Entry Criteria

Male and female subjects, 25-75 years of age, with advanced periodontal disease in at least one site requiring surgical treatment to correct a bone defect were admitted to the study. Other inclusion criteria included: 1) a probing pocket depth measuring 7 mm or greater at the baseline visit; 2) after surgical debridement, 4 mm or greater vertical bone defect (BD) with at least 1 bony wall; 3) sufficient keratinized tissue to allow complete tissue coverage of the defect; and, 4) radiographic base of defect at least 3 mm coronal to the apex of the tooth. Subjects who smoked up to 1 pack a day and who had teeth with Class I & II furcation involvement were specifically allowed.

Dose and Mode of Administration

All treatment kits contained 0.25 g of β-TCP (an active control) and either 0.5 mL sodium acetate buffer solution alone (Group III), 0.3 mg/mL rhPDGF-BB (Group I), or 1.0 mg/mL rhPDGF-BB (Group II).

Following thorough debridement and root planing, the test solution was mixed with β-TCP in a sterile container, such that the β-TCP was fully saturated. Root surfaces were conditioned using either tetracycline, EDTA, or citric acid. The hydrated graft was then packed into the osseous defect and the tissue flaps were secured with interdental sutures to achieve complete coverage of the surgical site.

Effectiveness Measurement

The primary effectiveness measurement included the change in clinical attachment level (CAL) between baseline and six months post-surgery (Group I vs. Group III). The secondary effectiveness measurements consisted of the following outcomes: 1) linear bone growth (LBG) and % bone fill (% BF) from baseline to six months post-surgery based on the radiographic assessments (Group I and Group II vs. Group III); 2) change in CAL between baseline and six months post-surgery (Group II vs. Group III); 3) probing pocket depth reduction (PDR) between baseline and six months post-surgery (Group I and Group II vs. Group III); 4) gingival recession (GR) between baseline and six months post-surgery (Group I and Group II vs. Group III); 5) wound healing (WH) of the surgical site during the first three weeks post-surgery (Group I and Group II vs. Group III); 6) area under the curve for the change in CAL between baseline and three (3) and six (6) months (Group I and Group II vs. Group III); 7) the 95% lower confidence bound (LCB) for % BF at six (6) months post-surgery (Groups I, II, and III vs. demineralized freeze-dried bone allograft (DFDBA) as published in the literature; Parashis et al., J. Periodontol. 69:751-758, 1998); 8) the 95% LCB for linear bone growth at six (6) months post-surgery (Groups I, II, and III vs. demineralized freeze-dried bone allograft (DFDBA) as published in the literature; Persson et al., J. Clin. Periodontol. 27:104-108, 2000); 9) the 95% LCB for the change in CAL between baseline and six (6) months (Groups I, II, and II vs. EMDOGAIN®-PMA P930021, 1996); and 10) the 95% LCB for the change in CAL between baseline and six (6) months (Groups I, II and III vs. PEPGEN PMA P990033, 1999).

Statistical Methods

Safety and effectiveness data were examined and summarized by descriptive statistics. Categorical measurements were displayed as counts and percents, and continuous variables were displayed as means, medians, standard deviations and ranges. Statistical comparisons between the test product treatment groups (Groups I and II) and the control (Group III) were made using Chi-Square and Fisher's Exact tests for categorical variables and t-tests or Analysis of Variance Methods (ANOVA) for continuous variables. Comparisons between treatment groups for ordinal variables were made using Cochran-Mantel-Haenszel methods. A p≤0.05 (one sided) was considered to be statistically significant for CAL, LBG and % BF.

Safety data were assessed by the frequency and severity of adverse events as evaluated clinically and radiographically. There were no significant differences between the three treatment groups at baseline. There were also no statistically significant differences observed in the incidence of adverse events (AEs; all causes) among the three treatment groups. The safety analysis did not identify any increased risk to the subject due to implantation of the graft material.

Summary of Effectiveness Results

The results from the statistical analyses revealed both clinically and statistically significant benefits for the two treatment groups (Groups I and II), compared to the active control of β-TCP alone (Group III) and historical controls including DFDBA, EMDOGAIN®, and PEPGEN P-15™.

At three months post-surgery, a statistically significant CAL gain from baseline was observed in favor of Group I versus Group III (p=0.041), indicating that there are significant early benefits of PDGF on the gain in CAL. At six months post-surgery, this trend continued to favor Group I over Group III, although this difference was not statistically significant (p=0.200). The area under the curve analysis (AUC) which represents the cumulative effect (i.e. speed) for CAL gain between baseline and six months approached statistical significance favoring Group I in comparison to Group III (p=0.054). Further, the 95% lower confidence bound (LCB) analyses for all treatment groups substantiated the effectiveness of Groups I and II compared to the CAL gains observed at six (6) months for EMDOGAIN® and PEPGEN P-15™.

In addition to the observed clinical benefits of CAL, radiographic analyses including Linear Bone Growth (LBG) and Percent Bone Fill (% BF), revealed statistically significant improvement in bone gain for Groups I and II vs. Group III. % BF was defined as the percent of the original osseous defect filled with new bone as measured radiographically. LBG showed significant improvement in Group I (2.5 mm) when compared to Group III (0.9 mm, p<0.001). LBG was also significant for Group II (1.5 mm) when compared to Group III (p=0.021).

Percent Bone Fill (% BF) was significantly increased at six months post-surgical in Group I (56%) and Group II (34%) when compared to Group III (18%), for a p<0.001 and p=0.019, respectively. The 95% lower bound of the confidence interval at Six months post-surgery, for both linear bone growth and % bone fill, substantiated the effectiveness of Groups I and II compared to the published radiographic results for DFDBA, the most widely used material for periodontal grafting procedures.

At three months, there was significantly less Gingival Recession (GR) (p=0.041) for Group I compared to Group III consistent with the beneficial effect observed with CAL. No statistically significant differences were observed in PDR and GR at six months. Descriptive analysis of the number of sites exhibiting complete wound healing (WH) at three weeks revealed improvements in Group I (72%) vs. Group II (60%) and Group III (55%), indicating a trend toward improved healing.

To assess the cumulative beneficial effect for clinical and radiographic outcomes, a composite effectiveness analysis was performed to determine the percent of patients with a successful outcome as defined by CAL>2.7 mm and LBG>1.1 mm at six (6) months. The CAL and LBG benchmarks of success were established by the mean levels achieved for these parameters by the implanted grafts, as identified in the "Effectiveness Measures" section above. The results showed that 61.7% of Group I patients and 37.9% of Group II patients met or exceeded the composite benchmark for success compared to 30.4% of Group III patients, resulting in a statistically significant benefit of Group I vs. Group III ($p<0.001$). % BF revealed similar benefits for Group I (70.0%) vs. Group III (44.6%) for p-value of 0.003.

In summary, Group I achieved statistically beneficial results for CAL and GR at three (3) months as well as LBG and % BF at six (6) months, compared to the β-TCP alone active control group (Group III). The clinical significance of these results is further confirmed by comparison to historical controls. It is concluded that PDGF-containing graft material was shown to achieve clinical and radiographic effectiveness by six months for the treatment of periodontal osseous defects.

TABLE 5

Summary of PDGF Graft Effectiveness

| ENDPOINT | | GROUP I | GROUP II | GROUP III |
|---|---|---|---|---|
| CAL Gain (mm): 3 months | | 3.8 | 3.4 | 3.3 |
| | | (p = 0.04) | (p = 0.40) | |
| CAL: AUC Analysis (mm × wk) | | 67.5 | 61.8 | 60.1 |
| | | (p = 0.05) | (p = 0.35) | |
| CAL (mm): 95% LCB 6 months (vs 2.7 mm for EMDOGAIN & 1.1 mm for PEPGEN) | | 3.3 | 3.2 | 3.1 |
| GR (mm): 3 months | | 0.5 | 0.7 | 0.9 |
| | | (p = 0.04) | (p = 0.46) | |
| LBG (mm): 6 months | | 2.5 | 1.5 | 0.9 |
| | | (p < 0.001) | (p = 0.02) | |
| % BF: 6 months | | 56.0 | 33.9 | 17.9 |
| | | (p < 0.001) | (p = 0.02) | |
| Composite Analysis (% Success) | CAL-LBG | 61.7% | 37.9% | 30.4% |
| | | (p < 0.001) | (p = 0.20) | |
| | CAL-% BF | 70.0% | 55.2% | 44.6% |
| | | (p = 0.003) | (p = 0.13) | |

Graft material (i.e., β-TCP) containing PDGF at 0.3 mg/mL and at 1.0 mg/mL was shown to be safe and effective in the restoration of alveolar bone and clinical attachment around teeth with moderate to advanced periodontitis in a large, randomized clinical trial involving 180 subjects studied for up to 6 months. These conclusions are based upon validated radiographic and clinical measurements as summarized below.

Consistent with the biocompatibility data of the PDGF-containing graft material, discussed above, and the historical safe use of each individual component (i.e., β-TCP alone or PDGF alone), the study revealed no evidence of either local or systemic adverse effects. There were no adverse outcomes attributable to the graft material, which was found to be safe.

Conclusion

Implantation of β-TCP containing PDGF at either 0.3 mg/mL or 1.0 mg/mL was found to be an effective treatment for the restoration of soft tissue attachment level and bone as shown by significantly improved CAL at 3 months compared to the active control. Our findings are also consistent with the AUC analysis that showed an improvement in CAL gain between baseline and six months. Implantation of β-TCP containing PDGF at either 0.3 mg/mL or 1.0 mg/mL was also found to be an effective treatment based on significantly improved LBG and % BF compared to the active control. Significantly improved clinical outcomes as shown by the composite analysis of both soft and hard tissue measurements compared to the β-TCP alone active control also demonstrate the effectiveness of the treatment protocol described above. Finally, the results of administering β-TCP containing PDGF at either 0.3 mg/mL or 1.0 mg/mL were found to exceed established benchmarks of effectiveness both clinically and radiographically.

The results of this trial together with extensive and confirmatory data from in vitro, animal and human studies demonstrate that PDGF-containing graft material stimulates soft and hard tissue regeneration in periodontal defects, although the effects were more significant when PDGF in the range of 0.1 to 1.0 mg/mL (e.g., 0.1 mg/mL, 0.3 mg/mL, or 1.0 mg/mL) was administered in the graft material. Moreover, PDGF administered in the graft material in the amount of 0.3 mg/mL effectively regenerated soft tissue and bone.

Other embodiments are within the following claims.

What is claimed is:
1. An implant material comprising:
   a) a porous calcium phosphate, wherein the calcium phosphate comprises interconnected pores, a porosity greater than 40%, and particles having a size ranging from about 100 microns to about 5000 microns,
   b) a biocompatible binder comprising polysaccharides, nucleic acids, carbohydrates, proteins, polypeptides, or any mixture thereof, and
   c) a solution comprising a platelet derived growth factor (PDGF) at a concentration ranging from about 0.1 mg/mL to about 1.0 mg/mL in a buffer,
   wherein the implant material does not comprise demineralized freeze-dried bone allograft.
2. The implant material of claim 1, wherein the PDGF comprises recombinant PDGF.
3. The implant material of claim 1, wherein the PDGF comprises recombinant human PDGF-BB.
4. The implant material of claim 1, wherein the solution comprises PDGF at a concentration of about 0.3 mg/mL in a buffer.
5. The implant material of claim 1, wherein the solution comprises PDGF at a concentration ranging from about 0.25 mg/mL to about 0.5 mg/mL in a buffer.
6. The implant material of claim 1, wherein the solution comprises PDGF at a concentration ranging from about 0.2 mg/mL to about 0.75 mg/mL in a buffer.
7. The implant material of claim 1, wherein the calcium phosphate comprises particles having a size ranging from about 100 microns to about 3000 microns.
8. The implant material of claim 1, wherein the calcium phosphate comprises particles having a size ranging from of about 250 microns to about 1000 microns.
9. The implant material of claim 1, wherein the implant material is resorbable such that at least 80% of the calcium phosphate is resorbed within one year of being implanted.
10. The implant material of claim 1, wherein the solution is adsorbed into or absorbed by the calcium phosphate.
11. The implant material of claim 1, wherein the calcium phosphate is capable of absorbing an amount of the solution comprising PDGF that is equal to at least about 25% of the calcium phosphate's own weight.

12. The implant material of claim 1, wherein the calcium phosphate is capable of absorbing an amount of the solution comprising PDGF that is equal to at least about 50% of the calcium phosphate's own weight.

13. The implant material of claim 1, wherein the calcium phosphate is capable of absorbing an amount of the solution comprising PDGF that is equal to at least about 200% of the calcium phosphate's own weight.

14. The implant material of claim 1, wherein the calcium phosphate is capable of absorbing an amount of the solution comprising PDGF that is equal to at least about 300% of the calcium phosphate's own weight.

15. The implant material of claim 1, wherein the calcium phosphate comprises β-tricalcium phosphate.

16. The implant material of claim 1, wherein the biocompatible binder comprises poly(α-hydroxy acids), poly(lactones), poly(amino acids), poly(anhydrides), poly(orthoesters), poly(anhydride-co-imides), poly(orthocarbonates), poly(α-hydroxy alkanoates), poly(dioxanones), poly(phosphoesters), polylactic acid, poly(L-lactide) (PLLA), poly(D, L-lactide) (PDLLA), polyglycolide (PGA), poly(lactide-co-glycolide) (PLGA), poly(L-lactide-co-D, L-lactide), poly(D, L-lactide-co-trimethylene carbonate), polyglycolic acid, polyhydroxybutyrate (PHB), poly(ε-caprolactone), poly(δ-valerolactone), poly(γ-butyrolactone), poly(caprolactone), polyacrylic acid, polycarboxylic acid, poly(allylamine hydrochloride), poly(diallyldimethylammonium chloride), poly(ethyleneimine), polypropylene fumarate, polyvinyl alcohol, polyvinylpyrrolidone, polyethylene, polymethylmethacrylate, carbon fibers, poly(ethylene glycol), poly(ethylene oxide), poly(vinyl alcohol), poly(vinylpyrrolidone), poly(ethyloxazoline), poly(ethylene oxide)-co-poly(propylene oxide) block copolymers, poly(ethylene terephthalate) polyamide, or copolymers or any mixture thereof.

17. The implant material of claim 1, wherein the biocompatible binder comprises alginic acid, arabic gum, guar gum, xantham gum, gelatin, chitin, chitosan, chitosan acetate, chitosan lactate, chondroitin sulfate, N,O-carboxymethyl chitosan, a dextran, fibrin glue, glycerol, hyaluronic acid, sodium hyaluronate, a cellulose, glucosamine, proteoglycan, starch, lactic acid, pluronic, sodium glycerophosphate, collagen, glycogen, keratin, silk, or derivatives or any mixture thereof.

18. The implant material of claim 17, wherein the cellulose comprises methylcellulose, carboxy methylcellulose, hydroxypropyl methylcellulose, hydroxyethyl cellulose, or any mixture thereof.

19. The implant material of claim 17, wherein the dextran comprises α-cyclodextrin, β-cyclodextrin, γ-cyclodextrin, sodium dextran sulfate, or any mixture thereof.

20. The implant material of claim 1, wherein the biocompatible binder comprises collagen, polyglycolic acid, polylactic acid, or any mixture thereof.

21. The implant material of claim 1, wherein the biocompatible binder is water-soluble.

22. The implant material of claim 1, wherein the implant material is flowable.

23. The implant material of claim 1, wherein the implant material is a paste or a putty.

* * * * *